(12) United States Patent
Zhu

(10) Patent No.: US 8,906,650 B2
(45) Date of Patent: Dec. 9, 2014

(54) *YARROWIA* ESTERASE/LIPASE PROMOTER REGIONS FOR GENE EXPRESSION IN YEAST

(75) Inventor: Quinn Qun Zhu, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 130 days.

(21) Appl. No.: 13/435,291

(22) Filed: Mar. 30, 2012

(65) Prior Publication Data
US 2012/0252093 A1 Oct. 4, 2012

Related U.S. Application Data

(60) Provisional application No. 61/470,539, filed on Apr. 1, 2011.

(51) Int. Cl.
| *C12N 1/19* | (2006.01) |
| *C12P 21/00* | (2006.01) |
| *C12N 15/81* | (2006.01) |
| *C12P 21/02* | (2006.01) |
| *C12N 9/02* | (2006.01) |
| *C12N 9/10* | (2006.01) |
| *C12N 9/16* | (2006.01) |
| *C12P 7/64* | (2006.01) |

(52) U.S. Cl.
CPC .............. *C12N 15/81* (2013.01); *C12P 21/02* (2013.01); *C12N 9/0083* (2013.01); *C12N 9/1029* (2013.01); *C12N 9/16* (2013.01); *C12P 7/6427* (2013.01)
USPC ....................................... 435/71.1; 435/254.2

(58) Field of Classification Search
CPC ........ C12P 1/02; C12N 15/09; C12N 9/0083; C12N 2830/001; C07H 21/04
See application file for complete search history.

(56) References Cited

U.S. PATENT DOCUMENTS

2010/0062502 A1    3/2010   Hong et al.

FOREIGN PATENT DOCUMENTS

WO    2005049805 A2    6/2005

OTHER PUBLICATIONS

Dujon et al., Genome Evolution in Yeasts, Nature, vol. 430 (2004), pp. 35-44.
International Search Report, International Application No. PCT/US2012/031713.

*Primary Examiner* — Michele K Joike

(57) ABSTRACT

Promoter regions associated with the *Yarrowia lipolytica* esterase/lipase (EL1) gene are disclosed and have been found to be particularly effective for the expression of heterologous genes in yeast. These promoter regions will be useful for driving high-level expression of genes involved in the production of omega-3 and omega-6 fatty acids.

14 Claims, 9 Drawing Sheets

FIG. 2A

Figure 1:
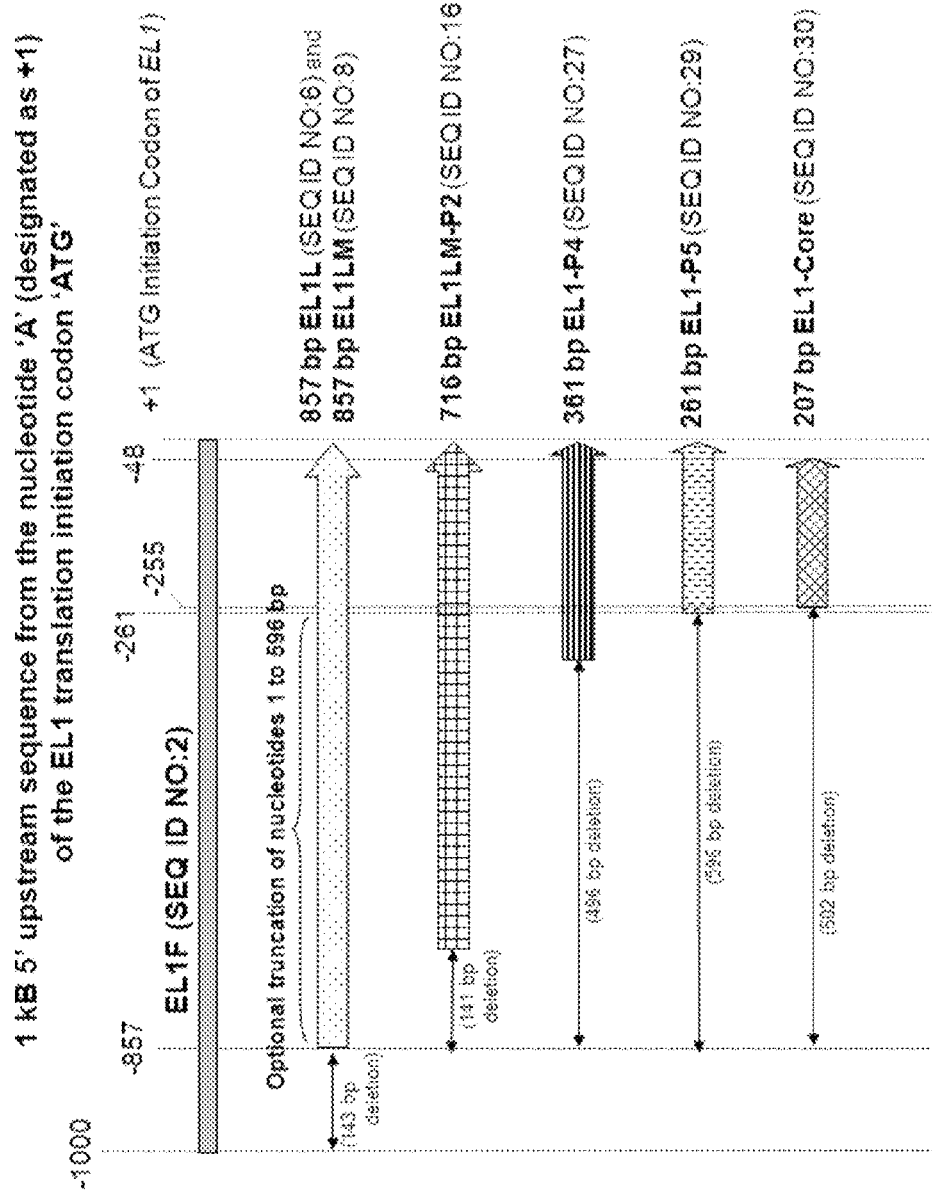

```
                          1
   1 kB ELIF     (SEQ ID NO:2)    AGGGACAGAATCAGTCTAGAGAACTGTTGAAAGGGAAGTATTCACACTGTCTCCGAAAAAAAA 60
 857 bp ELIL     (SEQ ID NO:6)    ------------------------------------------------------------
 720 bp ELILM-P2P1 (SEQ ID NO:21) ------------------------------------------------------------
 719 bp ELILM-P2P2 (SEQ ID NO:25) ------------------------------------------------------------
 716 bp ELILM-P2  (SEQ ID NO:16)  ------------------------------------------------------------
 361 bp ELi-P4   (SEQ ID NO:27)   ------------------------------------------------------------
 261 bp ELi-P5   (SEQ ID NO:29)   ------------------------------------------------------------
 207 bp ELi-Core (SEQ ID NO:30)   ------------------------------------------------------------

61
   1 kB ELIF     (SEQ ID NO:2)    AACAACTGCTAGCGGTCAATGTGAGTGCCATGTACCGGACAACAATTGAACGTTAGACACGAG 120
 857 bp ELIL     (SEQ ID NO:6)    ------------------------------------------------------------
 720 bp ELILM-P2P1 (SEQ ID NO:21) ------------------------------------------------------------
 719 bp ELILM-P2P2 (SEQ ID NO:25) ------------------------------------------------------------
 716 bp ELILM-P2  (SEQ ID NO:16)  ------------------------------------------------------------
 361 bp ELi-P4   (SEQ ID NO:27)   ------------------------------------------------------------
 261 bp ELi-P5   (SEQ ID NO:29)   ------------------------------------------------------------
 207 bp ELi-Core (SEQ ID NO:30)   ------------------------------------------------------------

121
   1 kB ELIF     (SEQ ID NO:2)    GCTGCAATGACAACCGCTATCGTCGATTGATTCGACTGAAACAACAAGATGAACGATGGCTG 180
 857 bp ELIL     (SEQ ID NO:6)    ------------------------------------------------------------
 720 bp ELILM-P2P1 (SEQ ID NO:21) ------------------------------------------------------------
 719 bp ELILM-P2P2 (SEQ ID NO:25) ---------------GATTGATTCGACTGGAAACAACAAGATAAAGATGGCTG
 716 bp ELILM-P2  (SEQ ID NO:16)  ------------------------------------------------------------
 361 bp ELi-P4   (SEQ ID NO:27)   ------------------------------------------------------------
 261 bp ELi-P5   (SEQ ID NO:29)   ------------------------------------------------------------
 207 bp ELi-Core (SEQ ID NO:30)   ------------------------------------------------------------

181
   1 kB ELIF     (SEQ ID NO:2)    ATCGGTTCATCTGCTTGACTTACATTCTGGATATATACGAGTCGCAGTGTGAGTTCCGAC 240
 857 bp ELIL     (SEQ ID NO:6)    AACGGTTCAATCGATCGCTGACTTACATTCTGGATATATACGAGAGTGCAGTGTGAGTTGAGTTCCGAC
 720 bp ELILM-P2P1 (SEQ ID NO:21) ------------------------------------------------------------
 719 bp ELILM-P2P2 (SEQ ID NO:25) ------------------------------------------------------------
 716 bp ELILM-P2  (SEQ ID NO:16)  ------------------------------------------------------------
 361 bp ELi-P4   (SEQ ID NO:27)   ------------------------------------------------------------
 261 bp ELi-P5   (SEQ ID NO:29)   ------------------------------------------------------------
 207 bp ELi-Core (SEQ ID NO:30)   ------------------------------------------------------------
```

FIG. 2B

```
                               241                                                                                   300
1 kB EL1F    (SEQ ID NO:2)     (241) TCAGACTGGGGAGGATGCGACCAGATCGAAATCCAGGACAGTTCTACACCTTGCAGAGT
857 bp EL1L  (SEQ ID NO:6)      (98) TCAGACTGGGGAGGATGCGACCAGATCGAAATCCAGGACAGTTCTACACCTTGCAGAGT
720 bp EL1lM-P2P1 (SEQ ID NO:21)  (1) ----------------------------------------CTACACCTTGCAGAGT
718 bp EL1lM-P2P2 (SEQ ID NO:25)  (1) ----------------------------------------CTACACCTTGCAGAGT
716 bp EL1lM-P2  (SEQ ID NO:16)   (1) ----------------------------------------CTACACCTTGCAGAGT
361 bp EL1-P4 (SEQ ID NO:27)      (1) ------------------------------------------------------------
261 bp EL1-P5 (SEQ ID NO:29)      (1) ------------------------------------------------------------
207 bp EL1-Core (SEQ ID NO:30)    (1) ------------------------------------------------------------

301                                                                                   360
1 kB EL1F    (SEQ ID NO:2)     (301) GGAGCTGCTCTCCATTCCAAGTCAGAGTGTGGACGTTCGGGCTTTTGAGAAGTCGA
857 bp EL1L  (SEQ ID NO:6)     (158) GGAGCTGCTCTCCATTCCAAGTCAGAGTGTGGACGTTCGGGCTTTTGAGAAGTCGA
720 bp EL1lM-P2P1 (SEQ ID NO:21)  (17) GGAGCTGCTCTCCATTCCAAGTCAGAGTGTGGACGTTCGGGCTTTTGAGAAGTCGA
718 bp EL1lM-P2P2 (SEQ ID NO:25)  (17) GGAGCTGCTCTCCATTCCAAGTCAGAGTGTGGACGTTCGGGCTTTTGAGAAGTCGA
716 bp EL1lM-P2  (SEQ ID NO:16)  (17) GGAGCTGCTCTCCATTCCAAGTCAGAGTGTGGACGTTCGGGCTTTTGAGAAGTCGA
361 bp EL1-P4 (SEQ ID NO:27)      (1) ------------------------------------------------------------
261 bp EL1-P5 (SEQ ID NO:29)      (1) ------------------------------------------------------------
207 bp EL1-Core (SEQ ID NO:30)    (1) ------------------------------------------------------------

361                                                                                   420
1 kB EL1F    (SEQ ID NO:2)     (361) GCAGAAACAGGCTCGAGTTGGGCGCATAAGTACCCTCTTCGATCTGTTAACCTGGAGTT
857 bp EL1L  (SEQ ID NO:6)     (218) GCAGAAACAGGCTCGAGTTGGGCGCATAAGTACCCTCTTCGATCTGTTAACCTGGAGTT
720 bp EL1lM-P2P1 (SEQ ID NO:21) (77) GCAGAAACAGGCTCGAGTTGGGCGCATAAGTACCCTCTTCGATCTGTTAACCTGGAGTT
718 bp EL1lM-P2P2 (SEQ ID NO:25) (77) GCAGAAACAGGCTCGAGTTGGGCGCATAAGTACCCTCTTCGATCTGTTAACCTGGAGTT
716 bp EL1lM-P2  (SEQ ID NO:16) (77) GCAGAAACAGGCTCGAGTTGGGCGCATAAGTACCCTCTTCGATCTGTTAACCTGGAGTT
361 bp EL1-P4 (SEQ ID NO:27)      (1) ------------------------------------------------------------
261 bp EL1-P5 (SEQ ID NO:29)      (1) ------------------------------------------------------------
207 bp EL1-Core (SEQ ID NO:30)    (1) ------------------------------------------------------------

421                                                                                   480
1 kB EL1F    (SEQ ID NO:2)     (421) GGGGTGTTATTTTGGATTATGATTATGATAAAAAAGAAAAGAAGAATGAAAAAAAAGAA
857 bp EL1L  (SEQ ID NO:6)     (278) GGGGTGTTATTTTGGATTATGATTATGATAAAAAAGAAAAGAAGAATGAAAAAAAAGAA
720 bp EL1lM-P2P1 (SEQ ID NO:21)(137) GGGGTGTTATTTTGGATTATGATTATGATAAAAAAGAAAAGAAGAATGAAAAAAAAGAA
718 bp EL1lM-P2P2 (SEQ ID NO:25)(137) GGGGTGTTATTTTGGATTATGATTATGATAAAAAAGAAAAGAAGAATGAAAAAAAAGAA
716 bp EL1lM-P2  (SEQ ID NO:16)(137) GGGGTGTTATTTTGGATTATGATTATGATAAAAAAGAAAAGAAGAATGAAAAAAAAGAA
361 bp EL1-P4 (SEQ ID NO:27)      (1) ------------------------------------------------------------
261 bp EL1-P5 (SEQ ID NO:29)      (1) ------------------------------------------------------------
207 bp EL1-Core (SEQ ID NO:30)    (1) ------------------------------------------------------------
```

FIG. 2C

```
                                                                                       540
                                            491
       1 kB EL1F  (SEQ ID NO:2)    (481) AAAAAGAAAAAAAAAAGAAAAAAAGAAGACAGTGACAATTAGCATG AACCATAAGAGCGA
     857 bp EL1L  (SEQ ID NO:6)    (338) AAAAAGAAAAAAAAAAGAAAAAAAGAAGACAGTGACAATTAGCATG AACCATAAGAGCGA
 720 bp EL1LM-P2P1 (SEQ ID NO:21)  (197) AAAAAGAAAAAAAAAAGAAAAAAAGAAGACAGTGACAATTAGCATC AACCATAAGAGCGA
 718 bp EL1LM-P2P2 (SEQ ID NO:25)  (197) AAAAAGAAAAAAAAAAGAAAAAAAGAAGACAGTGACAATTAGCATC AACCATAAGAGCGA
 716 bp EL1LM-P2  (SEQ ID NO:16)   (197) AAAAAAGAAAAAAAAAAGAAAAAAAGAAGACAGTGACAATTAGCATC AACCATAAGAGCGA
 361 bp EL1-P4   (SEQ ID NO:27)    (1)   ------------------------------------------------
 261 bp EL1-P5   (SEQ ID NO:29)    (1)   ------------------------------------------------
 207 bp EL1-Core (SEQ ID NO:30)    (1)   ------------------------------------------------

541                                         600
       1 kB EL1F  (SEQ ID NO:2)    (541) CACAAGAGACTCGAACTCAGAACACTTGTATCTGGCCACATGCTTCGTCTCTCTCAGTCT
     857 bp EL1L  (SEQ ID NO:6)    (398) CACAAGAGACTCGAACTCAGAACACTTGTATCTGGCCACATGCTTCGTCTCTCTCAGTCT
 720 bp EL1LM-P2P1 (SEQ ID NO:21)  (257) CACAAGAGACTCGAACTCAGAACACTTGTATCTGGCCACATGCTTCGTCTCTCTCAGTCT
 718 bp EL1LM-P2P2 (SEQ ID NO:25)  (257) CACAAGAGACTCGAACTCAGAACACTTGTATCTGGCCACATGCTTCGTCTCTCTCAGTCT
 716 bp EL1LM-P2  (SEQ ID NO:16)   (257) CACAAGAGACTCGAACTCAGAACACTTGTATCTGGCCACATGCTTCGTCTCTCTCAGTCT
 361 bp EL1-P4   (SEQ ID NO:27)    (1)   ------------------------------------------------
 261 bp EL1-P5   (SEQ ID NO:29)    (1)   ------------------------------------------------
 207 bp EL1-Core (SEQ ID NO:30)    (1)   ------------------------------------------------

601                                         660
       1 kB EL1F  (SEQ ID NO:2)    (601) CTCCATCGCTTCTAAATTACCCCAACATGTGCCAAAGTT CAATGCTAGACAGCAGCAAT
     857 bp EL1L  (SEQ ID NO:6)    (458) CTCCATCGCTTCTAAATTACCCCAACATGTGCCAAAGTT CAATGCTAGACAGCAGCAAT
 720 bp EL1LM-P2P1 (SEQ ID NO:21)  (317) CTCCATCGCTTCTAAATTACCCCAACATGTGCCAAAGTT CAATGCTAGACAGCAGCAAT
 718 bp EL1LM-P2P2 (SEQ ID NO:25)  (317) CTCCATCGCTTCTAAATTACCCCAACATGTGCCAAAGTT CAATGCTAGACAGCAGCAAT
 716 bp EL1LM-P2  (SEQ ID NO:16)   (317) CTCCATCGCTTCTAAATTACCCCAACATGTGCCAAAGTT CAATGCTAGACAGCAGCAAT
 361 bp EL1-P4   (SEQ ID NO:27)    (1)   ------------------------------------------------
 261 bp EL1-P5   (SEQ ID NO:29)    (1)   ------------------------------------------------
 207 bp EL1-Core (SEQ ID NO:30)    (1)   ------------------------------------------------

661                                         720
       1 kB EL1F  (SEQ ID NO:2)    (657) AGGGTTCCCCCCACAATCTTGGGCAGATGAGAGTGGGCGGAGGAGATGTCATGGTCAAT
     857 bp EL1L  (SEQ ID NO:6)    (514) AGGGTTCCCCCCACAATCTTGGGCAGATGAGAGTGGGCGGAGGAGATGTCATGGTCAAT
 720 bp EL1LM-P2P1 (SEQ ID NO:21)  (373) AGGGTTCCCCCCACAATCTTGGGCAGATGAGAGTGGGCGGAGGAGATGTCATGGTCAAT
 718 bp EL1LM-P2P2 (SEQ ID NO:25)  (373) AGGGTTCCCCCCACAATCTTGGGCAGATGAGAGTGGGCGGAGGAGATGTCATGGTCAAT
 716 bp EL1LM-P2  (SEQ ID NO:16)   (373) AGGGTTCCCCCCACAATCTTGGGCAGATGAGAGTGGGCGGAGGAGATGTCATGGTCAAT
 361 bp EL1-P4   (SEQ ID NO:27)    (18)  AGGGTTCCCCCCACAATCTTGGGCAGATGAGAGTGGGCGGAGGAGATGTCATGGTCAAT
 261 bp EL1-P5   (SEQ ID NO:29)    (1)   ------------------------------------------------
 207 bp EL1-Core (SEQ ID NO:30)    (1)   ------------------------------------------------
```

FIG. 2D

```
                                         721                                                           780
      1 kB ELIF    (SEQ ID NO:2)   (717) TGTGGCGTCAATGGAGCGAGCGTTTA TGGGCCCAAAAGTTGATAGGGTCGTTCATTGACAG
    857 bp ELIL    (SEQ ID NO:6)   (574) TGTGGCGTCAATGGAGCGAGCGTTTA TGGGCCCAAAAGTTGATAGGGTCGTTCATTGACAG
720 bp ELILM-P2P1  (SEQ ID NO:21)  (437) TGTGGCGTCAATGGAGCGAGCGTTTA TGGGCCCAAAAGTTGATAGGGTCGTCATTGACAG
718 bp ELILM-P2P2  (SEQ ID NO:25)  (433) TGTGGCGTCAATGGAGCGAGCGTTTA TGGGCCCAAAAGTTGATAGGGTCGTTCATTGACAG
716 bp ELILM-P2    (SEQ ID NO:16)  (433) TGTGGCGTCAATGGAGCGAGCGTTTA TGGGCCCAAAAGTTGATAGGGTCGTTCATTGACAG
361 bp ELI-P4      (SEQ ID NO:27)   (78) TGTGGCGTCAATGGAGCGAGCGTTTA TGGGCCCAAAAGTTGATAGGGTCGTTCATTGACAG
261 bp ELI-P5      (SEQ ID NO:29)    (1) ------------------------- TGGGCCCAAAAGTTGATAGGGTCGTTCATTGACAG
207 bp ELI-Core    (SEQ ID NO:30)    (1) ------------------------- CAAAAGTGATTAGGGTCGTTCATTGACAG 781                                                           840
      1 kB ELIF    (SEQ ID NO:2)   (775) ATTAGGATTGTAGCGGTCAAAAGAACCCCCGAAAAAGTCCCTCGACACTCTCTACCA
    857 bp ELIL    (SEQ ID NO:6)   (632) ATTAGGATTGTAGCGGTCAAAAGAACCCCCGAAAAAGTCCCTCGACACTCTCTACCA
720 bp ELILM-P2P1  (SEQ ID NO:21)  (495) ATTAGGATTGTAGCGGTCAAAAGAACCCCCGAAAAAGTCCCTCGACACTCTCTACCA
718 bp ELILM-P2P2  (SEQ ID NO:25)  (493) ATTAGGATTGTAGCGGTCAAAAGAACCCCCGAAAAAGTCCCTCGACACTCTCTACCA
716 bp ELILM-P2    (SEQ ID NO:16)  (491) ATTAGGATTGTAGCGGTCAAAAGAACCCCCGAAAAAGTCCCTCGACACTCTCTACCA
361 bp ELI-P4      (SEQ ID NO:27)  (136) ATTAGGATTGTAGCGGTCAAAAGAACCCCCGAAAAAGTCCCTCGACACTCTCTACCA
261 bp ELI-P5      (SEQ ID NO:29)   (36) ATTAGGATTGTAGCGGTCAAAAGAACCCCCGAAAAAGTCCCTCGACACTCTCTACCA
207 bp ELI-Core    (SEQ ID NO:30)   (30) ATTAGGATTGTAGCGGTCAAAAGAACCCCCGAAAAAGTCCCTCGACACTCTCTACCA 841                                                           900
      1 kB ELIF    (SEQ ID NO:2)   (835) TCTCCCCAAAATCGCCTTCATGNGATAAACTCTAGCGCGGCCGTTACTCTAACGAACT
    857 bp ELIL    (SEQ ID NO:6)   (692) TCTCCCCAAAATCGCCTTCATGTGATAAACTCTAGCGCGGCCGTTACTCTAACGAACT
720 bp ELILM-P2P1  (SEQ ID NO:21)  (555) TCTCCCCAAAATCGCCTTCATGTGATGTAAACTCTAGCGCGGCCGTTACTCTAACGAACT
718 bp ELILM-P2P2  (SEQ ID NO:25)  (553) TCTCCCCAAAATCGCCTTCATGTGATGAAAACTCTAGCGCGGCCGTTACTCTAACGAACT
716 bp ELILM-P2    (SEQ ID NO:16)  (551) TCTCCCCAAAATCGCCTTCATGTGATGATAACTCTAGCGCGGCCGTTACTCTAACGAACT
361 bp ELI-P4      (SEQ ID NO:27)  (196) TCTCCCCAAAATCGCCTTCATGTGATAAACTCTAGCGCGGCCGTTACTCTAACGAACT
261 bp ELI-P5      (SEQ ID NO:29)   (96) TCTCCCCAAAATCGCCTTCATGTGATAAACTCTAGCGCGGCCGTTACTCTAACGAACT
207 bp ELI-Core    (SEQ ID NO:30)   (90) TCTCCCCAAAATCGCCTTCATGTGATAAACTCTAGCGCGGCCGTTACTCTAACGAACT 901                                                           960
      1 kB ELIF    (SEQ ID NO:2)   (895) TAGAGACAATTCACATGCGGAGGTACCGTAGCTACACAAGTACACCAGTAGAGGAAGTCCAAGTG
    857 bp ELIL    (SEQ ID NO:6)   (752) TAGAGACAATTCACATGCGGAGGTACCGTAGCTACACAAGTACACCAGTAGAGGAAGTCCAAGTG
720 bp ELILM-P2P1  (SEQ ID NO:21)  (615) TAGAGACAATTCACATGCGGAGGTACCGTAGCTACACAAGTACACCAGTAGAGGAAGTCCAAGTG
718 bp ELILM-P2P2  (SEQ ID NO:25)  (613) TAGAGACAATTCACATGCGGAGGTACCGTAGCTACACAAGTACACCAGTAGAGGAAGTCCAAGTG
716 bp ELILM-P2    (SEQ ID NO:16)  (611) TAGAGACAATTCACATGCGGAGGTACCGTAGCTACACAAGTACACCAGTAGAGGAAGTCCAAGTG
361 bp ELI-P4      (SEQ ID NO:27)  (256) TAGAGACAATTCACATGCGGAGGTACCGTAGCTACACAAGTACACCAGTAGAGGAAGTCCAAGTG
261 bp ELI-P5      (SEQ ID NO:29)  (156) TAGAGACAATTCACATGCGGAGGTACCGTAGCTACACAAGTACACCAGTAGAGGAAGTCCAAGTG
207 bp ELI-Core    (SEQ ID NO:30)  (150) TAGAGACAATTCACATGCGGAGGTACCGTAGCTACACAAGTACACCAGTAGAGGAAGTCCAAG--
```

FIG. 2E

```
                               961
1 KB EliF      (SEQ ID NO:2)   GATAAATCGTCTTCCCGAATACCGACTTTCTCACCACCAATTA (1006)
857 bp EliL    (SEQ ID NO:6)   GATAAATCGTCTTCCCGAATACCGACTTTCTCACCACCAATTC (855)
720 bp EliLM-P2P1 (SEQ ID NO:21) GATAAATCGTCTTCCCGAATACCGACTTTCTCACCACCAATTC (812)
718 bp EliLM-P2P2 (SEQ ID NO:25) GATAAATCGTCTTCCCGAATACCGACTTTCTCACCACCAATTC (675)
716 bp EliLM-P2 (SEQ ID NO:16) GATAAATCGTCTTCCCGAATACCGACTTTCTCACCACCAATTC (673)
361 bp Eli-P4  (SEQ ID NO:27)  GATAAATCGTCTTCCCGAATACCGACTTTCTCACCACCAATTC (671)
261 bp Eli-P5  (SEQ ID NO:29)  GATAAATCGTCTTCCCGAATACCGACTTTCTCACCACCAATTC (316)
207 bp Eli-Core (SEQ ID NO:30) GATAAATCGTCTTCCCGAATACCGACTTTCTCACCACCAATTC (216)
                               --------------------------------------------  (20)
```

YARROWIA ESTERASE/LIPASE PROMOTER REGIONS FOR GENE EXPRESSION IN YEAST

This application claims the benefit of U.S. Provisional Application No. 61/470,539, filed Apr. 1, 2011, which is incorporated herein by reference in its entirety.

FIELD OF THE INVENTION

This invention is in the field of biotechnology. More specifically, this invention pertains to esterase/lipase ["EL1"] promoter regions derived from *Yarrowia lipolytica* that are useful for gene expression in yeast.

BACKGROUND OF THE INVENTION

Oleaginous yeast are defined as those organisms that are naturally capable of oil synthesis and accumulation, wherein oil accumulation ranges from at least about 25% up to about 80% of the dry cell weight. The technology for growing oleaginous yeast with high oil content is well developed (for example, see EP 0 005 277B1; Ratledge, C., *Prog. Ind. Microbiol.*, 16:119-206 (1982)). And, these organisms have been commercially used for a variety of purposes in the past.

Recently, the natural abilities of oleaginous yeast have been enhanced by advances in genetic engineering, resulting in organisms capable of producing polyunsaturated fatty acids ["PUFAs"], carotenoids, resveratrol and sterols. For example, significant efforts by Applicants' Assignee have demonstrated that *Yarrowia lipolytica* can be engineered for production of omega-3 and omega-6 fatty acids, by introducing and expressing genes encoding the omega-3/omega-6 biosynthetic pathway (U.S. Pat. Nos. 7,238,482; 7,465,564; 7,550,286; 7,588,931; and 7,932,077; U.S. Pat. Appl. Publ. Nos. 2009-0093543-A1 and 2010-0317072-A1).

Recombinant production of any heterologous protein is generally accomplished by constructing an expression cassette in which the DNA coding for the protein of interest is placed under the control of a promoter suitable for the host cell. The expression cassette is then introduced into the host cell (i.e., usually by plasmid-mediated transformation or targeted integration into the host genome) and production of the heterologous protein is achieved by culturing the transformed host cell under conditions necessary for the proper function of the promoter contained within the expression cassette. Thus, the development of new host cells (e.g., transformed yeast) for recombinant production of proteins generally requires the availability of promoters that are suitable for controlling the expression of a protein of interest in the host cell.

A variety of strong promoters have been isolated from *Yarrowia lipolytica* that are useful for heterologous gene expression in yeast, as shown in the Table below.

TABLE 1

Characterized *Yarrowia lipolytica* Promoters

| Promoter Name | Native Gene | Reference |
|---|---|---|
| XPR2 | alkaline extracellular protease | U.S. Pat. No. 4,937,189; EP220864 |
| TEF | translation elongation factor EF1-α (tef) | U.S. Pat. No. 6,265,185 |
| GPD, GPM | glyceraldehyde-3-phosphate-dehydrogenase (gpd), phosphoglycerate mutase (gpm) | U.S. Pat. Nos. 7,259,255 and 7,459,546; U.S. Pat. Appl. Publ. No. 2011-0059496-A1 |
| GPDIN | glyceraldehyde-3-phosphate-dehydrogenase (gpd) | U.S. Pat. No. 7,459,546 |
| GPM/FBAIN | chimeric phosphoglycerate mutase (gpm)/fructose-bisphosphate aldolase (fba1) | U.S. Pat. No. 7,202,356 |
| FBA, FBAIN, FBAINm | fructose-bisphosphate aldolase (fba1) | U.S. Pat. No. 7,202,356 |
| GPAT | glycerol-3-phosphate O-acyltransferase (gpat) | U.S. Pat. No. 7,264,949 |
| YAT1 | ammonium transporter enzyme (yat1) | U.S. Pat. Appl. Publ. Nos. 2006-0094102-A1 and 2010-0068789-A1 |
| EXP1 | export protein | U.S. Pat. No. 7,932,077 |

Additionally, Juretzek et al. (*Biotech. Bioprocess Eng.*, 5:320-326 (2000)) compares the glycerol-3-phosphate dehydrogenase ["G3P"], isocitrate lyase ["ICL1"], 3-oxo-acyl-CoA thiolase ["POT1"] and acyl-CoA oxidase ["POX1", "POX2" and "POX5"] promoters with respect to their regulation and activities during growth on different carbon sources.

Despite the utility of these known promoters, however, there is a need for new improved yeast promoters for metabolic engineering of yeast (i.e., oleaginous and non-oleaginous) and for controlling the expression of heterologous genes in yeast. Furthermore, possession of a suite of promoters that can be regulated under a variety of natural growth and induction conditions in yeast will play an important role in industrial settings, wherein economical production of heterologous and/or homologous polypeptides in commercial quantities is desirable.

It is believed that promoter regions derived from the *Yarrowia lipolytica* gene encoding esterase/lipase ["EL1"] will be useful in expressing heterologous and/or homologous genes in transformed yeast, including *Yarrowia*.

SUMMARY OF THE INVENTION

In a first embodiment, the invention concerns a method for expressing a coding region of interest in a transformed yeast cell comprising:
    a) providing a transformed yeast cell having a recombinant construct, wherein the recombinant construct comprises:

(1) a promoter region of an EL1 *Yarrowia* gene; and
(2) a coding region of interest which is expressible in the yeast cell;
wherein the promoter region is operably linked to the coding region of interest; and
b) growing the transformed yeast cell of step (a) under conditions whereby the recombinant construct of step (a) is expressed.

In a second embodiment, the invention concerns a method for the production of an omega-3 fatty acid or omega-6 fatty acid comprising:
a) providing a transformed oleaginous yeast cell comprising a recombinant construct, wherein the recombinant construct comprises:
  i) a promoter region of an EL1 *Yarrowia* gene; and
  ii) a coding region encoding at least one omega-3 fatty acid or omega-6 fatty acid biosynthetic pathway enzyme;
wherein the promoter region and the coding region are operably linked;
b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
c) optionally recovering the omega-3 fatty acid or the omega-6 fatty acid.

In another aspect, the promoter region of a *Yarrowia* gene may comprise a sequence selected from the group consisting of SEQ ID NO:30 and SEQ ID NO:32.

In yet another aspect, the promoter region of the EL1 *Yarrowia* gene further comprises an enhancer region set forth in SEQ ID NO:33, the enhancer region being operably linked to a functional yeast promoter.

In some embodiments, the promoter region of an EL1 *Yarrowia* gene may be as set forth in SEQ ID NO:6, wherein said promoter optionally comprises at least one modification selected from the group consisting of:
a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;
b) substitution of an adenine ['A'] nucleotide for the cytosine ['C'] nucleotide at position 856 of SEQ ID NO:6;
c) substitution of a thymine ['T'] nucleotide or a guanine ['G'] nucleotide for the cytosine ['C'] nucleotide at position +856 of SEQ ID NO:6;
d) substitution of a cytosine ['C'] nucleotide for the guanine ['G'] nucleotide at position 382 of SEQ ID NO:6;
e) substitution of an adenine ['A'] nucleotide or a thymine ['T'] nucleotide for the guanine ['G'] nucleotide at position 382 of SEQ ID NO:6;
f) insertion of a nucleotide sequence 'TAAA' between position 496 and position 497 of SEQ ID NO:6;
g) insertion of a nucleotide sequence 'AC' between position 596 and 597 of SEQ ID NO:6; and
h) any combination of part a), part b), part c), part d), part e), part f), and part g) above.

More preferably, the promoter region of an EL1 *Yarrowia* gene may be as set forth in SEQ ID NO:29, wherein said promoter comprises at least one modification selected from the group consisting of:
a) a deletion at the 5'-terminus of 1, 2, 3, 4, 5, or 6, consecutive nucleotides, wherein the first nucleotide deleted is the thymine nucleotide ['T'] at position 1 of SEQ ID NO:29;
b) a deletion at the 3'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 consecutive nucleotides, wherein the first nucleotide deleted is the cytosine ['C'] at position 261 of SEQ ID NO:29; and
c) a deletion of part (a) in combination with a substitution of a thymine ['T'] nucleotide, adenine ['A'] nucleotide or a guanine ['G'] nucleotide for the cytosine ['C'] nucleotide at position 260 of SEQ ID NO:29.

The promoter region of an EL1 *Yarrowia* gene may be selected from the group consisting of SEQ ID NO:6, SEQ ID NO:8, SEQ ID NO:16, SEQ ID NO:21, SEQ ID NO:25, SEQ ID NO:27, and SEQ ID NO:29.

In various embodiments of the methods of the invention, the transformed yeast cell is an oleaginous yeast. This oleaginous yeast may be a member of a genus selected from the group consisting of *Yarrowia, Candida, Rhodotorula, Rhodosporidium, Cryptococcus, Trichosporon* and *Lipomyces*.

Additionally, provided herein is an isolated nucleic acid molecule comprising a promoter region of an EL1 *Yarrowia* selected from the group consisting of:

(a) SEQ ID NO:8;
(b) SEQ ID NO:16;
(c) SEQ ID NO:21;
(d) SEQ ID NO:25;
(e) SEQ ID NO:27;
(f) SEQ ID NO:29;
(g) SEQ ID NO:6, wherein said promoter optionally comprises at least one modification selected from the group consisting of:
  (i) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;
  (ii) substitution of an adenine ['A'] nucleotide for the cytosine ['C'] nucleotide at position 856 of SEQ ID NO:6;
  (iii) substitution of a thymine ['T'] nucleotide or a guanine ['G'] nucleotide for the cytosine ['C'] nucleotide at position 856 of SEQ ID NO:6;
  (iv) substitution of a cytosine ['C'] nucleotide for the guanine ['G'] nucleotide at position 382 of SEQ ID NO:6;
  (v) substitution of an adenine ['A'] nucleotide or a thymine ['T'] nucleotide for the guanine ['G'] nucleotide at position 382 of SEQ ID NO:6;
  (vi) insertion of a nucleotide sequence 'TAAA' between position 496 and position 497 of SEQ ID NO:6;
  (vii) insertion of a nucleotide sequence 'AC' between position 596 and 597 of SEQ ID NO:6; and
  (viii) any combination of part (i), part (ii), part (iii), part (iv), part (v), part (vi), and part (vii) above; and
(h) a promoter region comprising SEQ ID NO:32.

Also provided herein is an isolated nucleic acid molecule comprising a promoter region of an EL1 *Yarrowia* gene, wherein the promoter region of the EL1 *Yarrowia* gene further comprises an enhancer region set forth in SEQ ID NO:33, the enhancer region being operably linked to a functional yeast promoter.

BRIEF DESCRIPTION OF THE DRAWINGS AND SEQUENCE DESCRIPTIONS

FIG. 1 graphically represents the relationship between SEQ ID NOs:2, 6, 16, 27, 29, and 30, each of which relates to promoter regions derived from the 5' upstream region of the esterase/lipase ["EL1"] gene in *Yarrowia lipolytica*.

FIGS. 2A, 2B, 2C, 2D, and 2E (which should be viewed together as FIG. 2) provide an alignment of:
(a) the *Y. lipolytica* EL1F (SEQ ID NO:2) promoter region, which is the 1000 bp 5' upstream sequence (i.e., the −1000 to −1 region) of the esterase/lipase ["EL1"] gene in *Y. lipolytica*, wherein the nucleotide 'A' of the EL1 translation initiation codon 'ATG' was designated as +1 (note that the ATG codon is not shown in the figure);
(b) the 857 bp EL1L (SEQ ID NO:6) promoter region;
(c) the 720 bp EL1LM-P2P1 (SEQ ID NO:21) promoter region;
(d) the 718 bp EL1LM-P2P2 (SEQ ID NO:25) promoter region;
(e) the 716 bp EL1LM-P2 (SEQ ID NO:16) promoter region;
(f) the 361 bp EL1-P4 (SEQ ID NO:27) promoter region;
(g) the 261 bp EL1-P5 (SEQ ID NO:29) promoter region; and
(h) the 207 bp EL1 minimal (Core) (SEQ ID NO:30) promoter region.

Base pair differences are highlighted with an arrow and box.

Figure 3:
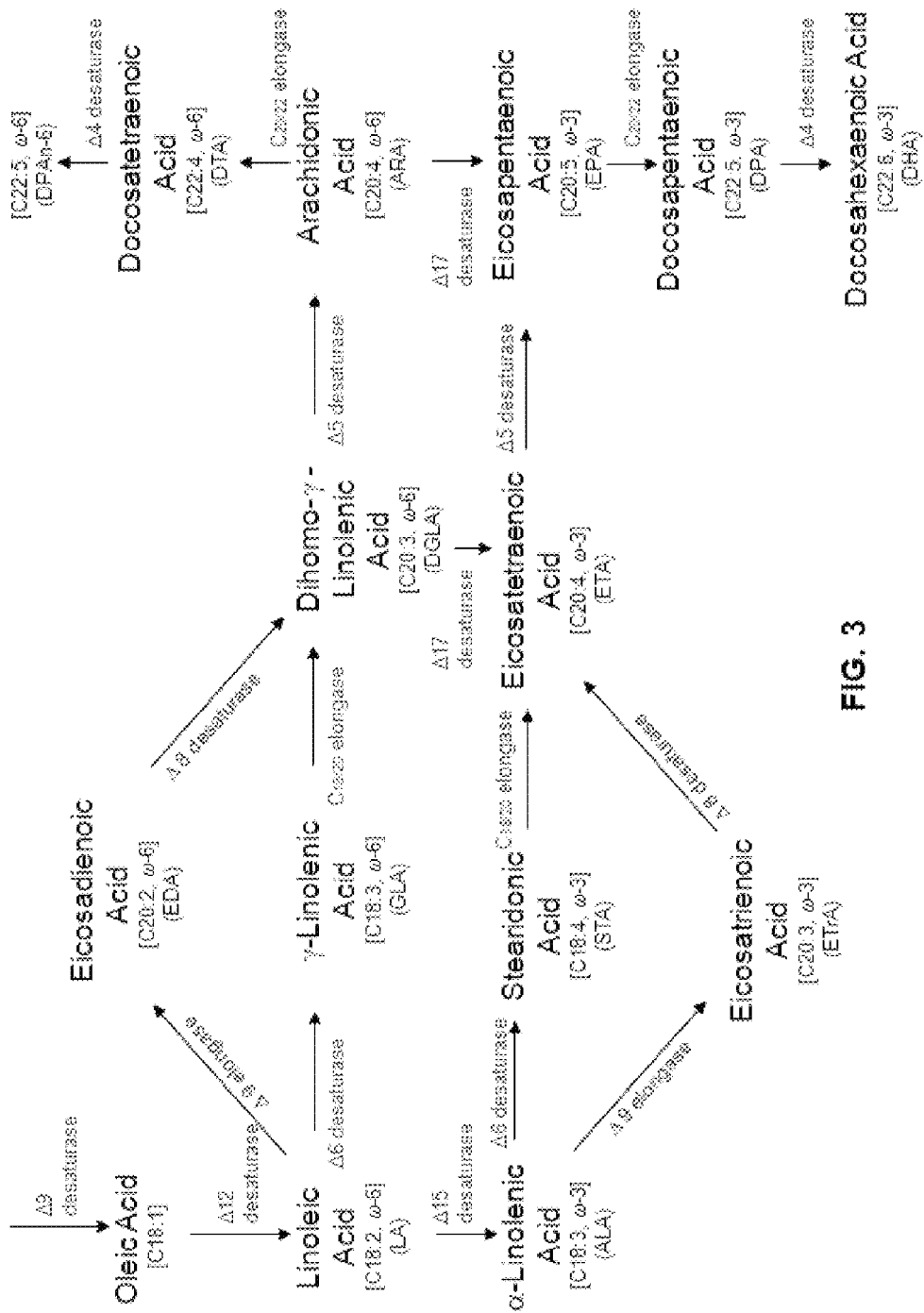

FIG. 3 illustrates the omega-3/omega-6 fatty acid biosynthetic pathway.

Figure 4B:
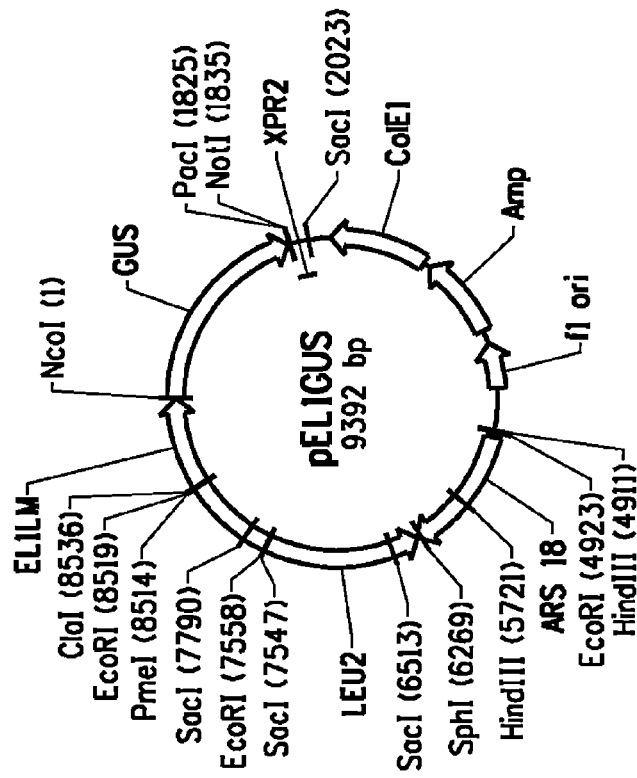
Figure 4A:
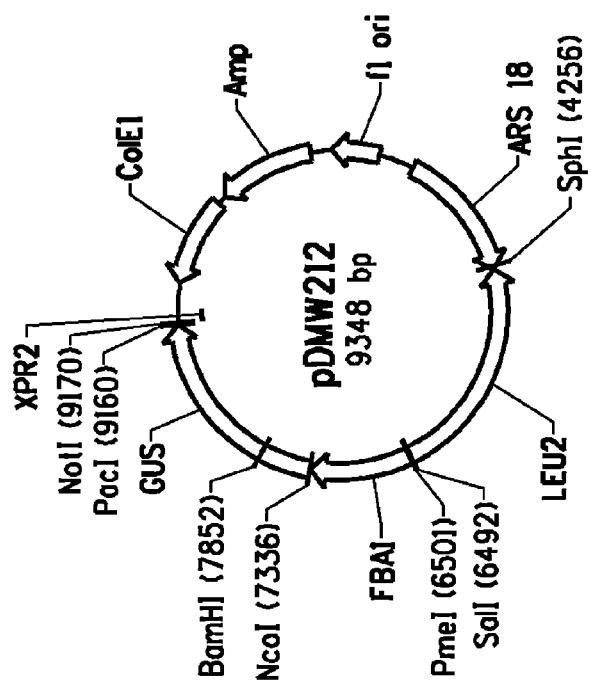

FIG. 4 provides plasmid maps for the following: (A) pDMW212 and (B) pEL1GUS.

Figure 5:
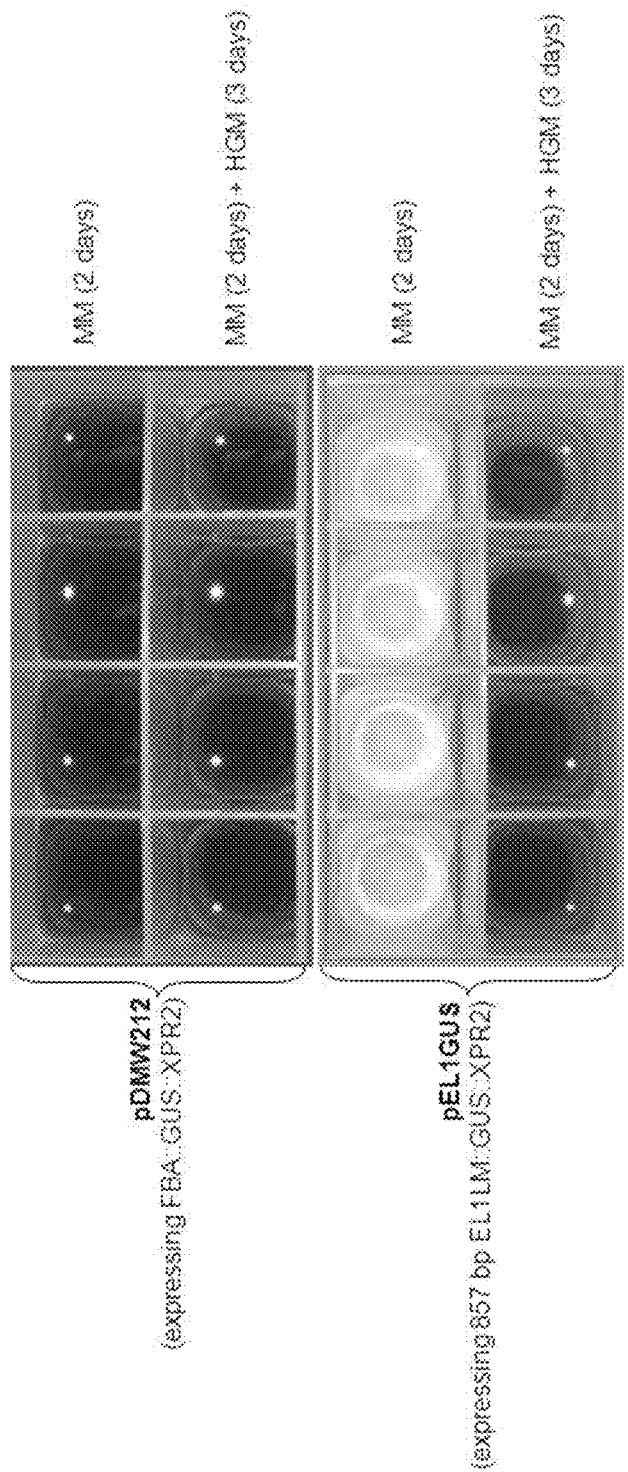

FIG. 5 is an image of cell cultures comparing the promoter activity of 857 bp EL1LM (SEQ ID NO:8) and FBA in *Yarrowia lipolytica* as determined by histochemical staining.

The invention can be more fully understood from the following detailed description and the accompanying sequence descriptions, which form a part of this application.

SEQ ID NOs:1-33 are promoters, ORFs encoding genes (or portions thereof), primers, or plasmids, as identified in Table 2.

| Description | Nucleic acid SEQ ID NO. |
|---|---|
| *Yarrowia* EL1 gene ("YALI0E19899g") | 1 (2359 bp) |
| 1000 bp EL1F *Yarrowia* promoter region | 2 (1000 bp) |
| Primer Y1210 | 3 (34 bp) |
| Primer Y1211 | 4 (38 bp) |
| Plasmid pT-EL1 | 5 (4824 bp) |
| 857 bp EL1L *Yarrowia* promoter region | 6 (857 bp) |
| Plasmid pT-EL1-(S) | 7 (4824 bp) |
| 857 bp EL1LM *Yarrowia* promoter region | 8 (857 bp) |
| Primer Y1212 | 9 (35 bp) |
| Primer Y1213 | 10 (35 bp) |
| Plasmid pT-EL1-(S)P2 | 11 (4828 bp) |
| Primer Y1242 | 12 (38 bp) |
| Primer Y1243 | 13 (38 bp) |
| Plasmid pDMW212 | 14 (9348 bp) |
| Plasmid pEL1GUS | 15 (9392 bp) |
| 716 bp EL1LM-P2 *Yarrowia* promoter region | 16 (716 bp) |
| Plasmid pEL1GUS2 | 17 (9231 bp) |
| Primer Y1254 | 18 (39 bp) |
| Primer Y1255 | 19 (39 bp) |
| Plasmid pEL1GUS2-P1 | 20 (9226 bp) |
| 720 bp EL1LM-P2P1 *Yarrowia* promoter region | 21 (720 bp) |
| Primer Y1256 | 22 (36 bp) |
| Primer Y1257 | 23 (36 bp) |
| Plasmid pEL1GUS2-P2 | 24 (9224 bp) |
| 718 bp EL1LM-P2P2 *Yarrowia* promoter region | 25 (718 bp) |
| Plasmid pEL1GUS2-P4 | 26 (8667 bp) |
| 361 bp EL1-P4 *Yarrowia* promoter region | 27 (361 bp) |
| Plasmid pEL1GUS2-P5 | 28 (8768 bp) |
| 261 bp EL1-P5 *Yarrowia* promoter region | 29 (261 bp) |
| 207 bp EL1 Minimal promoter | 30 (207 bp) |
| 861 bp EL1LM + Pme *Yarrowia* promoter region | 31 (861 bp) |
| 255 bp EL1 Minimal promoter region | 32 (255 bp) |
| 357 bp EL1 *Yarrowia* enhancer region | 33 (357 bp) |

DETAILED DESCRIPTION OF THE INVENTION

All patents, patent applications, and publications cited herein are hereby incorporated by reference in their entirety.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

The term "yeast" refers to a phylogenetically diverse grouping of single-celled fungi. Yeast do not form a specific taxonomic or phylogenetic grouping, but instead comprise a diverse assemblage of unicellular organisms that occur in the Ascomycotina and Basidiomycotina. Collectively, about 100 genera of yeast have been identified, comprising approximately 1,500 species (Kurtzman and Fell, *Yeast Systematics And Phylogeny: Implications Of Molecular Identification Methods For Studies In Ecology*. In C. A. Rosa and G. Peter, eds., *The Yeast Handbook*. Germany: Springer-Verlag Berlin Herdelberg, 2006). Yeast reproduce principally by budding (or fission) and derive energy from fermentation, via conversion of carbohydrates to ethanol and carbon dioxide. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

The term "oleaginous" refers to those organisms that tend to store their energy source in the form of oil (Weete, In: Fungal Lipid Biochemistry, $2^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are not limited to, the following genera: *Yarrowia, Candida, Rhodotorula, Rhodosporidium, Cryptococcus, Trichosporon* and *Lipomyces*. Alternatively, organisms classified as yeasts that are genetically modified to become oleaginous such that they can produce more than 25% of their dry cell weight as oil are also "oleaginous", e.g., yeast such as *Saccharomyces cerevisiae* (Intl Appl. Pub. No. WO 2006/102342).

The term "fermentable carbon source" will refer to a carbon source that a microorganism will metabolize to derive energy. Typical carbon sources for use in the methods herein include, but are not limited to: monosaccharides, disaccharides, oligosaccharides, polysaccharides, alkanes, fatty acids, esters of fatty acids, glycerol, monoglycerides, diglycerides, triglycerides, carbon dioxide, methanol, formaldehyde, formate and carbon-containing amines. Most preferred is glucose, sucrose, invert sucrose, fructose, glycerol and/or fatty acids containing between 10-22 carbons. The term "invert sucrose" (or "invert sugar") refers to a mixture comprising equal parts of fructose and glucose resulting from the hydrolysis of sucrose. Invert sucrose may be a mixture comprising 25 to 50% glucose and 25 to 50% fructose. Invert sucrose may also comprise sucrose, the amount of which depends on the degree of hydrolysis.

The term "EL1" refers to a hypothetical protein weakly homologous to esterase/lipase ("YALI0E19899g", Dujon, B. et al., *Nature*, 430(6995):35-44 (2004)) encoded by the EL1 gene and its transcription was increased in *Yarrowia* strains with their native snf1 gene knocked-out (U.S. Pat. Appl. Publ. No. 2010-0062502-A1). The EL1 enzyme catalyzes the hydrolysis of fatty acid ester bonds in triacylglycerols to release free fatty acids.

An "EL1 *Yarrowia* gene" refers to a gene encoding EL1 from a yeast of the genus *Yarrowia*. For example, a 2,239 bp DNA sequence ("YALI0E19899g") that encodes a hypothetical protein weakly homologous to Esterase/Lipase is provided as SEQ ID NO:1 (Dujon, B. et al., *Nature*, 430(6995): 35-44 (2004)).

The term "promoter region of an EL1 *Yarrowia* gene" or "*Yarrowia* EL1 promoter region" refers to the 5' upstream untranslated region in front of the 'ATG' translation initiation codon of a *Yarrowia* EL1 gene, or sequences derived therefrom, and that is necessary for expression. Thus, it is believed that promoter regions of an EL1 *Yarrowia* gene will comprise a portion of the ~1000 bp 5' upstream of an EL1 *Yarrowia* gene. The sequence of the *Yarrowia* EL1 promoter region may correspond exactly to native sequence upstream of the EL1 *Yarrowia* gene (i.e., a "wildtype" or "native" *Yarrowia* EL1 promoter); alternately, the sequence of the *Yarrowia* EL1 promoter region may be "modified" or "mutated", thereby comprising various substitutions, deletions, and/or insertions of one or more nucleotides relative to a wildtype or native *Yarrowia* EL1 promoter. These modifications can result in a modified *Yarrowia* EL1 promoter having increased, decreased or equivalent promoter activity, when compared to the promoter activity of the corresponding wildtype or native *Yarrowia* EL1 promoter. The term "mutant promoter" or "modified promoter" will encompass natural variants and in vitro generated variants obtained using methods well known in the art (e.g., classical mutagenesis, site-directed mutagenesis and "DNA shuffling").

Described herein is a wildtype *Yarrowia* EL1 promoter region (SEQ ID NO:2) comprising the −1000 to −1 upstream region of the EL1 gene (SEQ ID NO:1) based on nucleotide numbering such that the 'A' position of the 'ATG' translation initiation codon is designated as +1. The ATG translation initiation codon is located at nucleotide positions 1001-1003 in SEQ ID NO:1. Alternately, and yet by no means limiting in nature, a wildtype *Yarrowia* EL1 promoter region may comprise the −857 to −1 region of SEQ ID NO:1, the −720 to −1 region of SEQ ID NO:1, the −718 to −1 region of SEQ ID NO:1, the −716 to −1 region of SEQ ID NO:1, the −361 to −1 region of SEQ ID NO:1, the −261 to −1 region of SEQ ID NO:1, the −255 to −1 region of SEQ ID NO:1; or the −255 to −48 region of SEQ ID NO:1 (where the "−1" position in SEQ ID NO:1 is the nucleotide that is 5'-adjacent to the ATG translation initiation codon). Similarly, a modified *Yarrowia* EL1 promoter region may comprise the promoter region of a EL1 *Yarrowia* gene as set forth in SEQ ID NO:6, wherein said promoter optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;

b) substitution of an adenine ['A'] nucleotide for the cytosine ['C'] nucleotide at position 856 of SEQ ID NO:6;

c) substitution of a thymine ['T'] nucleotide or a guanine ['G'] nucleotide for the cytosine ['C'] nucleotide at position 856 of SEQ ID NO:6;

d) substitution of a cytosine ['C'] nucleotide for the guanine ['G'] nucleotide at position 382 of SEQ ID NO:6;

e) substitution of an adenine ['A'] nucleotide or a thymine ['T'] nucleotide for the guanine ['G'] nucleotide at position 382 of SEQ ID NO:6;

f) insertion of a nucleotide sequence 'TAAA' between position 496 and position 497 of SEQ ID NO:6;

g) insertion of a nucleotide sequence 'AC' between position 596 and 597 of SEQ ID NO:6; and h) any combination of part a), part b), part c), part d), part e), part f), and part g) above.

These examples are not intended to be limiting in nature and will be elaborated below. FIG. 1 graphically illustrates various *Yarrowia* EL1 promoter regions (i.e., SEQ ID NO:6 [857 bp EL1L], SEQ ID NO:8 [857 bp EL1LM]; SEQ ID NO:16 [716 bp EL1LM-P2], SEQ ID NO:27 [361 bp EL1-P4], SEQ ID NO:29 [261 bp EL1-P5], and SEQ ID NO:30 [207 bp minimal/core EL1 promoter]), with the 1000 bp 5' upstream region (SEQ ID NO:2) of the EL1 initiation codon of the *Yarrowia* EL1 gene as a reference.

The term "promoter activity" will refer to an assessment of the transcriptional efficiency of a promoter. This may, for instance, be determined directly by measurement of the amount of mRNA transcription from the promoter (e.g., by quantitative PCR or Northern blotting or primer extension methods) or indirectly by measuring the amount of gene product expressed from the promoter.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "substantial portion" of an amino acid sequence or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993)). In general, a sequence of ten or more contiguous amino acids or thirty or more nucleotides is necessary in order to identify putatively a polypeptide or nucleic acid sequence as homologous to a known protein or gene. Moreover, with respect to nucleotide sequences, gene-specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid molecule comprising the primers. Accordingly, a "substantial portion" of a nucleotide sequence comprises enough of the sequence to specifically identify and/or isolate a nucleic acid molecule comprising the sequence.

Disclosed herein are partial or complete nucleotide sequences containing one or more particular yeast promoters. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the disclosure herein encompasses more than the specific exemplary sequences.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) *Computational Molecular Biology* (Lesk, A. M., Ed.) Oxford University: NY (1988); 2) *Biocomputing: Informatics and Genome Projects* (Smith, D. W., Ed.) Academic: NY (1993); 3) *Computer Analysis of Sequence Data, Part I* (Griffin, A. M., and Griffin, H. G., Eds.) Humania: NJ (1994); 4) *Sequence Analysis in Molecular Biology* (von Heinje, G., Ed.) Academic (1987); and, 5) *Sequence Analysis Primer* (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, *CABIOS*, 5:151-153 (1989); Higgins, D. G. et al., *Comput. Appl. Biosci.*, 8:189-191 (1992)) and found in the MegAlign™ (version 8.0.2) program of the LASERGENE bioinformatics computing suite (DNASTAR Inc.). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs (%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides from other species, wherein such polypeptides have the same or similar function or activity. Likewise, suitable promoter regions (isolated polynucleotides of the present invention) are at least about 70-85% identical, and more preferably at least about 85-95% identical to the nucleotide sequences reported herein. Although preferred ranges are described above, useful examples of percent identities include any integer percentage from 70% to 100%, such as 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable *Yarrowia* EL1 promoter regions not only have the above homologies but typically are at least 50 nucleotides in length, more preferably at least 100 nucleotides in length, more preferably at least 250 nucleotides in length, and more preferably at least 500 nucleotides in length.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for *Yarrowia lipolytica* is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. Chimeric genes herein will typically comprise a promoter region of an EL1 *Yarrowia* gene operably linked to a coding region of interest. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence which codes for a specific amino acid sequence. The terms "coding sequence" and "coding region" are used interchangeably herein. A "coding region of interest" is a coding region which is desired to be expressed. Such coding regions are discussed more fully hereinbelow. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

"Promoter" refers to a DNA sequence that facilitates transcription of a coding sequence, thereby enabling gene expression. In general, a promoter is typically located on the same strand and upstream of the coding sequence (i.e., 5' of the coding sequence). Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

"Minimal promoter" refers to the minimal length of DNA sequence that is necessary to initiate basal level transcription of an operably linked coding sequence. The "minimal promoter" usually does not include the untranslated region located between transcription start site and translation start site. Although promoters often interact with the TATA binding protein ["TBP"] to create a transcription initiation complex from which RNA polymerase II transcribes the DNA coding sequence, only some promoters contain a TATA box to which TBP binds directly. In yeast, the TATA-box is usually located about 20 to 130 bp upstream of the transcription start site. For those TATA-less promoters, it is thought that transcription factor TFIID coordinates delivery of TBP and functions largely to stabilize TBP binding in lieu of a TATA box (Basehoar et al., *Cell*, 116:699-709 (2004)). Some TATA-less promoters contain an "initiator" element [Zhang, Z., and Dietrich, F.S., *Nucleic Acids Res.*, 33:2838-2851 (2005), incorporated herein by reference] located around the transcription start site, which can direct basal level transcription.

Thus, the minimal promoter region for the EL1 TATA-less promoters is herein defined as the −255 to −48 region upstream of the EL1 gene (i.e., as set forth in SEQ ID NO:30), which contains initiator elements sufficient to initiate basal level transcription of an operably linked coding sequence.

Alternately, the −255 to −1 region will also be a useful minimal promoter region (SEQ ID NO:32).

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

The term "enhancer" refers to a cis-regulatory sequence that can elevate levels of transcription from an adjacent eukaryotic promoter, thereby increasing transcription of the gene. Enhancers can act on promoters over many kilobases of DNA and can be 5' or 3' to the promoter they regulate. Enhancers can also be located within introns (Giacopelli F. et al., *Gene Expr.*, 11:95-104 (2003)).

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic" or "recombinant" or "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant construct may comprise one or more expression cassettes. In another example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.*, 4:2411-2418 (1985); De Almeida et al., *Mol. Gen. Genetics*, 218:78-86 (1989)), and thus that multiple events must be screened in order to obtain strains displaying the desired expression level and pattern. Such screening may be accomplished by Southern analysis of DNA, Northern analysis of mRNA expression, Western and/or Elisa analyses of protein expression, formation of a specific product, phenotypic analysis or GC analysis of the PUFA products, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.*, 215:403-410 (1990)); 3) DNASTAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Cold Spring Harbor, N.Y. (1989); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

Esterases and lipases include those enzymes that catalyze the hydrolysis of ester bonds in water-insoluble, lipid substrates. Within *Yarrowia lipolytica*, a gene encoding a hypothetical protein weakly homologous to esterase/lipase has been identified (SEQ ID NO:1, "YALI0E19899g" locus, Dujon, B. et al., *Nature*, 430(6995):35-44 (2004)).

*Yarrowia* mutants having their native snf1 gene knocked-out can constitutively accumulate high levels of oil, even in nitrogenous growth media, when compared to the wild-type strains (U.S. Pat. Appl. Publ. No. 2010-0062502-A1). The snf1 gene encodes the alpha subunit of the SNF1 protein kinase, a heterotrimeric serine/threonine protein kinase that appears to function as a global regulator of gene expression. Particularly, SNF1 protein kinase regulates the transcription of numerous glucose-repressed genes, with a significant portion of those genes functioning in transcription and signal transduction. In general, when the heterotrimeric kinase is activated by phosphorylation, for example, in response to glucose limitation, ATP-producing catabolic pathways increase.

Based on microarray analysis in *Y. lipolytica*, it has been determined that over 200 genes are differentially expressed by more than 1.3-fold in snf1 knock-out strains, when compared to their expression in control strains (U.S. Pat. Appl. Publ. No. 2010-0062502-A1, Example 11 therein). Interestingly, the transcription of EL1 in these snf1 knock-out strains was increased as much as 2.93 times that of the wildtype strains.

Based on the above, the EL1 gene was identified as a potential source of new and improved yeast promoters for metabolic engineering of yeast and for controlling heterologous genes in yeast. In order to understand the means by which EL1 expression is regulated in *Yarrowia*, the EL1 promoter was isolated and its functional structure was mechanistically analyzed.

In general, a promoter useful for controlling the expression of heterologous genes in yeast should preferably meet criteria with respect to strength, activities, pH tolerance and inducibility, as described in U.S. Pat. No. 7,259,255. Additionally, today's complex metabolic engineering utilized for construction of yeast having the capability to produce a variety of heterologous polypeptides in commercial quantities requires a suite of promoters that are regulatable under a variety of natural growth and induction conditions.

Thus, described herein are a suite of promoter regions of an EL1 *Yarrowia* gene, useful for driving expression of any suitable coding region of interest in a transformed yeast cell. More specifically, described herein is an isolated nucleic acid molecule comprising a promoter region of an EL1 *Yarrowia* gene, wherein said promoter region of an EL1 *Yarrowia* gene is set forth in SEQ ID NO:6 (corresponding to the 5' upstream −857 to −1 region of SEQ ID NO:1), and wherein said promoter optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;

b) substitution of an adenine ['A'] nucleotide for the cytosine ['C'] nucleotide at position 856 of SEQ ID NO:6;

c) substitution of a thymine ['T'] nucleotide or a guanine ['G'] nucleotide for the cytosine ['C'] nucleotide at position 856 of SEQ ID NO:6;

d) substitution of a cytosine ['C'] nucleotide for the guanine ['G'] nucleotide at position 382 of SEQ ID NO:6 e) substitution of an adenine ['A'] nucleotide or a thymine ['T'] nucleotide for the guanine ['G'] nucleotide at position 382 of SEQ ID NO:6;

f) insertion of a nucleotide sequence 'TAAA' between position 496 and position 497 of SEQ ID NO:6;

g) insertion of a nucleotides sequence 'AC' between position 596 and 597 of SEQ ID NO:6; and, h) any combination of part a), part b), part c), part d), part e), part f), and part g) above.

In some embodiments, the promoter region of an EL1 Yarrowia gene is selected from the group consisting of SEQ ID NOs:2, 6, 8, 16, 21, 25, 27, and 29. These promoter regions are preferred to provide relatively high levels of inducible promoter activity when operably linked to a coding region of interest.

The relationship between the promoter regions of a Yarrowia EL1 gene selected from the group consisting of SEQ ID NOs:2, 6, 8, 21, 25, 16, 27, 29, and 30, supra, is readily observed upon alignment of the individual promoter sequences. Specifically, FIG. 2 (comprising FIGS. 2A, 2B, 2C, 2D, and 2E) provides an alignment of:

(a) the 1000 bp promoter region EL1F (SEQ ID NO:2);

(b) the 857 bp promoter region EL1L (SEQ ID NO:6);

(c) the 720 bp promoter region EL1LM-P2P1 (SEQ ID NO:21);

(d) the 718 bp promoter region EL1LM-P2P2 (SEQ ID NO:25);

(e) the 716 bp promoter region EL1LM-P2 (SEQ ID NO:16);

(f) the 361 bp promoter region EL1-P4 (SEQ ID NO:27);

(g) the 261 bp promoter region EL1-P5 (SEQ ID NO:29); and, (h) the 207 bp promoter region EL1 minimal promoter (SEQ ID NO:30);

Nucleotide differences are highlighted with a box and an arrow.

As will be obvious to one of skill in the art, the above discussion is by no means limiting to the description of suitable promoter regions of an EL1 Yarrowia gene. For example, alternate Yarrowia EL1 promoter regions may be longer than the 1000 bp sequence 5' upstream of the nucleotide 'A' (designated as +1) of the translation initiation codon 'ATG' of SEQ ID NO:1, thereby encompassing additional nucleotides.

Similarly, it should be recognized that promoter fragments of various diminishing lengths may have identical promoter activity, since the exact boundaries of the regulatory sequences have not been completely defined. Thus, for example, it is also contemplated that a suitable promoter region of an EL1 Yarrowia gene could also include a promoter region of SEQ ID NO:6, wherein the 5'-terminus deletion was greater than 596 consecutive nucleotides.

More specifically, based on sequence analysis of the promoter region set forth in SEQ ID NO:29, and identification of six possible transcription initiator elements upstream of the ATG translation initiation codon, it is hypothesized herein that the minimal promoter region that could function for basal level transcription initiation of an operably linked coding region of interest encompasses (at least) the 207 bp 5' upstream untranslated region from the 'ATG' translation initiation codon of an EL1 Yarrowia gene comprising the −255 to −48 region of SEQ ID NO:1; this 207 bp region is set forth independently as SEQ ID NO:30.

In alternate embodiments, SEQ ID NO:30 could be utilized as a minimal promoter to fuse with enhancers to drive expression of a coding region of interest. One of skill in the art would readily be able to conduct appropriate deletion studies to determine the appropriate length of a promoter region of an EL1 Yarrowia gene required to enable the desired level of promoter activity.

In alternate embodiments, SEQ ID NO:33 could be used as an enhancer to elevate levels of transcription from an adjacent eukaryotic coding region of interest, or fuse with a minimal promoter to form a recombinant promoter to drive expression of a coding region of interest. One of skill in the art would readily be able to conduct appropriate deletion studies to determine the minimal length of the enhancer region (SEQ ID NO:33) to enable the desired level of promoter activity.

Thus, in alternate embodiments, described herein is an isolated nucleic acid molecule comprising a promoter region of an EL1 Yarrowia gene, wherein said isolated nucleic acid molecule is selected from the group consisting of SEQ ID NO:6, SEQ ID NO:8, SEQ ID NO:16, SEQ ID NO:21, SEQ ID NO:25, SEQ ID NO:27, SEQ ID NO:29, and SEQ ID NO:32.

More specifically, additional variant Yarrowia EL1 promoter regions may be constructed, wherein the DNA sequence of the promoter has one or more nucleotide substitutions (i.e., deletions, insertions, substitutions, or addition of one or more nucleotides in the sequence) which do not affect (in particular, impair) the yeast promoter activity. Regions that can be modified without significantly affecting the yeast promoter activity can be identified by deletion studies. A variant promoter of the present invention has at least about 10%, more preferably at least about 20%, more preferably at least about 40%, more preferably at least about 60%, more preferably at least about 80%, more preferably at least about 90%, more preferably at least about 100%, more preferably at least about 200%, more preferably at least about 300% and most preferably at least about 500% of the promoter activity of any of the Yarrowia EL1 promoter regions described herein as SEQ ID NO:6, SEQ ID NO:8, SEQ ID NO:16, SEQ ID NO:21, SEQ ID NO:25, SEQ ID NO:27, and SEQ ID NO:29.

U.S. Pat. No. 7,259,255 describes a variety of methods for mutagenesis suitable for the generation of mutant promoters. This would permit production of a putative promoter having, for example, a more desirable level of promoter activity in the host cell or a more desirable sequence for purposes of cloning (e.g., removal of a restriction enzyme site within the native promoter region). Similarly, the cited reference also discusses means to examine regions of a nucleotide of interest important for promoter activity (i.e., functional analysis via deletion mutagenesis to determine the minimum portion of the putative promoter necessary for activity).

All variant promoter regions of an EL1 Yarrowia gene, derived from the promoter regions described herein, are within the scope of the present disclosure.

Similarly, it should be noted that one could isolate regions upstream of the EL1 initiation codon in various Yarrowia species and strains, other than the region isolated herein from Yarrowia lipolytica ATCC #20362, and thereby identify alternate promoter regions of an EL1 Yarrowia gene. As is well known in the art, isolation of homologous promoter regions or genes using sequence-dependent protocols is readily possible using various techniques (see, U.S. Pat. No. 7,259,255). Examples of sequence-dependent protocols useful to isolate homologous promoter regions include, but are not limited to: 1) methods of nucleic acid hybridization; 2) methods of DNA and RNA amplification, as exemplified by various uses of nucleic acid amplification technologies [e.g., polymerase chain reaction ["PCR"], Mullis et al., U.S. Pat. No. 4,683, 202; ligase chain reaction ["LCR"], Tabor, S. et al., *Proc. Acad. Sci. U.S.A.*, 82:1074 (1985); or strand displacement amplification (SDA), Walker, et al., *Proc. Natl. Acad. Sci.*

U.S.A., 89:392 (1992)]; 3) methods of library construction and screening by complementation; and, 4) methods of genome sequencing. Based on sequence conservation between related organisms, one would expect that the promoter regions would likely share significant homology (i.e., at least about 70-85% identity, more preferably at least about 85-90% identity and more preferably at least about 90-95% identity); however, one or more differences in nucleotide sequence could be observed when aligned with promoter regions of comparable length derived from the upstream region of SEQ ID NO:2. For example, one of skill in the art could readily isolate the Yarrowia EL1 promoter region from any of the various Y. lipolytica strains available through the American Type Culture Collection ["ATCC"], including, for example #8661, #8662, #9773, #15586, #16617, #16618, #18942, #18943, #18944, #18945, #20114, #20177, #20182, #20225, #20226, #20228, #20327, #20255, #20287, #20297, #20315, #20320, #20324, #20336, #20341, #20346, #20348, #20363, #20364, #20372, #20373, #20383, #20390, #20400, #20460, #20461, #20462, #20496, #20510, #20628, #20688, #20774, #20775, #20776, #20777, #20778, #20779, #20780, #20781, #20794, #20795, #20875, #20241, #20422, #20423, #32338, #32339, #32340, #32341, #34342, #32343, #32935, #34017, #34018, #34088, #34922, #34922, #38295, #42281, #44601, #46025, #46026, #46027, #46028, #46067, #46068, #46069, #46070, #46330, #46482, #46483, #46484, #46436, #60594, #62385, #64042, #74234, #76598, #76861, #76862, #76982, #90716, #90811, #90812, #90813, #90814, #90903, #90904, #90905, #96028, #201241, #201242, #201243, #201244, #201245, #201246, #201247, #201249, or #201847. Similarly, the following strains of Yarrowia lipolytica could be obtained from the Herman J. Phaff Yeast Culture Collection, University of California Davis (Davis, Calif.): Y. lipolytica 49-14, Y. lipolytica 49-49, Y. lipolytica 50-140, Y. lipolytica 50-46, Y. lipolytica 50-47, Y. lipolytica 51-30, Y. lipolytica 60-26, Y. lipolytica 70-17, Y. lipolytica 70-18, Y. lipolytica 70-19, Y. lipolytica 70-20, Y. lipolytica 74-78, Y. lipolytica 74-87, Y. lipolytica 74-88, Y. lipolytica 74-89, Y. lipolytica 76-72, Y. lipolytica 76-93, Y. lipolytica 77-12T and Y. lipolytica 77-17. Or, strains could be obtained from the Laboratoire de Microbiologie et Génétique Moléculaire of Dr. Jean-Marc Nicaud, INRA Centre de Grignon, France, including for example, Yarrowia lipolytica JMY798 (Mlíčková, K. et al., Appl. Environ. Microbiol. 70(7):3918-24 (2004)), Y. lipolytica JMY399 (Barth, G., and C. Gaillardin. In, Nonconventional Yeasts In Biotechnology; Wolf, W. K., Ed.; Springer-Verlag: Berlin, Germany, 1996; pp 313-388) and Y. lipolytica JMY154 (Wang, H. J., et al., J. Bacteriol. 181(17):5140-8 (1999)).

In general, microbial expression systems and expression vectors containing regulatory sequences that direct high level expression of foreign proteins are well known to those skilled in the art. Any of these could be used to construct chimeric genes, which could then be introduced into appropriate microorganisms via transformation to provide high-level expression of the encoded enzymes.

Vectors (e.g., constructs, plasmids) and DNA expression cassettes useful for the transformation of suitable microbial host cells are well known in the art. The specific choice of sequences present in the construct is dependent upon the desired expression products, the nature of the host cell and the proposed means of separating transformed cells versus non-transformed cells. Typically, however, the vector contains at least one expression cassette, a selectable marker and sequences allowing autonomous replication or chromosomal integration. Suitable expression cassettes comprise a region 5' of the gene that controls transcription (e.g., a promoter), the gene coding sequence, and a region 3' of the DNA fragment that controls transcriptional termination, i.e., a terminator. It is most preferred when both control regions are derived from genes from the transformed yeast cell, although they need not be derived from genes native to the host.

Herein, transcriptional control regions (also initiation control regions or promoters) that are useful to drive expression of a coding gene of interest in the desired yeast cell are those promoter regions of an EL1 Yarrowia gene, as described supra. Once the promoter regions are identified and isolated, they may be operably linked to a coding region of interest to create a chimeric gene. The chimeric gene may then be expressed in a suitable expression vector in transformed yeast cells, particularly in the cells of oleaginous yeast (e.g., Yarrowia lipolytica).

Coding regions of interest to be expressed in transformed yeast cells may be either endogenous to the host or heterologous. Genes encoding proteins of commercial value are particularly suitable for expression. For example, suitable coding regions of interest may include (but are not limited to) those encoding viral, bacterial, fungal, plant, insect, or vertebrate coding regions of interest, including mammalian polypeptides. Further, these coding regions of interest may be, for example, structural proteins, signal transduction proteins, transcription factors, enzymes (e.g., oxidoreductases, transferases, hydrolyases, lyases, isomerases, ligases), or peptides. A non-limiting list includes genes encoding enzymes such as acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-glucanases, beta-galactosidases, glucoamylases, alpha-glucosidases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases or xylanases.

Thus, one aspect of the present disclosure provides a recombinant construct comprising a Yarrowia EL1 promoter region, as well as recombinant expression vectors comprising the recombinant construct. The EL1 promoter may also be comprised within a chimeric gene.

Also provided herein is a method for the expression of a coding region of interest in a transformed yeast cell comprising:
a) providing a transformed yeast cell having a recombinant construct, wherein the recombinant construct comprises:
(1) a promoter region of an EL1 Yarrowia gene; and
(2) a coding region of interest which is expressible in the yeast cell;
wherein the promoter region is operably linked to the coding region of interest; and
b) growing the transformed yeast cell of step (a) under conditions whereby the recombinant construct is expressed.

The polypeptide so produced by expression of the recombinant construct may optionally be recovered from the culture.

In some embodiments herein, preferred coding regions of interest are those encoding enzymes involved in the production of microbial oils, including omega-6 and omega-3 fatty acids (i.e., omega-6 and omega-3 fatty acid biosynthetic pathway enzymes). Thus, preferred coding regions include those encoding desaturases (e.g., delta-8 desaturases, delta-5 desaturases, delta-17 desaturases, delta-12 desaturases, delta-4 desaturases, delta-6 desaturases, delta-15 desaturases and delta-9 desaturases) and elongases (e.g., $C_{14/16}$ elongases, $C_{16/18}$ elongases, $C_{18/20}$ elongases, $C_{20/22}$ elongases, delta-6 elongases and delta-9 elongases).

More specifically, the omega-3/omega-6 fatty acid biosynthetic pathway is illustrated in FIG. 3. All pathways require the initial conversion of oleic acid [18:1] to linoleic acid ["LA"; 18:2], the first of the omega-6 fatty acids, by a delta-12 desaturase. Then, using the "delta-9 elongase/delta-8 desaturase pathway" and LA as substrate, long-chain omega-6 fatty acids are formed as follows: 1) LA is converted to eicosadienoic acid ["EDA"; 20:2] bp a delta-9 elongase; 2) EDA is converted to dihomo-gamma-linolenic acid ["DGLA"; 20:3] bp a delta-8 desaturase; 3) DGLA is converted to arachidonic acid ["ARA"; 20:4] bp a delta-5 desaturase; 4) ARA is converted to docosatetraenoic acid ["DTA"; 22:4] bp a $C_{20/22}$ elongase; and, 5) DTA is converted to docosapentaenoic acid ["DPAn-6"; 22:5] by a delta-4 desaturase. To clarify, "omega-6 fatty acids" are polyunsaturated fatty acids having the first unsaturated double bond six carbon atoms from the omega (methyl) end of the molecule and additionally having a total of two or more double bonds, with each subsequent unsaturation occurring 3 additional carbon atoms toward the carboxyl end of the molecule.

The "delta-9 elongase/delta-8 desaturase pathway" can also use alpha-linolenic acid ["ALA"; 18:3] as substrate to produce long-chain omega-3 fatty acids as follows: 1) LA is converted to ALA, the first of the omega-3 fatty acids, by a delta-15 desaturase; 2) ALA is converted to eicosatrienoic acid ["ETrA"; 20:3] bp a delta-9 elongase; 3) ETrA is converted to eicosatetraenoic acid ["ETA"; 20:4] bp a delta-8 desaturase; 4) ETA is converted to eicosapentaenoic acid ["EPA"; 20:5] bp a delta-5 desaturase; 5) EPA is converted to docosapentaenoic acid ["DPA"; 22:5] bp a $C_{20/22}$ elongase; and, 6) DPA is converted to docosahexaenoic acid ["DHA"; 22:6] bp a delta-4 desaturase. Optionally, omega-6 fatty acids may be converted to omega-3 fatty acids. For example, ETA and EPA are produced from DGLA and ARA, respectively, by delta-17 desaturase activity. To clarify, "omega-3 fatty acids" are polyunsaturated fatty acids having the first unsaturated double bond three carbon atoms away from the omega end of the molecule and additionally having a total of three or more double bonds, with each subsequent unsaturation occurring 3 additional carbon atoms toward the carboxyl end of the molecule.

Alternate pathways for the biosynthesis of omega-3/omega-6 fatty acids utilize a delta-6 desaturase and $C_{18/20}$ elongase, that is, the "delta-6 desaturase/delta-6 elongase pathway". More specifically, LA and ALA may be converted to GLA and stearidonic acid ["STA"; 18:4], respectively, by a delta-6 desaturase; then, a $C_{18/20}$ elongase converts GLA to DGLA and/or STA to ETA. Downstream PUFAs are subsequently formed as described above.

One of skill in the art will appreciate that the disclosure herein also provides a method for the production of an omega-3 fatty acid or omega-6 fatty acid comprising:
  a) providing a transformed oleaginous yeast comprising a recombinant construct, wherein the recombinant construct comprises:
    i) a promoter region of an EL1 *Yarrowia* gene; and
    ii) a coding region encoding at least one omega-3 fatty acid or omega-6 fatty acid biosynthetic pathway enzyme;
    wherein the promoter region and the coding region are operably linked; and
  b) growing the transformed oleaginous yeast of step (a) under conditions whereby the at least one omega-3 fatty acid or omega-6 fatty acid biosynthetic pathway enzyme is expressed and the omega-3 fatty acid or the omega-6 fatty acid is produced; and
  c) optionally recovering the omega-3 fatty acid or the omega-6 fatty acid.

The omega-3 fatty acid or the omega-6 fatty acid may be selected from the group consisting of: LA, GLA, EDA, DGLA, ARA, DTA, DPAn-6, ALA, STA, ETrA, ETA, EPA, DPAn-3 and DHA.

Once a DNA cassette (e.g., comprising a chimeric gene comprising a promoter region of an EL1 *Yarrowia* gene, ORF and terminator) suitable for expression in a yeast cell has been obtained, it is placed in a plasmid vector capable of autonomous replication in the yeast cell, or it is directly integrated into the genome of the yeast cell. Integration of expression cassettes can occur randomly within the yeast genome or can be targeted through the use of constructs containing regions of homology with the yeast genome sufficient to target recombination to a specific locus. All or some of the transcriptional and translational regulatory regions can be provided by the endogenous locus where constructs are targeted to an endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced chimeric genes are expressed at the necessary levels to provide for synthesis of the desired products.

U.S. Pat. No. 7,259,255 describes means to increase expression of a particular coding region of interest.

Constructs comprising the chimeric gene(s) of interest may be introduced into a yeast cell by any standard technique. These techniques include transformation (e.g., lithium acetate transformation [*Methods in Enzymology*, 194:186-187 (1991)]), protoplast transformation, bolistic impact, electroporation, microinjection, or any other method that introduces the chimeric gene(s) of interest into the yeast cell.

For convenience, a yeast cell that has been manipulated by any method to take up a DNA sequence, for example, in an expression cassette, is referred to herein as "transformed", "transformant" or "recombinant" (as these terms will be used interchangeably herein). The transformed yeast will have at least one copy of the expression construct and may have two or more, depending upon whether the expression cassette is integrated into the genome or is present on an extrachromosomal element having multiple copy numbers.

The transformed yeast cell can be identified by various selection techniques, as described in U.S. Pat. Nos. 7,238,482, 7,259,255 and 7,932,077.

Following transformation, substrates upon which the translated products of the chimeric genes act may be produced by the yeast either naturally or transgenically, or they may be provided exogenously.

Yeast cells for expression of the instant chimeric genes comprising a promoter region of an EL1 *Yarrowia* gene may include yeast that grow on a variety of feedstocks, including simple or complex carbohydrates, fatty acids, organic acids, oils, glycerol and alcohols, and/or hydrocarbons over a wide range of temperature and pH values. It is contemplated that because transcription, translation and the protein biosynthetic apparatus are highly conserved, any yeast will be a suitable host for expression of the present chimeric genes.

As previously noted, yeast do not form a specific taxonomic or phylogenetic grouping, but instead comprise a diverse assemblage of unicellular organisms that occur in the Ascomycotina and Basidiomycotina, most of which reproduce by budding (or fission) and derive energy via fermentation processes. Examples of some yeast genera include, but are not limited to: *Agaricostilbum, Ambrosiozyma, Arthroascus, Arxula, Ashbya, Babjevia, Bensingtonia, Botryozyma, Brettanomyces, Bullera, Candida, Clavispora, Cryptococcus, Cystofilobasidium, Debaryomyces, Dekkera, Dipodascus, Endomyces, Endomycopsella, Erythrobasidium, Fellomyces, Filobasidium, Galactomyces, Geotrichum, Guilliermondella, Hansenula, Hanseniaspora, Kazachstania, Kloeckera, Kluyveromyces, Kockovaella, Kodamaea, Komagataella, Kondoa, Lachancea, Leucosporidium, Leucosporidiella, Lipomyces, Lodderomyces, Issatchenkia, Magnusiomyces, Mastigobasidium, Metschnikowia, Monosporella, Myxozyma, Nadsonia, Nematospora, Oosporidium, Pachysolen, Pichia, Phaffia, Pseudozyma, Reniforma, Rhodosporidium, Rhodotorula, Saccharomyces, Saccharomycodes, Saccharomycopsis, Saturnispora, Schizoblastosporion, Schizosaccharomyces, Sirobasidium, Smithiozyma, Sporobolomyces, Sporopachydermia, Starmerella, Sympodiomycopsis, Sympodiomyces, Torulaspora, Tremella, Trichosporon, Trichosporiella, Trigonopsis, Udeniomyces, Wickerhamomyces, Williopsis, Xanthophyllomyces, Yarrowia, Zygosaccharomyces, Zygotorulaspora, Zymoxenogloea* and *Zygozyma*.

In preferred embodiments, the transformed yeast is an oleaginous yeast. These organisms are naturally capable of oil synthesis and accumulation, wherein the oil can comprise greater than about 25% of the dry cell weight, more preferably greater than about 30% of the dry cell weight, more preferably greater than about 40% of the dry cell weight, more preferably greater than about 50% of the dry cell weight, and most preferably greater than about 60% of the dry cell weight. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis,* and *Yarrowia lipolytica* (formerly classified as *Candida lipolytica*). Alternately, oil biosynthesis may be genetically engineered such that the transformed yeast can produce more than 25% oil of the dry cell weight, and thereby be considered oleaginous.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)). The *Y. lipolytica* strain designated as ATCC #20362 was the particular strain from which the EL1 *Yarrowia* gene and promoter regions encompassed within SEQ ID NO:2 were isolated.

Specific teachings applicable for transformation of oleaginous yeasts (i.e., *Yarrowia lipolytica*) via integration techniques based on linearized fragments of DNA include U.S. Pat. Nos. 4,880,741 and 5,071,764 and Chen, D. C. et al. (*Appl. Microbiol. Biotechnol.*, 48(2):232-235 (1997)). Specific teachings applicable for expression of omega-3 fatty acid or omega-6 fatty acid biosynthetic pathway enzymes in the oleaginous yeast *Y. lipolytica* are described in U.S. Pat. Nos. 7,238,482, 7,550,286, 7,588,931, 7,932,077, U.S. Pat. Appl. Publ. No. 2009-0093543-A1, and U.S. Pat. Appl. Publ. No. 2010-0317072-A1, each incorporated herein by reference in their entirety.

The transformed yeast cell is grown under conditions that optimize expression of the chimeric gene(s). In general, media conditions may be optimized by modifying the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media suitable for the transformed yeast described herein should contain a suitable carbon source. Suitable carbon sources may include, but are not limited to: monosaccharides, disaccharides, oligosaccharides, polysaccharides, sugar alcohols, mixtures from renewable feedstocks, alkanes, fatty acids, esters of fatty acids, glycerol, monoglycerides, diglycerides, triglycerides, phospholipids, various commercial sources of fatty acids, and one-carbon sources, such as are described in U.S. Pat. No. 7,259,255. Hence it is contemplated that the source of carbon utilized may encompass a wide variety of carbon-containing sources and will only be limited by the choice of the yeast species. Although all of the above mentioned carbon sources and mixtures thereof are expected to be suitable herein, preferred carbon sources are sugars (e.g., glucose, invert sucrose, sucrose, fructose and combinations thereof), glycerols, and/or fatty acids (see U.S. Pat. Appl. Publ. No. 2011-0059204 A1).

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the transformed yeast (and optionally, promotion of the enzymatic pathways necessary for omega-3/omega-6 fatty acid production). Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and transformed yeast cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of omega-3/omega-6 fatty acids in oleaginous yeast cells requires a two-stage process, since the metabolic state must be "balanced" between growth and synthesis/storage of fats. Thus, most preferably, a two-stage fermentation process is necessary for the production of omega-3/omega-6 fatty acids in oleaginous yeast (e.g., *Yarrowia lipolytica*). This approach is described in U.S. Pat. No. 7,238,482.

Host cells comprising a suitable coding region of interest operably linked to promoter regions of an EL1 *Yarrowia* gene may be cultured using methods known in the art. For example, the cell may be cultivated by shake flask cultivation or small-/large-scale fermentation in laboratory or industrial fermentors performed in a suitable medium and under conditions allowing expression of the coding region of interest. Similarly, where commercial production of a product that relies on the instant genetic chimera is desired, a variety of culture methodologies may be applied. For example, large-scale production of a specific gene product over-expressed from a recombinant host may be produced by a batch, fed-batch or continuous fermentation process (see U.S. Pat. No. 7,259, 255).

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and 3) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), New England Biolabs (Ipswich, Mass.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature for Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of Yarrowia lipolytica:

*Y. lipolytica* strains with ATCC Accession Nos. #20362, #76982 and #90812 were purchased from the American Type Culture Collection (Rockville, Md.). *Y. lipolytica* strains were typically grown at 28-30° C. Agar plates were prepared as required by addition of 20 g/L agar to the liquid media, according to standard methodology.

Example 1

Isolation of the 5' Upstream Regions of the EL1 Gene from *Yarrowia lipolytica*

According to the DNA sequence of the *Yarrowia* EL1 locus (ORF "YALI0E19899g", Dujon, B. et al., *Nature,* 430(6995): 35-44 (2004), SEQ ID NO:1 herein), the 1 kB length sequence 5' upstream of the nucleotide 'A' (designated as +1) of the translation initiation codon 'ATG' was assumed to encode the promoter region (designated herein as EL1F, SEQ ID NO:2).

In order to study the promoter region upstream of the EL1 gene, oligonucleotides Y1210 (SEQ ID NO:3) and Y1211 (SEQ ID NO:4) were designed as primers to amplify a 857 bp 5' upstream fragment from the nucleotide 'A' of the translation initiation codon 'ATG' of the EL1 gene. A ClaI site was included at the 5' portion of oligonucleotide Y1210 (SEQ ID NO:3). In order to incorporate a *Yarrowia* translation initiation site consensus sequence (i.e., ACC<u>ATG</u>G, U.S. Pat. No. 7,125,672) around the start codon 'ATG', the adenine nucleotide ["A"] at position −2 of the EL1 gene was mutated to a cytosine ["C"] in oligonucleotide Y1211 (SEQ ID NO:4)

The 857 bp 5' upstream fragment of the EL1 gene was amplified using *Y. lipolytica* strain ATCC #20362 genomic DNA as template and oligonucleotides YL1210 and YL1211 as primers. The PCR amplification was carried out in a 50 µl total volume comprising: PCR buffer (containing 10 mM KCl, 10 mM $(NH_4)_2SO_4$, 20 mM Tris-HCl (pH 8.75), 2 mM $MgSO_4$, 0.1% Triton X-100), 100 µg/mL BSA (final concentration), 200 µM each deoxyribonucleotide triphosphate, 10 pmole of each primer and 1 µl of Pfu DNA polymerase (Stratagene, San Diego, Calif.)). The thermocycler conditions were set for 35 cycles at 95° C. for 1 min, 56° C. for 30 sec, and 72° C. for 1 min, followed by a final extension at 72° C. for 10 min.

The PCR product comprising the 857 bp 5' upstream fragment of the EL1 gene was purified using a Qiagen PCR purification kit, followed by gel electrophoresis in 1% (weight/volume) agarose. The product was then cloned into the pCR4TOPO vector (Invitrogen, San Diego, Calif.). The ligated DNA sample was used to transform *E. coli* DH5α cells individually, and transformants were selected on LB agar containing ampicillin (100 µg/mL).

Analyses of the plasmid DNA from transformants confirmed the presence of an 857 bp fragment. The plasmid containing the 857 bp DNA fragment was designated pT-EL1 (SEQ ID NO:5). Sequence analyses showed that pT-EL1 contained a fragment of 857 bp (designated as EL1L, wherein the "L" is for "long"; SEQ ID NO:6) 5' upstream sequence of the EL1 gene, with one nucleotide change at position −2 ("A" to "C") as designed. The fragment was flanked by PmeI (from the vector) and NcoI restriction enzyme sites.

Example 2

Modifications to EL1L: Synthesis of Promoter 857 bp EL1LM

The present Example describes the synthesis of pT-EL1-(S) and pT-EL1-(S)P2 plasmids, each comprising a modified EL1L promoter based on removal or insertion of a specific restriction enzyme site, respectively.

Specifically, plasmid pT-EL1-(S) (SEQ ID NO:7) was generated by site-directed mutagenesis using plasmid pT-EL1 (Example 1) as template, and oligonucleotides Y1212 (SEQ ID NO:9) and Y1213 (SEQ ID NO:10) as primers. The internal SphI site (i.e., 'GCATGC' at nucleotides 421 to 426 of SEQ ID NO:6) of the EL1L promoter was mutated into 'GGATCC' in plasmid pT-EL1-(S) (SEQ ID NO:7). The modified EL1L promoter lacking the internal SphI site within plasmid pT-EL1 was designated as 857 bp EL1LM (wherein the "LM" is for "long, modified"; SEQ ID NO:8).

Plasmid pT-EL1-(S)P2 (SEQ ID NO:11) was generated by site-directed mutagenesis using plasmid pT-EL1-(S) as template, and oligonucleotides Y1242 (SEQ ID NO:12) and Y1243 (SEQ ID NO:13) as primers. Specifically, an internal PmeI site was inserted into the EL1LM promoter at position −593 in pT-EL1-(S)P2 (SEQ ID NO:11). The modified EL1LM promoter comprising the new PmeI site within plasmid pT-EL1-(S)P2 was designated as 861 bp EL1LM+Pme (SEQ ID NO:31).

Example 3

Synthesis and Transformation of an Expression Plasmid Comprising 857 bp EL1LM Promoter To perform comparative studies investigating the promoter activity of the 857 bp EL1LM promoter, an expression plasmid was created such that the EL1LM promoter was operably linked to a reporter gene (i.e., the *E. coli* gene encoding β-glucuronidase ("GUS"; Jefferson, R. A., *Nature*, 342(6251):837-838 (1989)).

U.S. Pat. No. 7,202,356 describes the synthesis of pDMW212 (FIG. 4A and SEQ ID NO:14 herein), comprising a recombinant FBA::GUS::XPR2 construct. More specifically, this expression cassette comprises an FBA promoter fragment (i.e., 5' upstream untranslated region in front of the 'ATG' translation initiation codon of a fructose-bisphosphate aldolase enzyme [E.C. 4.1.2.13] encoded by the fba1 gene and that is necessary for expression), a GUS reporter gene fragment and an XPR2 terminator fragment (comprising ~100 bp of the 3' region of the *Yarrowia* Xpr gene (GenBank Accession No. M17741)), which are all operably linked to one another.

The PmeI/NcoI fragment of pDMW212 (comprising the FBA promoter within the chimeric FBA::GUS::XPR2 gene) was replaced with the 857 bp EL1LM promoter. Specifically, the PmeI/NcoI fragment of pT-EL1-(S) (Example 2), comprising the 857 bp EL1LM promoter, was ligated with the PmeI/NcoI linearized pDMW212 fragment, thereby creating plasmid pEL1GUS (FIG. 4B; SEQ ID NO:15) comprising a chimeric EL1LM::GUS::XPR2 gene. Thus, pEL1GUS contains the following components:

TABLE 3

Description of Plasmid pEL1GUS

| RE Sites and Nucleotide position in SEQ ID NO: 15 | Description of Fragment aChimeric Gene Components |
|---|---|
| ClaI/SacI (8536-2023) | 857 bp EL1LM::GUS::XPR, comprising: 857 bp EL1LM promoter: 857 bp *Y. lipolytica* EL1LM promoter (SEQ ID NO: 8); GUS: *E. coli* beta-D-glucuronidase (GenBank Accession No. AAA68923); XPR2: ~100 bp of the 3' region of Xpr gene of *Y. lipolytica* (GenBank Accession No. M17741) |
| 3163-2283 | ColE1 plasmid origin of replication |
| 4093-3233 | Ampicillin-resistance gene (Amp$^R$) for selection in *E. coli* |
| EcoRI/SphI (4923-6269) | ARS18: *Y. lipolytica* centromere and autonomously replication sequence 18 (GenBank Accession No. M91600) |
| PmeI/SphI (8514-6269) | Leu2: beta-isopropylmalate dehydrogenase gene of *Y. lipolytica* (GenBank Accession No. M37309) |

*Y. lipolytica* strain Y4001 has been described in U.S. Pat. No. 7,709,239 (Example 3 therein). Strain Y4001, derived from *Y. lipolytica* ATCC #20362, was capable of producing about 17% eicosadienoic acid ["EDA"; 20:2 omega-6] relative to the total lipids. The final genotype of strain Y4001 with respect to wild type *Y. lipolytica* ATCC #20362 was: Leu-, GPD::FmD12::Pex20, EXP1::EgD9e::Lip1, FBAINm::EgD9eS::Lip2 and YAT1::ME3S::Pex16. Abbreviations are as follows: FmD12 is a *Fusarium moniliforme* delta-12 desaturase gene [U.S. Pat. No. 7,504,259]; MES5 is a codon-optimized $C_{16/18}$ elongase gene, derived from *Mortierella alpina* [U.S. Pat. No. 7,470,532]; EgD9e is a *Euglena gracilis* delta-9 elongase gene [U.S. Pat. No. 7,645,604]; and, EgD9eS is a codon-optimized delta-9 elongase gene, derived from *E. gracilis* [U.S. Pat. No. 7,645,604].

Plasmids pEL1GUS and pDMW212 were transformed separately into *Y. lipolytica* strain Y4001 according to the method of Chen, D. C. et al. (*Appl. Microbiol Biotechnol.*, 48(2):232-235 (1997)) and as described in U.S. Pat. No. 7,709,239.

Transformed cells were plated onto Minimal Media ["MM"] plates lacking leucine and maintained at 30° C. for 2 to 3 days (MM comprises per liter: 20 g glucose, 1.7 g yeast nitrogen base without amino acids, 1.0 g proline, and pH 6.1 (do not need to adjust)). Thus, transformants were obtained comprising pEL1GUS and pDMW212 plasmids, respectively.

Example 4

Comparative Analyses of 857 bp EL1LM and FBA Promoter Activities in *Yarrowia lipolytica* Strain Y4001

The promoter activities of the 857 bp EL1LM promoter (SEQ ID NO:8) and FBA promoter were determined in *Yarrowia* transformants containing plasmids pEL1GUS and pDMW212, respectively, based on expression of the GUS reporter gene as measured by histochemical assays (Jefferson, R. A., *Plant Mol. Biol. Reporter*, 5:387-405 (1987)).

Specifically, *Y. lipolytica* transformants containing plasmids pEL1GUS and pDMW212 were grown from single colonies in 3 mL MM at 30° C. for 2 days. Then, 1 mL of cells was collected by centrifugation. The remaining cultures were centrifuged and washed 2 times with High Glucose Media ["HGM"], resuspended in 3 mL each of HGM and allowed to grow at 30° C. for another 5 days (HGM comprises per liter: 80 g glucose, 2.58 g $KH_2PO_4$ and 5.36 g $K_2HPO_4$, pH 7.5 (do not need to adjust)). Cell samples from cultures grown 2 days in MM, as well as cultures grown 2 days in MM and 5 days in HGM were collected by centrifugation, resuspended in 100 μl of histochemical staining buffer, and incubated at 30° C. Staining buffer was prepared by dissolving 5 mg of 5-bromo-4-chloro-3-indolyl glucuronide ["X-Gluc"] in 50 μl dimethyl formamide, followed by the addition of 5 mL 50 mM $NaPO_4$, pH 7.0.

The results (FIG. 5) of histochemical staining showed that the 857 bp EL1LM promoter in construct pEL1GUS was weakly active when the transformed Yarrowia cells were grown in MM media. By contrast, very strong expression was observed in identical Yarrowia strains growing in nitrogen-limited HGM media. As expected, the FBA promoter in construct pDMW212 demonstrated strong constitutive activity when pDMW212-transformed cells were grown in either MM or nitrogen-limited HGM media.

Based on the above results, one of skill in the art will therefore recognize that the EL1LM promoter set forth as SEQ ID NO:8 is a strong inducible promoter useful for expression of heterologous genes in transformed yeast, including Yarrowia. It is to be noted that truncated promoters derived from the EL1LM promoter set forth as SEQ ID NO:8 will comprise an adenine ['A'] to cytosine ['C'] substitution at position 856, which corresponds to position −1 in SEQ ID NO:1 (i.e., when the position corresponding to the 'A' nucleotide of the 'ATG' translation initiation site of the EL1 gene is considered +1), when compared to the wildtype 5' upstream sequence. One of skill in the art will appreciate that a suitable promoter region of an EL1 Yarrowia gene may optionally comprise an adenine ['A'] or a cytosine ['C'] nucleotide at this position; alternately, a modified EL1 promoter may also tolerate substitution of a thymine ['T'] nucleotide or guanine ['G'] nucleotide for the wildtype adenine ['A']. It is also to be noted that SEQ ID NO:8, in comparison to SEQ ID NO:6, comprises a substitution of a cytosine ['C'] nucleotide for a guanine ['G'] nucleotide at position 382. Thus, modified EL1LM promoters may also tolerate substitution of an adenine ['A'] nucleotide or thymine ['T'] nucleotide for the wildtype guanine ['G'] at this position.

Example 5

Synthesis and Transformation of Expression Plasmids pEL1GUS2, pEL1GUS2-P1, pEL1GUS2-P2, pEL1GUS2-P4 and pEL1GUS2-P5 Comprising 716 bp EL1LM-P2, 720 bp EL1LM-P2P1, 718 bp EL1LM-P2P2, 361 bp EL1-P4, and 261 bp EL1-P5 Promoters Comparative studies were performed to investigate the promoter activity of modified EL1 promoters having lengths of 716 bp, 720 bp, 718 bp, 361 bp, or 261 bp. Expression plasmids pEL1GUS2, pEL1GUS2-P1, pEL1GUS2-P2, pEL1GUS2-P4 and pEL1GUS2-P5 were created, respectively, each comprising a modified EL1 promoter operably linked to the GUS reporter gene.

First, the PmeI/NcoI fragment of pDMW212 (comprising the FBA promoter within the chimeric FBA::GUS::XPR2 gene) was replaced with the 716 bp PmeI/NcoI fragment of pT-EL1-(S)P2 (designated EL1LM-P2, SEQ ID NO:16). Specifically, the PmeI/NcoI fragment of pT-EL1-(S)P2 (Example 2), comprising the 716 bp EL1LM-P2 promoter, was ligated with the PmeI/NcoI linearized pDMW212 fragment, thereby creating plasmid pEL1GUS2 (SEQ ID NO:17) comprising a chimeric 716 bp EL1LM-P2::GUS::XPR2 gene.

Second, site-directed mutagenesis was performed using pEL1GUS2 as template and oligonucleotides Y1254 (SEQ ID NO:18) and Y1255 (SEQ ID NO:19) as primers. Specifically, primer Y1254 was designed to insert four nucleotides (i.e., 'TAAA') at position 356 of SEQ ID NO:16, thereby resulting in creation of a PmeI site in the 716 bp EL1LM-P2 promoter in the resultant plasmid, pEL1GUS2-P1 (SEQ ID NO:20). The modified EL1LM-P2 promoter in pEL1GUS2-P1 was 720 bp in length and was designated as 720 bp EL1LM-P2P1 (SEQ ID NO:21).

Similarly, site-directed mutagenesis was performed using pEL1GUS2 as template and oligonucleotides Y1256 (SEQ ID NO:22), and Y1257 (SEQ ID NO:23) as primers. Primer Y1256 was designed to insert two nucleotides (i.e., 'AC') at position 456 of SEQ ID NO:16, thereby resulting in creation of a PmeI site in the 716 bp EL1LM-P2 promoter in the resultant plasmid, pEL1GUS2-P2 (SEQ ID NO:24). The modified EL1LM-P2 promoter in pEL1GUS2-P2 was 718 bp in length and was designated as 718 bp EL1LM-P2P2 (SEQ ID NO:25).

Next, pEL1GUS2-P1 was digested with PmeI and the large PmeI fragment was isolated and then self-ligated to generate plasmid pEL1GUS2-P4 (SEQ ID NO:26) comprising a chimeric EL1-P4::GUS::XPR2 gene, wherein the 361 bp fragment of SEQ ID NO:21 was designated 361 bp EL1-P4 (SEQ ID NO:27). Similarly, pEL1GUS2-P2 was digested with PmeI and the large PmeI fragment was isolated and then self-ligated to generate plasmid pEL1GUS2-P5 (SEQ ID NO:28) comprising a chimeric EL1-P5::GUS::XPR2 gene, wherein the 261 bp fragment of SEQ ID NO:25 was designated 261 bp EL1-P5 (SEQ ID NO:29).

Thus, pEL1GUS2 (SEQ ID NO:17), pEL1GUS2-P1 (SEQ ID NO:20), pEL1GUS2-P2 (SEQ ID NO:24), pEL1GUS2-P4 (SEQ ID NO:26) and pEL1GUS2-P5 (SEQ ID NO:28) are identical expression constructs, with the exception that either a 716 bp EL1LM-P2 (SEQ ID NO:16), 720 bp EL1LM-P2P1 (SEQ ID NO:21), 718 bp EL1LM-P2P2 (SEQ ID NO:25), 361 bp EL1-P4 (SEQ ID NO:27), or 261 bp EL1-P5 (SEQ ID NO:29) promoter derived from the 5' upstream region of the Y. lipolytica EL1 gene was operably linked to the chimeric GUS::XPR2 gene.

Plasmids pEL1GUS, pEL1GUS2, pEL1GUS2-P1, pEL1GUS2-P2, pEL1GUS2-P4, and pEL1GUS2-P5 were transformed separately into Y. lipolytica strain Y4001 as described in Example 3. Transformant cells were plated onto MM plates lacking leucine and maintained at 30° C. for 2 to 3 days. Thus, transformants were obtained comprising the pEL1GUS, pEL1GUS2, pEL1GUS2-P1, pEL1GUS2-P2, pEL1GUS2-P4, and pEL1GUS2-P5 plasmids, respectively.

Example 6

Comparative Analysis of 857 bp EL1LM, 716 bp EL1LM-P2, 720 bp EL1LM-P2P1, 718 bp EL1LM-P2P2, 361 bp EL1-P4, and 261 bp EL1-P5 Promoter Activities in Yarrowia lipolytica Strain Y4001

The promoter activities of the 857 bp EL1LM (SEQ ID NO:8), 716 bp EL1LM-P2 (SEQ ID NO:16), 720 bp EL1LM-P2P1 (SEQ ID NO:21), 718 bp EL1LM-P2P2 (SEQ ID NO:25), 361 bp EL1-P4 (SEQ ID NO:27), and 261 bp EL1-P5 (SEQ ID NO:29) promoters were determined in Yarrowia transformants containing pEL1GUS, pEL1GUS2, pEL1GUS2-P1, pEL1GUS2-P2, pEL1GUS2-P4, and pEL1GUS2-P5, respectively. GUS activity in each expressed construct was measured by histochemical assays as described in Example 4.

The results of histochemical staining showed that the promoter activities of 716 bp EL1LM-P2 (SEQ ID NO:16), 720 bp EL1LM-P2P1 (SEQ ID NO:21), and 718 bp EL1LM-P2P2 (SEQ ID NO:25) were equivalent to the 857 bp EL1LM (SEQ ID NO:8, Example 4). Specifically, each of the three promoters was weakly active when their respective transformed Yarrowia cells were grown in MM, but were very strongly active when their constructs were expressed by cells grown in nitrogen-limited HGM media. This indicated that the activity of the 716 bp EL1LM-P2 promoter (SEQ ID NO:16) was not affected by the 4 bp insertion at position −361 (EL1LM-P2P1, SEQ ID NO:21) or the 2 bp insertion at position −261 (EL1LM-P2P2, SEQ ID NO:25).

The results also showed that the 361 bp EL1-P4 promoter (SEQ ID NO:27) was weakly induced when cells expressing pEL1GUS2-P4 were grown in nitrogen-limited HGM media, which signaled the presence of an enhancer responsible for the induced activity of EL1LM and other modified promoters derived therefrom between positions 141 and 496 of EL1LM (SEQ ID NO:8) (corresponding to positions −716 and −361, respectively, in SEQ ID NO:1, where the 'A' of the ATG start codon is designated as +1). This enhancer is set forth herein as SEQ ID NO:33. The results further showed that the 261 bp EL1-P5 promoter (SEQ ID NO:29) was more strongly induced compared to the 361 bp EL1-P4 promoter (SEQ ID NO:27) when cells expressing pEL1GUS2-P5 were grown in nitrogen-limited HGM media, which indicated the presence of a silencer responsible for the reduced activity of the 361 bp EL1-P4 promoter (SEQ ID NO:27). This silencer is located between positions 496 and 596 of EL1LM (SEQ ID NO:8) (corresponding to positions −361 and −261, respectively, in SEQ ID NO:1, where the 'A' of the ATG start codon is designated as +1).

Based on the above results, one of skill in the art will recognize that the EL1LM promoter set forth as SEQ ID NO:8 can be truncated and retain promoter activity. Deleting the region defined by nucleotide positions 1 to 496 bp of SEQ ID NO:8 resulted in the active mutant promoter described herein as 361 bp EL1-P4, while deleting the region defined by nucleotide positions 1 to 596 bp of SEQ ID NO:8 resulted in the active mutant promoter described herein as 261 bp EL1-P5 (FIG. 1). It is therefore assumed that a variety of modified EL1LM promoters could be utilized for expression of a coding region of interest in a Yarrowia host cell, wherein the promoter optionally comprises at least one modification selected from the group consisting of: a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:8. It is further assumed that SEQ ID NO:33 could be used as an enhancer to elevate levels of transcription of an operably linked eukaryotic promoter, thereby increasing transcription of an adjacent gene.

FIGS. 2A, 2B, 2C, 2D, and 2E is an alignment of the following Y. lipolytica EL1 promoter regions described herein: the EL1F (SEQ ID NO:2) promoter region, which is the 1000 bp 5' upstream sequence (i.e., the −1000 to −1 region) of the EL1 gene in Yarrowia lipolytica, wherein the nucleotide 'A' of the EL1 translation initiation codon 'ATG' was designated as +1; the 716 bp EL1LM-P2 (SEQ ID NO:16) promoter region; the 720 bp EL1LM-P2P1 (SEQ ID NO:21) promoter region; the 718 bp EL1LM-P2P2 (SEQ ID NO:25) promoter region; the 361 bp EL1-P4 (SEQ ID NO:27) promoter region; and the 261 bp EL1-P5 (SEQ ID NO:29) promoter region. Sequence differences are noted with an arrow over the alignment and a box.

All of the modified promoters derived from the EL1F promoter set forth as SEQ ID NO:2 (i.e., 857 bp EL1L, 857 bp EL1LM, 716 bp EL1LM-P2, 720 bp EL1LM-P2P1, 718 bp EL1LM-P2P2, 361 bp EL1-P4, and 261 bp EL1-P5) comprise an adenine ['A'] to cytosine ['C'] substitution at the nucleotide corresponding to position −2 in SEQ ID NO:1. One of skill in the art will appreciate that a suitable promoter region of an EL1 Yarrowia gene may optionally comprise an adenine ['A'] or a cytosine ['C'] nucleotide at position −2; alternately, the modified EL1 promoter may also tolerate substitution of a thymine ['T'] nucleotide or guanine ['G'] nucleotide for the wildtype adenine ['A'] at position −2.

Additionally, it is to be noted that, compared to SEQ ID NO:6, SEQ ID NO:8 comprises a substitution of a cytosine ['C'] nucleotide for a guanine ['G'] nucleotide at position 382; thus modified EL1 promoters may also tolerate substitution of a thymine ['T'] nucleotide or an adenine ['A'] nucleotide for the wildtype guanine ['G'] at this position.

Example 7

Sequence Analysis of Promoter Regions of an EL1 Yarrowia Gene

The present Example describes the lack of a TATA-box within promoter regions of the EL1 *Yarrowia* gene.

Although promoters interact with the TATA binding protein ["TBP"] to create a transcription initiation complex from which RNA polymerase II transcribes the DNA coding sequence, only some promoters contain a TATA box to which TBP binds directly while other promoters are TATA-less promoters. The "TATA box" or "Goldberg-Hogness box" is a DNA sequence (i.e., cis-regulatory element) found in the promoter region of some genes in archaea and eukaryotes. For example, approximately 24% of human genes contain a TATA box within the core promoter (Yang C, et al., *Gene*, 389:52-65 (2007)); phylogenetic analysis of six *Saccharomyces* species revealed that about 20% of the 5,700 yeast genes contained a TATA-box element (Basehoar et al., *Cell*, 116: 699-709 (2004)). The TATA box has a core DNA sequence of 5'-TATAAA-3' or a variant thereof and is usually located ~200 to 25 base pairs upstream of the transcriptional start site. The transcription initiation complex forms at the site of the TATA box (Smale and Kadonaga, T., *Ann. Rev. Biochem.* 72:449-479 (2003)). This complex comprises the TATA binding protein, RNA polymerase II, and various transcription factors (i.e., TFIID, TFIIA, TFIIB, TFIIF, TFIIE and TFIIH). Both the TATA box itself and the distance between the TATA box and transcription start site affect activity of TATA box-containing promoters in eukaryotes (Zhu et al., *Plant Cell*, 7:1681-1689 (1995)).

The genes within *Yarrowia* can be largely classified into three classes according to their promoter sequences. Specifically, the first class of genes includes those comprising a TATA box, usually, ~130 to 20 base pairs upstream of the gene's transcription start site. The second class of genes includes those comprising an initiator element(s) around the gene's transcription start site. And, the third class of genes lacks both a TATA box and initiator element in the gene's promoter region.

Analysis of the sequence of the 261 bp EL1-P5 promoter region (Examples 5 and 6; SEQ ID NO:29) revealed that the promoter region does not contain a typical TATA-box. However, six possible initiator elements (PyA+1(T/A)Pu, Zhang et al., *Nucleic Acids Res.* 33:2838-2851 (2005)) were identified within a 207 bp sequence of the EL1-P5 promoter region (corresponding to nucleotides 6 to 213 of SEQ ID NO:29, which is equivalent to the −255 to −48 region upstream of the 'ATG' translation initiation codon of the EL1 gene). Based on identification of this 207 bp fragment, it is believed that a suitable minimal EL1 promoter region for basal level and some induced transcription initiation would comprise this fragment, set forth herein as SEQ ID NO:30. It is also hypothesized that the 255 base pair sequence (i.e., set forth as SEQ ID NO:32) spanning the −255 to −1 region upstream of the 'ATG' translation initiation codon of the EL1 gene would be suitable for basal level transcription initiation.

Example 8

Comparison of Various Yarrowia EL1 Promoter Regions

The present Example summarizes the relative activity of various EL1 promoter regions exemplified in Examples 1-6 above. It was concluded that the EL1 promoter is a very strong inducible promoter that can effectively be used to drive high level expression of various genes in engineered *Yarrowia* strains under nitrogen-limited conditions, as shown in Table 54 below.

TABLE 4

Summary of Relative Activity of Various EL1 Promoter Regions

| Construct Comprising GUS Reporter | Promoter Operably Linked to GUS Reporter | Promoter Length | Promoter Activity | |
|---|---|---|---|---|
| | | | Cultured in MM* | Cultured in MM + HGM** |
| pEL1GUS (SEQ ID NO: 15) | EL1LM (SEQ ID NO: 8) | 857 bp | + | +++ |
| pEL1GUS2 (SEQ ID NO: 17) | EL1LM-P2 (SEQ ID NO: 16) | 716 bp | + | +++ |
| pEL1GUS2-P1 (SEQ ID NO: 20) | EL1LM-P2P1 (SEQ ID NO: 21) | 720 bp | + | +++ |
| pEL1GUS2-P2 (SEQ ID NO: 24) | EL1LM-P2P2 (SEQ ID NO: 25) | 718 bp | + | +++ |
| pEL1GUS2-P4 (SEQ ID NO: 26) | EL1-P4 (SEQ ID NO: 27) | 361 bp | + | + |
| pEL1GUS2-P5 (SEQ ID NO: 28) | EL1-P5 (SEQ ID NO: 29) | 261 bp | + | ++ |

*Cultured In MM refers to 2 days growth in MM.
**Cultured in MM + HGM refers to 2 days growth in MM, followed by 3 days growth in HGM.

What is claimed is:

1. A method for the expression of a coding region of interest in a transformed yeast cell comprising:
   a) providing a transformed yeast cell having a recombinant construct, wherein the recombinant construct comprises:
      (1) a promoter region of a *Yarrowia* EL1 gene; and
      (2) a coding region of interest which is expressible in the yeast cell;
      wherein the promoter region is operably linked to the coding region of interest, and the promoter region is chimeric to the coding region; and
   b) growing the transformed yeast cell of step (a) under conditions whereby the recombinant construct of step (a) is expressed.

2. The method according to claim 1, wherein the promoter region of the *Yarrowia* EL1 gene comprises a sequence selected from the group consisting of SEQ ID NO:30 and SEQ ID NO:32.

3. The method according to claim 1, wherein the promoter region of the *Yarrowia* EL1 gene comprises SEQ ID NO:6, wherein said promoter region optionally comprises at least one modification selected from the group consisting of:
   a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;

b) substitution of an adenine ['A'] nucleotide for the cytosine ['C'] nucleotide at position 856 of SEQ ID NO:6;

c) substitution of a thymine ['T'] nucleotide or a guanine ['G'] nucleotide for the cytosine ['C'] nucleotide at position 856 of SEQ ID NO:6;

d) substitution of a cytosine ['C'] nucleotide for the guanine ['G'] nucleotide at position 382 of SEQ ID NO:6;

e) substitution of an adenine ['A'] nucleotide or a thymine ['T'] nucleotide for the guanine ['G'] nucleotide at position 382 of SEQ ID NO:6;

f) insertion of a nucleotide sequence 'TAAA' between position 496 and position 497 of SEQ ID NO:6;

g) insertion of a nucleotide sequence 'AC' between position 596 and position 597 of SEQ ID NO:6; and h) any combination of part a), part b), part c), part d), part e), part f), and part g).

4. The method according to claim 3, wherein the promoter region of the *Yarrowia* EL1 gene comprises a sequence selected from the group consisting of SEQ ID NO:8, SEQ ID NO:16, SEQ ID NO:21, SEQ ID NO:25, SEQ ID NO:27 and SEQ ID NO:29.

5. The method according to claim 1, wherein the transformed yeast cell is an oleaginous yeast cell.

6. The method of claim 5, wherein the oleaginous yeast cell is a member of a genus selected from the group consisting of *Yarrowia, Candida, Rhodotorula, Rhodosporidium, Cryptococcus, Trichosporon* and *Lipomyces.*

7. The method according to claim 1, wherein the coding region of interest encodes a polypeptide, wherein the polypeptide is selected from the group consisting of: desaturases, elongases, acyltransferases, aminopeptidases, amylases, carbohydrases, carboxypeptidases, catalases, cellulases, chitinases, cutinases, cyclodextrin glycosyltransferases, deoxyribonucleases, esterases, alpha-galactosidases, beta-galactosidases, glucoamylases, alpha-glucosidases, beta-glucanases, beta-glucosidases, invertases, laccases, lipases, mannosidases, mutanases, oxidases, pectinolytic enzymes, peroxidases, phospholipases, phosphatases, phytases, polyphenoloxidases, proteolytic enzymes, ribonucleases, transglutaminases and xylanases.

8. The method according to claim 1, wherein the promoter region of the *Yarrowia* EL1 gene further (i) comprises the enhancer region set forth in SEQ ID NO:33, or (ii) is operably linked to said enhancer region.

9. The method according to claim 1, wherein the coding region encodes at least one omega-3 fatty acid or omega-6 fatty acid biosynthetic pathway enzyme, and wherein an omega-3 fatty acid or omega-6 fatty acid is produced in step b).

10. The method according to claim 9, wherein the omega-3 fatty acid or omega-6 fatty acid biosynthetic pathway enzyme is selected from the group consisting of desaturases and elongases.

11. An isolated nucleic acid molecule comprising a promoter region of a *Yarrowia* EL1 gene as set forth in SEQ ID NO:6, wherein said promoter region is operably linked to a coding region, wherein said promoter region is chimeric to the coding region, and wherein said promoter region optionally comprises at least one modification selected from the group consisting of:

a) a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, or 596 consecutive nucleotides, wherein the first nucleotide deleted is the guanine ['G'] nucleotide at position 1 of SEQ ID NO:6;

b) substitution of an adenine ['A'] nucleotide for the cytosine ['C'] nucleotide at position 856 of SEQ ID NO:6;

c) substitution of a thymine ['T'] nucleotide or a guanine ['G'] nucleotide for the cytosine ['C'] nucleotide at position 856 of SEQ ID NO:6;

d) substitution of a cytosine ['C'] nucleotide for the guanine ['G'] nucleotide at position 382 of SEQ ID NO:6;

e) substitution of an adenine ['A'] nucleotide or a thymine ['T'] nucleotide for the guanine ['G'] nucleotide at position 382 of SEQ ID NO:6;

f) insertion of a nucleotide sequence 'TAAA' between position 496 and position 497 of SEQ ID NO:6;

g) insertion of a nucleotide sequence 'AC' between position 596 and position 597 of SEQ ID NO:6; and h) any combination of part a), part b), part c), part d), part e), part f), and part g).

12. The isolated nucleic acid molecule of claim 11, wherein the promoter region comprises a sequence selected from the group consisting of SEQ ID NO:8, SEQ ID NO:16, SEQ ID NO:21, SEQ ID NO:25, SEQ ID NO:27 and SEQ ID NO:29.

13. The isolated nucleic acid molecule of claim 11, wherein the promoter region of the *Yarrowia* EL1 gene further (i) comprises the enhancer region set forth in SEQ ID NO:33, or (ii) is operably linked to said enhancer region.

14. An isolated nucleic acid molecule comprising a promoter region of a *Yarrowia* EL1 gene comprising SEQ ID NO:30 or SEQ ID NO:32, wherein said promoter region is operably linked to a coding region, and said promoter region is chimeric to the coding region.

* * * * *

SEQUENCE LISTING

<160> NUMBER OF SEQ ID NOS: 33

<210> SEQ ID NO 1
<211> LENGTH: 2359
<212> TYPE: DNA
<213> ORGANISM: Yarrowia lipolytica
<220> FEATURE:
<221> NAME/KEY: misc_feature
<222> LOCATION: (1)..(2359)
<223> OTHER INFORMATION: YALI0E19899g locus (EL1 gene)
<220> FEATURE:
<221> NAME/KEY: misc_feature
<222> LOCATION: (1000)..(1003)
<223> OTHER INFORMATION: translation initiation codon 'ATG'; nucleotide
      'A' (designated as +1)

<400> SEQUENCE: 1

```
agggacagat cagtctagag aactgttgaa agggaagtat cacatgtctc cgaaaaaaaa          60
aacactgcta gcgtcaatgt gagtgccatg taccggacaa cattgaacgg tagacacgag         120
gctgcaatga caaccgctat cgtgattgat tcgactggaa acacaagatg aagatggctg         180
atcggttcat ctgcttgact tacattctgg atatatacga gtcgcagtgt gagttccgac         240
tcagactggg gaggatgcga ccagatcgaa atccagggca ggttctacac cttgcagagt         300
ggagctgtct cccatttcca agtccagagt gtggacgttc gggcttttcg agaatgtcga         360
gcagaaacag ggtcgagttg gcgcataagt accctctttc gatctgttta acctggagtt         420
ggggtgttat tttggattat gataaaaaag aagaatgaa aaaaaagaa aaaaaagaa          480 aaaaagaaa aaaaagaaa aagaagaca gtgacaatta gcatgcaacc ataagagcga         540
cacaagagac tcgaactcag aacacttgta tctggccaca tgtgcttcgt ctctcagtct         600
ctccatcgct tctaaattac cccaacatgt gccaaagttc aatgctagac agcaataggg         660 ttcccccac aatcttgggc agatgagagt ggggcggagg agatgtcatg gtcaattgtg          720
gcgtcaatgg agcgttaat gggcccaaaa gttgatagg tcgttcattg acagattagg          780
attgtagcgg tcaaaagaac cccccgaaaa agtccctcga cactctctct accatctccc         840
caaaatcgcc ttcatgtgat aaactctagc gcggggccgt tactctaacg aacttagaga         900
cattcacatg cggaggtacc gtagctacaa gtaccagtag aggaagtcca agtggataaa         960
tcgtcttccc gaataccgac tttctcacc accaattgac atggcgcacc tgaccaaga        1020 atactacgag ccgttccacc acgacgtgat tctcggcggc aagagatggc actacctgga        1080
cattcctccg gagggcaaag acaatggccg agtgctggtt ctggtccatg ggttccccga        1140
tttctggtac ggctggcgcc accagatccc cgtgttccgc aagcgaggcc accgaatcat        1200
cctgcccact ctgatgggat ttccgggctc gaggtaccc gaacctccgg ccatggagga         1260
gtttgaggag aacgaagatg gcatcaacat ctacacggag ctgggccagg aggacgactg        1320
tcgtgagctg cacttttacg gcttcaagtt ctttgctgac tgcatggccg aactgctcaa        1380
gaagctgaac atcaagtcgg ccacgttcct gggccacgac tggggcgccc actacgtccc        1440
caaggtctgg gcctaccacc ctgagattgt ggacgccatt tcgtcggcct gctggtacta        1500
ccaggtgccc gagcccgaat gggtgccgct gaccgacttc tccgacaagt ggcccaccac        1560
aaagtaccag ctgcagtttg gaggagacgc cgtcaacaac attggccccg gcatgatccc        1620
cttcttcctg cgacggtcct acaccgtggg agccaacttt gacggcgagc cggaccccga        1680
ggcgcccatg cacatgaccg aggaggagtt tgccgtgtac gaggagcact ttccaaggga        1740
gaaacggtcg ctggccggcc ccttcaccta ttaccgctcg cgaaaactca actgggagca        1800
```

```
ggacaaggag aacttcctcg ataagggggc caccaagaag gatctgaccg tcaacgtgcc   1860
atacctgtac attggctcca ccaacgacat tgctctgatt cccgaaatgt ccatgcactt   1920
ggacgagtat gtggagaagg gcaagctgac acgagagcac gtgcccacct cgcactgggc   1980
gctgttcgag gcccccgacc agatcaacaa gatctatgtt gattggctgg acaagctgga   2040
caagactagt aagctgtaga caccataata gatgcccata tttgaatgat ttagaataac   2100
tacggctgca ctagacacct gtagttggat cctatctgag ctaatctgga tagctaatct   2160
atgttgagta tttgtacaac tacaactaca gtagtcgta ccccgacggg cacttttcaa   2220
tttgtaatca atctgacaat ctcttagaca acaaccaatc aaagcaacgc aataagccac   2280
tggaagatac acccgagaag acaagccact ggaaacagat atccaaccct aagccaccag   2340
cacgcaccgg gactgagta                                                2359

<210> SEQ ID NO 2
<211> LENGTH: 1000
<212> TYPE: DNA
<213> ORGANISM: Yarrowia lipolytica

<400> SEQUENCE: 2
agggacagat cagtctagag aactgttgaa agggaagtat cacatgtctc cgaaaaaaaa     60
aacactgcta gcgtcaatgt gagtgccatg taccggacaa cattgaacgg tagacacgag    120
gctgcaatga caaccgctat cgtgattgat tcgactggaa cacaagatg aagatggctg     180 atcggttcat ctgcttgact tacattctgg atatatacga gtcgcagtgt gagttccgac    240
tcagactggg gaggatgcga ccagatcgaa atccagggca ggttctacac cttgcagagt    300
ggagctgtct cccatttcca gtccagagt gtggacgttc gggcttttcg agaatgtcga    360
gcagaaacag ggtcgagttg gcgcataagt accctctttc gatctgttta acctggagtt    420
ggggtgttat tttggattat gataaaaaag aaagaatgaa aaaaaagaa aaaaaagaa      480 aaaaagaaa aaaaagaaa aagaagaca gtgacaatta gcatgcaacc ataagagcga      540
cacaagagac tcgaactcag aacacttgta tctggccaca tgtgcttcgt ctctcagtct    600
ctccatcgct tctaaattac cccaacatgt gccaaagttc aatgctagac agcaataggg    660 ttcccccccac aatcttgggc agatgagagt ggggcggagg agatgtcatg gtcaattgtg    720
gcgtcaatgg agcgtttaat gggcccaaaa gttgataggg tcgttcattg acagattagg    780
attgtagcgg tcaaaagaac ccccgaaaa agtccctcga cactctctct accatctccc     840
caaaatcgcc ttcatgtgat aaactctagc gcggggccgt tactctaacg aacttagaga    900
cattcacatg cggaggtacc gtagctacaa gtaccagtag aggaagtcca agtggataaa    960
tcgtcttccc gaataccgac tttctcacc accaattgac                          1000

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
tccaatcgat tgattcgact ggaaacacaa gatg                                 34

<210> SEQ ID NO 4
<211> LENGTH: 38
<212> TYPE: DNA
<213> ORGANISM: Artificial Sequence
```

-continued

```
<220> FEATURE:
<223> OTHER INFORMATION: Primer

<400> SEQUENCE: 4
tttccatggc aattggtggt gagaaaagtc ggtattcg                            38

<210> SEQ ID NO 5
<211> LENGTH: 4824
<212> TYPE: DNA
<213> ORGANISM: Artificial Sequence
<220> FEATURE:
<223> OTHER INFORMATION: Plasmid

<400> SEQUENCE: 5
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagctca    240
gaattaaccc tcactaaagg gactagtcct gcaggtttaa acgaattcgc cctttccaat    300
cgattgattc gactgaaaac acaagatgaa gatggctgat cggttcatct gcttgactta    360
cattctggat atatacgagt cgcagtgtga gttccgactc agactgggga ggatgcgacc    420
agatcgaaat ccagggcagg ttctacacct tgcagagtgg agctgtctcc catttccaag    480
tccagagtgt ggacgttcgg gcttttcgag aatgtcgagc agaaacaggg tcgagttggc    540
gcataagtac cctctttcga tctgtttaac ctggagttgg ggtgttattt tggattatga    600 taaaaagaa agaatgaaaa aaaagaaaa aaaagaaaa aaagaaaaa aaagaaaaa        660 agaagacagt gacaattagc atgcaaccat aagagcgaca caagagactc gaactcagaa    720
cacttgtatc tggccacatg tgcttcgtct ctcagtctct ccatcgcttc taaattaccc    780
caacatgtgc caaagttcaa tgctagacag caatagggtt ccccccacaa tcttgggcag    840
atgagagtgg ggcggaggag atgtcatggt caattgtggc gtcaatggag cgtttaatgg    900
gcccaaaagt tgatagggtc gttcattgac agattaggat tgtagcggtc aaaagaaccc    960
cccgaaaaag tccctcgaca ctctctctac catctcccca aaatcgcctt catgtgataa   1020
actctagcgc ggggccgtta ctctaacgaa cttagagaca ttcacatgcg gaggtaccgt   1080
agctacaagt accagtagag gaagtccaag tggataaatc gtcttcccga ataccgactt   1140
ttctcaccac caattgccat ggaagggcga attgcggcc gctaaattca attcgcccta   1200
tagtgagtcg tattacaatt cactggccgt cgttttacaa cgtcgtgact gggaaaaccc   1260
tggcgttacc caacttaatc gccttgcagc acatccccct ttcgccagct ggcgtaatag   1320
cgaagaggcc cgcaccgatc gcccttccca acagttgcgc agcctatacg tacggcagtt   1380
taaggtttac acctataaaa gagagagccg ttatcgtctg tttgtggatg tacagagtga   1440
tattattgac acgccgggc gacgatggt gatcccctg gccagtgcac gtctgctgtc    1500
agataaagtc tcccgtgaac tttacccggt ggtgcatatc ggggatgaaa gctggcgcat   1560
gatgaccacc gatatggcca gtgtgccggt ctccgttatc ggggaagaag tggctgatct   1620
cagccaccgc gaaaatgaca tcaaaaacgc cattaacctg atgttctggg aatataaat    1680 gtcaggcatg agattatcaa aaaggatctt cacctagatc cttttcacgt agaaagccag   1740
tccgcagaaa cggtgctgac cccggatgaa tgtcagctac tgggctatct ggacaaggga   1800
aaacgcaagc gcaaagagaa agcaggtagc ttgcagtggg cttacatggc gatagctaga   1860
```

```
ctgggcggtt ttatggacag caagcgaacc ggaattgcca gctggggcgc cctctggtaa    1920
ggttgggaag ccctgcaaag taaactggat ggctttcttg ccgccaagga tctgatggcg    1980
caggggatca agctctgatc aagagacagg atgaggatcg tttcgcatga ttgaacaaga    2040
tggattgcac gcaggttctc cggccgcttg ggtggagagg ctattcggct atgactgggc    2100
acaacagaca atcggctgct ctgatgccgc cgtgttccgg ctgtcagcgc aggggcgccc    2160
ggttcttttt gtcaagaccg acctgtccgg tgccctgaat gaactgcaag acgaggcagc    2220
gcggctatcg tggctggcca cgacgggcgt tccttgcgca gctgtgctcg acgttgtcac    2280
tgaagcggga agggactggc tgctattggg cgaagtgccg gggcaggatc tcctgtcatc    2340
tcaccttgct cctgccgaga agtatccat catggctgat gcaatgcggc ggctgcatac    2400
gcttgatccg gctacctgcc cattcgacca ccaagcgaaa catcgcatcg agcgagcacg    2460
tactcggatg gaagccggtc ttgtcgatca ggatgatctg gacgaagagc atcaggggct    2520
cgcgccagcc gaactgttcg ccaggctcaa ggcgagcatg cccgacggcg aggatctcgt    2580
cgtgacccat ggcgatgcct gcttgccgaa tatcatggtg aaaatggcc gcttttctgg    2640
attcatcgac tgtggccggc tgggtgtggc ggaccgctat caggacatag cgttggctac    2700
ccgtgatatt gctgaagagc ttggcggcga atgggctgac cgcttcctcg tgctttacgg    2760
tatcgccgct cccgattcgc agcgcatcgc cttctatcgc cttcttgacg agttcttctg    2820
aattattaac gcttacaatt tcctgatgcg gtattttctc cttacgcatc tgtgcggtat    2880
ttcacaccgc atcaggtggc acttttcggg gaaatgtgcg cggaacccct atttgtttat    2940
ttttctaaat acattcaaat atgtatccgc tcatgagatt atcaaaaagg atcttcacct    3000
agatcctttt aaattaaaaa tgaagtttta atcaatcta agtatatat gagtaaactt    3060
ggtctgacag ttaccaatgc ttaatcagtg aggcacctat ctcagcgatc tgtctatttc    3120
gttcatccat agttgcctga ctccccgtcg tgtagataac tacgatacgg gagggcttac    3180
catctggccc cagtgctgca atgataccgc gagacccacg ctcaccggct ccagatttat    3240
cagcaataaa ccagccagcc ggaagggccg agcgcagaag tggtcctgca actttatccg    3300
cctccatcca gtctattaat tgttgccggg aagctagagt aagtagttcg ccagttaata    3360
gtttgcgcaa cgttgttgcc attgctacag gcatcgtggt gtcacgctcg tcgtttggta    3420
tggcttcatt cagctccggt tcccaacgat caaggcgagt tacatgatcc cccatgttgt    3480
gcaaaaaagc ggttagctcc ttcggtcctc cgatcgttgt cagaagtaag ttggccgcag    3540
tgttatcact catggttatg gcagcactgc ataattctct tactgtcatg ccatccgtaa    3600
gatgcttttc tgtgactggt gagtactcaa ccaagtcatt ctgagaatag tgtatgcggc    3660
gaccgagttg ctcttgcccg gcgtcaatac gggataatac cgcgccacat agcagaactt    3720
taaaagtgct catcattgga aaacgttctt cggggcgaaa actctcaagg atcttaccgc    3780
tgttgagatc cagttcgatg taacccactc gtgcacccaa ctgatcttca gcatctttta    3840
ctttcaccag cgtttctggg tgagcaaaaa caggaaggca aaatgccgca aaaaagggaa    3900
taagggcgac acggaaatgt tgaatactca tactcttcct ttttcaatat tattgaagca    3960
tttatcaggg ttattgtctc atgaccaaaa tcccttaacg tgagttttcg ttccactgag    4020
cgtcagaccc cgtagaaaag atcaaaggat cttcttgaga tcctttttt ctgcgcgtaa    4080
tctgctgctt gcaaacaaaa aaaccaccgc taccagcggt ggtttgtttg ccggatcaag    4140
agctaccaac tctttttccg aaggtaactg gcttcagcag agcgcagata ccaaatactg    4200
ttcttctagt gtagccgtag ttaggccacc acttcaagaa ctctgtagca ccgcctacat    4260
```

```
acctcgctct gctaatcctg ttaccagtgg ctgctgccag tggcgataag tcgtgtctta      4320
ccgggttgga ctcaagacga tagttaccgg ataaggcgca gcggtcgggc tgaacggggg      4380
gttcgtgcac acagcccagc ttggagcgaa cgacctacac cgaactgaga tacctacagc     4440
gtgagctatg agaaagcgcc acgcttcccg aagggagaaa ggcggacagg tatccggtaa     4500
gcggcagggt cggaacagga gagcgcacga gggagcttcc aggggggaaac gcctggtatc     4560 tttatagtcc tgtcgggttt cgccacctct gacttgagcg tcgatttttg tgatgctcgt     4620
caggggggcg gagcctatgg aaaaacgcca gcaacgcggc cttttttacgg ttcctggcct     4680 tttgctggcc ttttgctcac atgttctttc ctgcgttatc ccctgattct gtggataacc     4740
gtattaccgc ctttgagtga gctgataccg ctcgccgcag ccgaacgacc gagcgcagcg     4800
agtcagtgag cgaggaagcg gaag                                             4824

<210> SEQ ID NO 6
<211> LENGTH: 857
<212> TYPE: DNA
<213> ORGANISM: Yarrowia lipolytica

<400> SEQUENCE: 6
gattgattcg actggaaaca caagatgaag atggctgatc ggttcatctg cttgacttac       60
attctggata tatacgagtc gcagtgtgag ttccgactca gactggggag gatgcgacca      120
gatcgaaatc cagggcaggt tctacacctt gcagagtgga gctgtctccc atttccaagt      180
ccagagtgtg gacgttcggg cttttcgaga atgtcgagca gaaacagggt cgagttggcg      240
cataagtacc ctctttcgat ctgtttaacc tggagttggg gtgttatttt ggattatgat      300
aaaaaagaaa gaatgaaaaa aaagaaaaaa aaagaaaaaa aagaaaaaaa aagaaaaaa       360 gaagacagtg acaattagca tgcaaccata agagcgacac aagagactcg aactcagaac      420
acttgtatct ggccacatgt gcttcgtctc tcagtctctc catcgcttct aaattacccc      480
aacatgtgcc aaagttcaat gctagacagc aatagggttc cccccacaat cttgggcaga     540
tgagagtggg gcggaggaga tgtcatggtc aattgtggcg tcaatggagc gtttaatggg      600
cccaaaagtt gatagggtcg ttcattgaca gattaggatt gtagcggtca aaagaacccc      660
ccgaaaaagt ccctcgacac tctctctacc atctccccaa aatcgccttc atgtgataaa      720
ctctagcgcg gggccgttac tctaacgaac ttagagacat tcacatgcgg aggtaccgta      780
gctacaagta ccagtagagg aagtccaagt ggataaatcg tcttcccgaa taccgacttt      840
tctcaccacc aattgcc                                                     857

<210> SEQ ID NO 7
<211> LENGTH: 4824
<212> TYPE: DNA
<213> ORGANISM: Artificial sequence
<220> FEATURE:
<223> OTHER INFORMATION: Plasmid

<400> SEQUENCE: 7
agcgcccaat acgcaaaccg cctctccccg cgcgttggcc gattcattaa tgcagctggc       60
acgacaggtt cccgactgg aaagcgggca gtgagcgcaa cgcaattaat gtgagttagc      120
tcactcatta ggcaccccag gctttacact ttatgcttcc ggctcgtatg ttgtgtggaa      180
ttgtgagcgg ataacaattt cacacaggaa acagctatga ccatgattac gccaagctca      240
gaattaaccc tcactaaagg gactagtcct gcaggtttaa acgaattcgc cctttccaat      300
```

```
cgattgattc gactggaaac acaagatgaa gatggctgat cggttcatct gcttgactta    360
cattctggat atatacgagt cgcagtgtga gttccgactc agactgggga ggatgcgacc    420
agatcgaaat ccagggcagg ttctacacct tgcagagtgg agctgtctcc catttccaag    480
tccagagtgt ggacgttcgg gcttttcgag aatgtcgagc agaaacaggg tcgagttggc    540
gcataagtac cctctttcga tctgtttaac ctggagttgg ggtgttattt tggattatga    600
taaaaaagaa agaatgaaaa aaaagaaaaa aaaagaaaaa aaagaaaaaa aaagaaaaa     660 agaagacagt gacaattagc atccaaccat aagagcgaca caagagactc gaactcagaa    720
cacttgtatc tggccacatg tgcttcgtct ctcagtctct ccatcgcttc taaattaccc    780
caacatgtgc caaagttcaa tgctagacag caatagggtt ccccccacaa tcttgggcag    840
atgagagtgg ggcggaggag atgtcatggt caattgtggc gtcaatggag cgtttaatgg    900
gcccaaaagt tgatagggtc gttcattgac agattaggat tgtagcggtc aaaagaaccc    960
cccgaaaaag tccctcgaca ctctctctac catctcccca aaatcgcctt catgtgataa   1020
actctagcgc ggggccgtta ctctaacgaa cttagagaca ttcacatgcg gaggtaccgt   1080
agctacaagt accagtagag gaagtccaag tggataaatc gtcttcccga ataccgactt   1140
ttctcaccac caattgccat ggaagggcga attcgcggcc gctaaattca attcgcccta   1200
tagtgagtcg tattacaatt cactggccgt cgttttacaa cgtcgtgact gggaaaaccc   1260
tggcgttacc caacttaatc gccttgcagc acatccccct ttcgccagct ggcgtaatag   1320
cgaagaggcc cgcaccgatc gcccttccca acagttgcgc agcctatacg tacggcagtt   1380
taaggtttac acctataaaa gagagagccg ttatcgtctg tttgtggatg tacagagtga   1440
tattattgac acgccggggc gacggatggt gatcccctg ccagtgcac gtctgctgtc     1500 agataaagtc tcccgtgaac tttaccggt ggtgcatatc ggggatgaaa gctggcgcat     1560
gatgaccacc gatatggcca gtgtgccggt ctccgttatc ggggaagaag tggctgatct   1620
cagccaccgc gaaaatgaca tcaaaaacgc cattaacctg atgttctggg aatataaat    1680 gtcaggcatg agattatcaa aaaggatctt cacctagatc cttttcacgt agaaagccag   1740
tccgcagaaa cggtgctgac cccggatgaa tgtcagctac tgggctatct ggacaaggga   1800
aaacgcaagc gcaaagagaa agcaggtagc ttgcagtggg cttacatggc gatagctaga   1860
ctgggcggtt ttatgacag caagcgaacc ggaattgcca gctggggcgc cctctggtaa    1920
ggttgggaag ccctgcaaag taaactggat ggctttcttg ccgccaagga tctgatggcg   1980
caggggatca agctctgatc aagagacagg atgaggatcg tttcgcatga ttgaacaaga   2040
tggattgcac gcaggttctc cggccgcttg ggtggagagg ctattcggct atgactgggc   2100
acaacagaca atcggctgct ctgatgccgc cgtgttccgg ctgtcagcgc aggggcgccc   2160
ggttcttttt gtcaagaccg acctgtccgg tgccctgaat gaactgcaag acgaggcagc   2220
gcggctatcg tggctggcca cgacgggcgt tccttgcgca gctgtgctcg acgttgtcac   2280
tgaagcggga agggactggc tgctattggg cgaagtgccg gggcaggatc tcctgtcatc   2340
tcaccttgct cctgccgaga agtatccat catggctgat gcaatgcggc ggctgcatac    2400
gcttgatccg gctacctgcc cattcgacca ccaagcgaaa catcgcatcg agcgagcacg   2460
tactcggatg aagccggtc ttgtcgatca ggatgatctg gacgaagagc atcaggggct    2520
cgcgccagcc gaactgttcg ccaggctcaa ggcgagcatg cccgacggcg aggatctcgt   2580
cgtgacccat ggcgatgcct gcttgccgaa tatcatggtg aaaatggcc gcttttctgg    2640 attcatcgac tgtggccggc tgggtgtggc ggaccgctat caggacatag cgttggctac   2700
```

```
ccgtgatatt gctgaagagc ttggcggcga atgggctgac cgcttcctcg tgctttacgg   2760
tatcgccgct cccgattcgc agcgcatcgc cttctatcgc cttcttgacg agttcttctg   2820
aattattaac gcttacaatt tcctgatgcg gtattttctc cttacgcatc tgtgcggtat   2880
ttcacaccgc atcaggtggc acttttcggg gaaatgtgcg cggaacccct atttgtttat   2940
ttttctaaat acattcaaat atgtatccgc tcatgagatt atcaaaaagg atcttcacct   3000
agatcctttt aaattaaaaa tgaagtttta aatcaatcta aagtatatat gagtaaactt   3060
ggtctgacag ttaccaatgc ttaatcagtg aggcacctat ctcagcgatc tgtctatttc   3120
gttcatccat agttgcctga ctccccgtcg tgtagataac tacgatacgg agggcttac    3180
catctggccc cagtgctgca atgataccgc gagacccacg ctcaccggct ccagatttat   3240
cagcaataaa ccagccagcc ggaagggccg agcgcagaag tggtcctgca actttatccg   3300
cctccatcca gtctattaat tgttgccggg aagctagagt aagtagttcg ccagttaata   3360
gtttgcgcaa cgttgttgcc attgctacag gcatcgtggt gtcacgctcg tcgtttggta   3420
tggcttcatt cagctccggt tcccaacgat caaggcgagt tacatgatcc cccatgttgt   3480
gcaaaaaagc ggttagctcc ttcggtcctc cgatcgttgt cagaagtaag ttggccgcag   3540
tgttatcact catggttatg gcagcactgc ataattctct tactgtcatg ccatccgtaa   3600
gatgcttttc tgtgactggt gagtactcaa ccaagtcatt ctgagaatag tgtatgcggc   3660
gaccgagttg ctcttgcccg gcgtcaatac gggataatac cgcgccacat agcagaactt   3720
taaaagtgct catcattgga aaacgttctt cggggcgaaa actctcaagg atcttaccgc   3780
tgttgagatc cagttcgatg taacccactc gtgcacccaa ctgatcttca gcatcttta   3840
ctttcaccag cgtttctggg tgagcaaaaa caggaaggca aaatgccgca aaaaagggaa   3900
taagggcgac acggaaatgt tgaatactca tactcttcct ttttcaatat tattgaagca   3960
tttatcaggg ttattgtctc atgaccaaaa tcccttaacg tgagttttcg ttccactgag   4020
cgtcagaccc cgtagaaaag atcaaaggat cttcttgaga tccttttttt ctgcgcgtaa   4080
tctgctgctt gcaaacaaaa aaaccaccgc taccagcggt ggtttgtttg ccggatcaag   4140
agctaccaac tctttttccg aaggtaactg gcttcagcag agcgcagata ccaaatactg   4200
ttcttctagt gtagccgtag ttaggccacc acttcaagaa ctctgtagca ccgcctacat   4260
acctcgctct gctaatcctg ttaccagtgg ctgctgccag tggcgataag tcgtgtctta   4320
ccgggttgga ctcaagacga tagttaccgg ataaggcgca gcggtcgggc tgaacggggg   4380
gttcgtgcac acagcccagc ttggagcgaa cgacctacac cgaactgaga tacctacagc   4440
gtgagctatg agaaagcgcc acgcttcccg aagggagaaa ggcggacagg tatccggtaa   4500
gcggcagggt cggaacagga gagcgcacga gggagcttcc agggggaaac gcctggtatc   4560
tttatagtcc tgtcgggttt cgccacctct gacttgagcg tcgatttttg tgatgctcgt   4620
caggggggcg gagcctatgg aaaaacgcca gcaacgcggc cttttacgg ttcctggcct    4680
tttgctggcc ttttgctcac atgttctttc ctgcgttatc ccctgattct gtggataacc   4740
gtattaccgc ctttgagtga gctgataccg ctcgccgcag ccgaacgacc gagcgcagcg   4800
agtcagtgag cgaggaagcg gaag                                          4824
```

<210> SEQ ID NO 8
<211> LENGTH: 857
<212> TYPE: DNA
<213> ORGANISM: Yarrowia lipolytica -continued

```
<400> SEQUENCE: 8
gattgattcg actggaaaca caagatgaag atggctgatc ggttcatctg cttgacttac      60
attctggata tatacgagtc gcagtgtgag ttccgactca gactggggag gatgcgacca     120
gatcgaaatc cagggcaggt tctacacctt gcagagtgga gctgtctccc atttccaagt     180
ccagagtgtg gacgttcggg cttttcgaga atgtcgagca gaaacagggt cgagttggcg     240
cataagtacc ctctttcgat ctgtttaacc tggagttggg gtgttatttt ggattatgat     300
aaaaaagaaa gaatgaaaaa aaaagaaaaa aaaagaaaaa aaagaaaaaa aaagaaaaaa     360
gaagacagtg acaattagca tccaaccata gagcgacac aagagactcg aactcagaac      420
acttgtatct ggccacatgt gcttcgtctc tcagtctctc catcgcttct aaattacccc     480
aacatgtgcc aaagttcaat gctagacagc aatagggttc cccccacaat cttgggcaga     540
tgagagtggg gcggaggaga tgtcatggtc aattgtggcg tcaatggagc gtttaatggg     600
cccaaaagtt gatagggtcg ttcattgaca gattaggatt gtagcggtca aaagaaaccc     660
ccgaaaaagt ccctcgacac tctctctacc atctccccaa aatcgccttc atgtgataaa     720
ctctagcgcg gggccgttac tctaacgaac ttagagacat tcacatgcgg aggtaccgta     780
gctacaagta ccagtagagg aagtccaagt ggataaatcg tcttcccgaa taccgacttt     840
tctcaccacc aattgcc                                                    857

<210> SEQ ID NO 9
<211> LENGTH: 35
<212> TYPE: DNA
<213> ORGANISM: Artificial sequence
<220> FEATURE:
<223> OTHER INFORMATION: Primer

<400> SEQUENCE: 9
acagtgacaa ttagcatcca accataagag cgaca                                 35

<210> SEQ ID NO 10
<211> LENGTH: 35
<212> TYPE: DNA
<213> ORGANISM: Artificial sequence
<220> FEATURE:
<223> OTHER INFORMATION: Primer

<400> SEQUENCE: 10
tgtcgctctt atggttggat gctaattgtc actgt                                 35

<210> SEQ ID NO 11
<211> LENGTH: 4828
<212> TYPE: DNA
<213> ORGANISM: Artificial Sequence
<220> FEATURE:
<223> OTHER INFORMATION: Plasmid

<400> SEQUENCE: 11
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc cctttccaat     300
cgattgattc gactgaaaac acaagatgaa gatggctgat cggttcatct gcttgactta     360
cattctggat atatacgagt cgcagtgtga gttccgactc agactgggga ggatgcgacc     420
```

```
agatcgaaat ccagggcagg tttaaactac accttgcaga gtggagctgt ctcccatttc      480
caagtccaga gtgtggacgt tcgggctttt cgagaatgtc gagcagaaac agggtcgagt      540
tggcgcataa gtaccctctt tcgatctgtt taacctggag ttggggtgtt attttggatt      600
atgataaaaa agaagaatg aaaaaaaaag aaaaaaaaag aaaaaaaga aaaaaaaga        660 aaaagaaga cagtgacaat tagcatccaa ccataagagc gacacaagag actcgaactc       720
agaacacttg tatctggcca catgtgcttc gtctctcagt ctctccatcg cttctaaatt      780
accccaacat gtgccaaagt tcaatgctag acagcaatag ggttccccc acaatcttgg       840 gcagatgaga gtgggcgga ggagatgtca tggtcaattg tggcgtcaat ggagcgttta      900
atgggcccaa aagttgatag ggtcgttcat tgacagatta ggattgtagc ggtcaaaaga     960
accccccgaa aaagtccctc gacactctct ctaccatctc cccaaaatcg ccttcatgtg     1020
ataaactcta gcgcggggcc gttactctaa cgaacttaga gacattcaca tgcggaggta     1080
ccgtagctac aagtaccagt agaggaagtc caagtggata aatcgtcttc ccgaataccg     1140
acttttctca ccaccaattg ccatggaagg gcgaattcgc ggccgctaaa ttcaattcgc     1200
cctatagtga gtcgtattac aattcactgg ccgtcgtttt acaacgtcgt gactgggaaa     1260
accctggcgt tacccaactt aatcgccttg cagcacatcc ccctttcgcc agctggcgta     1320
atagcgaaga ggcccgcacc gatcgccctt cccaacagtt gcgcagccta tacgtacggc     1380
agtttaaggt ttacacctat aaaagagaga gccgttatcg tctgtttgtg gatgtacaga     1440
gtgatattat tgacacgccg gggcgacgga tggtgatccc cctggccagt gcacgtctgc     1500
tgtcagataa agtctcccgt gaactttacc cggtggtgca tatcggggat gaaagctggc     1560
gcatgatgac caccgatatg gccagtgtgc cggtctccgt tatcgggaa gaagtggctg     1620 atctcagcca ccgcgaaaat gacatcaaaa acgccattaa cctgatgttc tggggaatat     1680
aaatgtcagg catgagatta tcaaaaagga tcttcaccta gatccttttc acgtagaaag     1740
ccagtccgca gaaacggtgc tgaccccgga tgaatgtcag ctactgggct atctggacaa     1800
gggaaaacgc aagcgcaaag agaaagcagg tagcttgcag tgggcttaca tggcgatagc     1860
tagactgggc ggttttatgg acagcaagcg aaccggaatt gccagctggg gcgccctctg     1920
gtaaggttgg gaagccctgc aaagtaaact ggatggcttt cttgccgcca aggatctgat     1980
ggcgcagggg atcaagctct gatcaagaga caggatgagg atcgtttcgc atgattgaac     2040
aagatggatt gcacgcaggt tctccggccg cttgggtgga gaggctattc ggctatgact     2100
gggcacaaca gacaatcggc tgctctgatg ccgccgtgtt ccggctgtca gcgcaggggc     2160
gcccggttct ttttgtcaag accgacctgt ccggtgccct gaatgaactg caagacgagg     2220
cagcgcggct atcgtggctg gccacgacgg gcgttccttg cgcagctgtg ctcgacgttg     2280
tcactgaagc gggaagggac tggctgctat tgggcgaagt gccggggcag gatctcctgt     2340
catctcacct tgctcctgcc gagaaagtat ccatcatggc tgatgcaatg cggcggctgc     2400
atacgcttga tccggctacc tgcccattcg accaccaagc gaaacatcgc atcgagcgag     2460
cacgtactcg gatggaagcc ggtcttgtcg atcaggatga tctggacgaa gagcatcagg     2520
ggctcgcgcc agccgaactg ttcgccaggc tcaaggcgag catgcccgac ggcgaggatc     2580
tcgtcgtgac ccatggcgat gcctgcttgc cgaatatcat ggtggaaaat ggccgctttt     2640
ctggattcat cgactgtggc cggctgggtg tggcggaccg ctatcaggac atagcgttgg     2700
ctacccgtga tattgctgaa gagcttggcg gcgaatgggc tgaccgcttc ctcgtgcttt     2760
```

-continued

| | |
|---|---|
| acggtatcgc cgctcccgat tcgcagcgca tcgccttcta tcgccttctt gacgagttct | 2820 |
| tctgaattat taacgcttac aatttcctga tgcggtattt tctccttacg catctgtgcg | 2880 |
| gtatttcaca ccgcatcagg tggcactttt cggggaaatg tgcgcggaac ccctatttgt | 2940 |
| ttattttct aaatacattc aaatatgtat ccgctcatga gattatcaaa aaggatcttc | 3000 |
| acctagatcc tttttaaatta aaaatgaagt tttaaatcaa tctaaagtat atatgagtaa | 3060 |
| acttggtctg acagttacca atgcttaatc agtgaggcac ctatctcagc gatctgtcta | 3120 |
| tttcgttcat ccatagttgc ctgactcccc gtcgtgtaga taactacgat acgggagggc | 3180 |
| ttaccatctg gccccagtgc tgcaatgata ccgcgagacc cacgctcacc ggctccagat | 3240 |
| ttatcagcaa taaaccagcc agccggaagg gccgagcgca gaagtggtcc tgcaacttta | 3300 |
| tccgcctcca tccagtctat taattgttgc cgggaagcta gagtaagtag ttcgccagtt | 3360 |
| aatagtttgc gcaacgttgt tgccattgct acaggcatcg tggtgtcacg ctcgtcgttt | 3420 |
| ggtatggctt cattcagctc cggttcccaa cgatcaaggc gagttacatg atcccccatg | 3480 |
| ttgtgcaaaa aagcggttag ctccttcggt cctccgatcg ttgtcagaag taagttggcc | 3540 |
| gcagtgttat cactcatggt tatggcagca ctgcataatt ctcttactgt catgccatcc | 3600 |
| gtaagatgct tttctgtgac tggtgagtac tcaaccaagt cattctgaga atagtgtatg | 3660 |
| cggcgaccga gttgctcttg cccggcgtca atacgggata ataccgcgcc acatagcaga | 3720 |
| actttaaaag tgctcatcat tggaaaacgt tcttcggggc gaaaactctc aaggatctta | 3780 |
| ccgctgttga gatccagttc gatgtaaccc actcgtgcac ccaactgatc ttcagcatct | 3840 |
| tttactttca ccagcgtttc tgggtgagca aaaacaggaa ggcaaaatgc cgcaaaaaag | 3900 |
| ggaataaggg cgacacggaa atgttgaata ctcatactct ccttttttca atattattga | 3960 |
| agcatttatc agggttattg tctcatgacc aaaatccctt aacgtgagtt ttcgttccac | 4020 |
| tgagcgtcag accccgtaga aaagatcaaa ggatcttctt gagatccttt ttttctgcgc | 4080 |
| gtaatctgct gcttgcaaac aaaaaaacca ccgctaccag cggtggtttg tttgccggat | 4140 |
| caagagctac caactctttt tccgaaggta actggcttca gcagagcgca gataccaaat | 4200 |
| actgttcttc tagtgtagcc gtagttaggc caccacttca agaactctgt agcaccgcct | 4260 |
| acatacctcg ctctgctaat cctgttacca gtggctgctg ccagtggcga taagtcgtgt | 4320 |
| cttaccgggt tggactcaag acgatagtta ccggataagg cgcagcggtc gggctgaacg | 4380 |
| gggggttcgt gcacacagcc cagcttggag cgaacgacct acaccgaact gagatacccta | 4440 |
| cagcgtgagc tatgagaaag cgccacgctt cccgaaggga gaaaggcgga caggtatccg | 4500 |
| gtaagcggca gggtcggaac aggagagcgc acgagggagc ttccaggggg aaacgcctgg | 4560 |
| tatctttata gtcctgtcgg gtttcgccac ctctgacttg agcgtcgatt tttgtgatgc | 4620 |
| tcgtcagggg ggcggagcct atggaaaaac gccagcaacg cggccttttt acggttcctg | 4680 |
| gccttttgct ggccttttgc tcacatgttc tttcctgcgt tatcccctga ttctgtggat | 4740 |
| aaccgtatta ccgcctttga gtgagctgat accgctcgcc gcagccgaac gaccgagcgc | 4800 |
| agcgagtcag tgagcgagga agcggaag | 4828 |

<210> SEQ ID NO 12
<211> LENGTH: 38
<212> TYPE: DNA
<213> ORGANISM: Artificial sequence
<220> FEATURE:
<223> OTHER INFORMATION: Primer

<400> SEQUENCE: 12

```
gaaatccagg gcaggtttaa actacacctt gcagagtg                              38
```

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13

```
cactctgcaa ggtgtagttt aaacctgccc tggatttc                              38
```

<210> SEQ ID NO 14
<211> LENGTH: 9348
<212> TYPE: DNA
<213> ORGANISM: Artificial Sequence
<220> FEATURE:
<223> OTHER INFORMATION: Plasmid

<400> SEQUENCE: 14

```
ggtggagctc cagcttttgt tccctttagt gagggttaat ttcgagcttg gcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
cccctgacga gcatcacaaa aatcgacgct caagtcagag gtggcgaaac ccgacaggac     540
tataaagata ccaggcgttt ccccctggaa gctccctcgt gcgctctcct gttccgaccc     600
tgccgcttac cggatacctg tccgcctttc tcccttcggg aagcgtggcg ctttctcata     660
gctcacgctg taggtatctc agttcggtgt aggtcgttcg ctccaagctg ggctgtgtgc     720
acgaaccccc cgttcagccc gaccgctgcg ccttatccgg taactatcgt cttgagtcca     780
acccggtaag acacgactta tcgccactgg cagcagccac tggtaacagg attagcagag     840
cgaggtatgt aggcggtgct acagagttct tgaagtggtg gcctaactac ggctacacta     900
gaaggacagt atttggtatc tgcgctctgc tgaagccagt taccttcgga aaaagagttg     960
gtagctcttg atccggcaaa caaaccaccg ctggtagcgg tggtttttttt gtttgcaagc    1020
agcagattac gcgcagaaaa aaaggatctc aagaagatcc tttgatcttt tctacggggt    1080
ctgacgctca gtggaacgaa aactcacgtt aagggatttt ggtcatgaga ttatcaaaaa    1140
ggatcttcac ctagatcctt ttaaattaaa aatgaagttt taaatcaatc taaagtatat    1200
atgagtaaac ttggtctgac agttaccaat gcttaatcag tgaggcacct atctcagcga    1260
tctgtctatt tcgttcatcc atagttgcct gactccccgt cgtgtagata actacgatac    1320
gggagggctt accatctggc cccagtgctg caatgatacc gcgagaccca cgctcaccgg    1380
ctccagattt atcagcaata aaccagccag ccggaagggc cgagcgcaga agtggtcctg    1440
caactttatc cgcctccatc cagtctatta attgttgccg ggaagctaga gtaagtagtt    1500
cgccagttaa tagtttgcgc aacgttgttg ccattgctac aggcatcgtg gtgtcacgct    1560
cgtcgtttgg tatggcttca ttcagctccg gttcccaacg atcaaggcga gttacatgat    1620
```

```
cccccatgtt gtgcaaaaaa gcggttagct ccttcggtcc tccgatcgtt gtcagaagta    1680
agttggccgc agtgttatca ctcatggtta tggcagcact gcataattct cttactgtca    1740
tgccatccgt aagatgcttt tctgtgactg gtgagtactc aaccaagtca ttctgagaat    1800
agtgtatgcg gcgaccgagt tgctcttgcc cggcgtcaat acgggataat accgcgccac    1860
atagcagaac tttaaaagtg ctcatcattg gaaaacgttc ttcggggcga aaactctcaa    1920
ggatcttacc gctgttgaga tccagttcga tgtaacccac tcgtgcaccc aactgatctt    1980
cagcatcttt tactttcacc agcgtttctg ggtgagcaaa acaggaagg caaaatgccg     2040
caaaaaggg aataagggcg acacggaaat gttgaatact catactcttc cttttcaat      2100
attattgaag catttatcag ggttattgtc tcatgagcgg atacatattt gaatgtattt    2160
agaaaaataa acaaataggg gttccgcgca catttccccg aaaagtgcca cctgacgcgc    2220
cctgtagcgg cgcattaagc gcggcgggtg tggtggttac gcgcagcgtg accgctacac    2280
ttgccagcgc cctagcgccc gctcctttcg ctttcttccc ttcctttctc gccacgttcg    2340
ccggctttcc ccgtcaagct ctaaatcggg ggctcccttt agggttccga tttagtgctt    2400
tacggcacct cgaccccaaa aaacttgatt agggtgatgg ttcacgtagt gggccatcgc    2460
cctgatagac ggtttttcgc cctttgacgt tggagtccac gttctttaat agtggactct    2520
tgttccaaac tggaacaaca ctcaacccta tctcggtcta ttctttttgat ttataaggga   2580
ttttgccgat ttcggcctat tggttaaaaa atgagctgat ttaacaaaaa tttaacgcga    2640
attttaacaa atatattaacg cttacaattt ccattcgcca ttcaggctgc gcaactgttg   2700
ggaagggcga tcggtgcggg cctcttcgct attacgccag ctggcgaaag ggggatgtgc    2760
tgcaaggcga ttaagttggg taacgccagg gttttcccag tcacgacgtt gtaaaacgac    2820
ggccagtgaa ttgtaatacg actcactata gggcgaattg ggtaccgggc cccccctcga    2880
ggtcgatggt gtcgataagc ttgatatcga attcatgtca cacaaaccga tcttcgcctc    2940
aaggaaacct aattctacat ccgagagact gccgagatcc agtctacact gattaatttt    3000
cgggccaata atttaaaaaa atcgtgttat ataatattat atgtattata tatatacatc    3060
atgatgatac tgacagtcat gtcccattgc taaatagaca gactccatct gccgcctcca    3120
actgatgttc tcaatatttta aggggtcatc tcgcattgtt taataataaa cagactccat    3180
ctaccgcctc caaatgatgt tctcaaaata tattgtatga acttattttt attacttagt    3240
attattagac aacttacttg ctttatgaaa aacacttcct atttaggaaa caatttataa    3300
tgcagttcg ttcatttaac aatttatgta gaataaatgt tataaatgcg tatgggaaat     3360
cttaaatatg gatagcataa atgatatctg cattgcctaa ttcgaaatca acagcaacga    3420
aaaaaatccc ttgtacaaca taaatagtca tcgagaaata tcaactatca agaacagct    3480
attcacacgt tactattgag attattattg gacgagaatc acacactcaa ctgtctttct    3540
ctcttctaga aatacaggta caagtatgta ctattctcat tgttcatact tctagtcatt    3600
tcatcccaca tattccttgg atttctctcc aatgaatgac attctatctt gcaaattcaa    3660
caattataat aagatatacc aaagtagcgg tatagtggca atcaaaaagc ttctctggtg    3720
tgcttctcgt atttattttt attctaatga tccattaaag gtatatattt atttcttgtt    3780
atataatcct tttgttttatt acatgggctg gatacataaa ggtattttga tttaatttt     3840
tgcttaaatt caatcccccc tcgttcagtg tcaactgtaa tggtaggaaa ttaccatact    3900
tttgaagaag caaaaaaaat gaaagaaaaa aaaaatcgta tttccaggtt agacgttccg    3960
cagaatctag aatgcggtat gcggtacatt gttcttcgaa cgtaaaagtt gcgctccctg    4020
```

```
agatattgta cattttttgct tttacaagta caagtacatc gtacaactat gtactactgt   4080
tgatgcatcc acaacagttt gttttgtttt ttttttgtttt ttttttttttct aatgattcat   4140 taccgctatg tatacctact tgtacttgta gtaagccggg ttattggcgt tcaattaatc   4200
atagacttat gaatctgcac ggtgtgcgct gcgagttact tttagcttat gcatgctact   4260
tgggtgtaat attgggatct gttcggaaat caacggatgc tcaaccgatt tcgacagtaa   4320
taatttgaat cgaatcggag cctaaaatga acccgagtat atctcataaa attctcggtg   4380
agaggtctgt gactgtcagt acaaggtgcc ttcattatgc cctcaacctt accatacctc   4440
actgaatgta gtgtacctct aaaaatgaaa tacagtgcca aaagccaagg cactgagctc   4500
gtctaacgga cttgatatac aaccaattaa aacaaatgaa aagaaataca gttctttgta   4560
tcatttgtaa caattaccct gtacaaacta aggtattgaa atcccacaat attcccaaag   4620
tccacccctt tccaaattgt catgcctaca actcatatac caagcactaa cctaccaaac   4680
accactaaaa ccccacaaaa tatatcttac cgaatataca gtaacaagct accaccacac   4740
tcgttgggtg cagtcgccag cttaaagata tctatccaca tcagccacaa ctcccttcct   4800
ttaataaacc gactacaccc ttggctattg aggttatgag tgaatatact gtagacaaga   4860
cactttcaag aagactgttt ccaaaacgta ccactgtcct ccactacaaa cacacccaat   4920
ctgcttcttc tagtcaaggt tgctacaccg gtaaattata aatcatcatt tcattagcag   4980
ggcagggccc tttttataga gtcttataca ctagcggacc ctgccggtag accaacccgc   5040
aggcgcgtca gtttgctcct tccatcaatg cgtcgtagaa acgacttact ccttcttgag   5100
cagctccttg accttgttgg caacaagtct ccgacctcgg aggtggagga agagcctccg   5160
atatcggcgg tagtgatacc agcctcgacg gactccttga cggcagcctc aacagcgtca   5220
ccggcgggct tcatgttaag agagaacttg agcatcatgg cggcagacag aatggtggca   5280
atggggttga ccttctgctt gccgagatcg ggggcagatc cgtgacaggg ctcgtacaga   5340
ccgaacgcct cgttggtgtc gggcagagaa gccagagagg cggagggcag cagacccaga   5400
gaaccgggga tgacggaggc ctcgtcggag atgatatcgc caaacatgtt ggtggtgatg   5460
atgataccat tcatcttgga gggctgcttg atgaggatca tggcggccga gtcgatcagc   5520
tggtggttga gctcgagctg ggggaattcg tccttgagga ctcgagtgac agtctttcgc   5580
caaagtcgag aggaggccag cacgttggcc ttgtcaagac caccacgggg aagaggggggg   5640 ttgtgctgaa gggccaggaa ggcggccatt cgggcaattc gctcaacctc aggaacggag   5700
taggtctcgg tgtcggaagc gacgccagat ccgtcatcct cctttcgctc tccaaagtag   5760
atacctccga cgagctctcg gacaatgatg aagtcggtgc cctcaacgtt tcggatgggg   5820
gagagatcgg cgagcttggg cgacagcagc tggcagggtc gcaggttggc gtacaggttc   5880
aggtcctttc gcagcttgag gagaccctgc tcgggtcgca cgtcggttcg tccgtcggga   5940
gtggtccata cggtgttggc agcgcctccg acagcaccga gcataataga gtcagccttt   6000
cggcagatgt cgagagtagc gtcggtgatg ggctcgccct ccttctcaat ggcagctcct   6060
ccaatgagtc ggtcctcaaa cacaaactcg gtgccggagg cctcagcaac agacttgagc   6120
accttgacgg cctcggcaat cacctcgggg ccacagaagt cgccgccgag aagaacaatc   6180 ttccttggagt cagtcttggt cttcttagtt tcgggttcca ttgtggatgt gtgtggttgt   6240
atgtgtgatg tggtgtgtgg agtgaaaatc tgtggctggc aaacgctctt gtatatatac   6300
gcacttttgc ccgtgctatg tggaagacta aacctccgaa gattgtgact caggtagtgc   6360
```

-continued

| | |
|---|---|
| ggtatcggct agggacccaa accttgtcga tgccgatagc gctatcgaac gtaccccagc | 6420 |
| cggccgggag tatgtcggag gggacatacg agatcgtcaa gggtttgtgg ccaactggta | 6480 |
| aataaatgat gtcgacgttt aaacagtgta cgcagtacta tagaggaaca attgccccgg | 6540 |
| agaagacggc caggccgcct agatgacaaa ttcaacaact cacagctgac tttctgccat | 6600 |
| tgccactagg gggggccctt tttatatggc caagccaagc tctccacgtc ggttgggctg | 6660 |
| cacccaacaa taaatgggta gggttgcacc aacaaaggga tgggatgggg ggtagaagat | 6720 |
| acgaggataa cggggctcaa tggcacaaat aagaacgaat actgccatta agactcgtga | 6780 |
| tccagcgact acaccattg catcatcatc atctaagggc ctcaaaacta cctcggaact | 6840 |
| gctgcgctga tctggacacc acagaggttc cgagcacttt aggttgcacc aaatgtccca | 6900 |
| ccaggtgcag gcagaaaacg ctggaacagc gtgtacagtt tgtcttaaca aaagtgagg | 6960 |
| gcgctgaggt cgagcagggt ggtgtgactt gttatagcct ttagagctgc gaaagcgcgt | 7020 |
| atggatttgg ctcatcaggc cagattgagg gtctgtggac acatgtcatg ttagtgtact | 7080 |
| tcaatcgccc cctggatata gccccgacaa taggccgtgg cctcattttt ttgccttccg | 7140 |
| cacatttcca ttgctcggta cccacacctt gcttctcctg cacttgccaa ccttaatact | 7200 |
| ggtttacatt gaccaacatc ttacaagcgg ggggcttgtc tagggtatat ataaacagtg | 7260 |
| gctctcccaa tcggttgcca gtctcttttt tcctttcttt ccccacagat tcgaaatcta | 7320 |
| aactacacat cacaccatgg catggatggt acgtcctgta gaaacccaa cccgtgaaat | 7380 |
| caaaaaactc gacggcctgt gggcattcag tctggatcgc gaaaactgtg gaattgatca | 7440 |
| gcgttggtgg gaaagcgcgt tacaagaaag ccgggcaatt gctgtgccag cagttttaa | 7500 |
| cgatcagttc gccgatgcag atattcgtaa ttatgcgggc aacgtctggt atcagcgcga | 7560 |
| agtctttata ccgaaaggtt gggcaggcca gcgtatcgtg ctgcgtttcg atgcggtcac | 7620 |
| tcattacggc aaagtgtggg tcaataatca ggaagtgatg gagcatcagg cggctatac | 7680 |
| gccatttgaa gccgatgtca cgccgtatgt tattgccggg aaaagtgtac gtatcaccgt | 7740 |
| ttgtgtgaac aacgaactga actggcagac tatcccgccg ggaatggtga ttaccgacga | 7800 |
| aaacggcaag aaaaagcagt cttacttcca tgatttcttt aactatgccg ggatccatcg | 7860 |
| cagcgtaatg ctctacacca cgccgaacac ctgggtggac gatatcaccg tggtgacgca | 7920 |
| tgtcgcgcaa gactgtaacc acgcgtctgt tgactggcag gtggtggcca atggtgatgt | 7980 |
| cagcgttgaa ctgcgtgatg cggatcaaca ggtggttgca actggacaag cactagcgg | 8040 |
| gactttgcaa gtggtgaatc cgcacctctg caaccgggt gaaggttatc tctatgaact | 8100 |
| gtgcgtcaca gccaaaagcc agacagagtg tgatatctac ccgcttcgcg tcggcatccg | 8160 |
| gtcagtggca gtgaagggcg aacagttcct gattaaccac aaaccgttct actttactgg | 8220 |
| ctttggtcgt catgaagatg cggacttacg tggcaaagga ttcgataacg tgctgatggt | 8280 |
| gcacgaccac gcattaatgg actgattgg ggccaactcc taccgtacct cgcattaccc | 8340 |
| ttacgctgaa gagatgctcg actgggcaga tgaacatggc atcgtggtga ttgatgaaac | 8400 |
| tgctgctgtc ggctttaacc tctctttagg cattggtttc gaagcgggca acaagccgaa | 8460 |
| agaactgtac agcgaagagg cagtcaacgg ggaaactcag caagcgcact acaggcgat | 8520 |
| taaagagctg atagcgcgtg acaaaaacca cccaagcgtg gtgatgtgga gtattgccaa | 8580 |
| cgaaccggat acccgtccgc aagtgcacgg aatatttcg ccactggcgg aagcaacgcg | 8640 |
| taaactcgac ccgacgcgtc cgatcacctg cgtcaatgta atgttctgcg acgctcacac | 8700 |
| cgataccatc agcgatctct tgatgtgct gtgcctgaac cgttattacg gatggtatgt | 8760 |

```
ccaaagcggc gatttggaaa cggcagagaa ggtactggaa aaagaacttc tggcctggca   8820
ggagaaactg catcagccga ttatcatcac cgaatacggc gtggatacgt tagccgggct   8880
gcactcaatg tacaccgaca gtgtggagtga agagtatcag tgtgcatggc tggatatgta   8940
tcaccgcgtc tttgatcgcg tcagcgccgt cgtcggtgaa caggtatgga atttcgccga   9000
ttttgcgacc tcgcaaggca tattgcgcgt tggcggtaac aagaaaggga tcttcactcg   9060
cgaccgcaaa ccgaagtcgg cggcttttct gctgcaaaaa cgctggactg gcatgaactt   9120
cggtgaaaaa ccgcagcagg gaggcaaaca atgattaatt aactagagcg gccgccaccg   9180
cggcccgaga ttccggcctc ttcggccgcc aagcgacccg ggtggacgtc tagaggtacc   9240
tagcaattaa cagatagttt gccggtgata attctcttaa cctcccacac tcctttgaca   9300
taacgattta tgtaacgaaa ctgaaatttg accagatatt gtgtccgc                9348
```

<210> SEQ ID NO 15
<211> LENGTH: 9392
<212> TYPE: DNA
<213> ORGANISM: Artificial Sequence
<220> FEATURE:
<223> OTHER INFORMATION: Plasmid

<400> SEQUENCE: 15

```
catggcatgg atggtacgtc ctgtagaaac cccaacccgt gaaatcaaaa aactcgacgg     60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt gcaagtggt    720 gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat taccctttacg ctgaagagat   1020 gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt gccaacgaac cggatacccg   1260
tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
```

-continued

```
ggaaacggca gagaaggtac tggaaaaaga acttctggcc tggcaggaga aactgcatca    1500
gccgattatc atcaccgaat acggcgtgga tacgttagcc gggctgcact caatgtacac    1560
cgacatgtgg agtgaagagt atcagtgtgc atggctggat atgtatcacc gcgtctttga    1620
tcgcgtcagc gccgtcgtcg gtgaacaggt atggaatttc gccgattttg cgacctcgca    1680
aggcatattg cgcgttggcg gtaacaagaa agggatcttc actcgcgacc gcaaaccgaa    1740
gtcggcggct tttctgctgc aaaaacgctg gactggcatg aacttcggtg aaaaaccgca    1800
gcagggaggc aaacaatgat taattaacta gagcggccgc caccgcggcc cgagattccg    1860
gcctcttcgg ccgccaagcg acccgggtgg acgtctagag gtacctagca attaacagat    1920
agtttgccgg tgataattct cttaacctcc cacactcctt tgacataacg atttatgtaa    1980
cgaaactgaa atttgaccag atattgtgtc cgcggtggag ctccagcttt tgttcccttt    2040
agtgagggtt aatttcgagc ttggcgtaat catggtcata gctgtttcct gtgtgaaatt    2100
gttatccgct cacaattcca cacaacatac gagccggaag cataaagtgt aaagcctggg    2160
gtgcctaatg agtgagctaa ctcacattaa ttgcgttgcg ctcactgccc gctttccagt    2220
cgggaaacct gtcgtgccag ctgcattaat gaatcggcca acgcgcgggg agaggcggtt    2280
tgcgtattgg gcgctcttcc gcttcctcgc tcactgactc gctgcgctcg gtcgttcggc    2340
tgcggcgagc ggtatcagct cactcaaagg cggtaatacg ttatccaca gaatcagggg    2400 ataacgcagg aaagaacatg tgagcaaaag gccagcaaaa ggccaggaac cgtaaaaagg    2460
ccgcgttgct ggcgtttttc cataggctcc gcccccctga cgagcatcac aaaaatcgac    2520
gctcaagtca gaggtggcga aacccgacag gactataaag ataccaggcg tttcccctg    2580 gaagctccct cgtgcgctct cctgttccga ccctgccgct taccggatac ctgtccgcct    2640
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccgt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaccagc    3420 cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
```

```
gcccggcgtc aatacgggat aataccgcgc cacatagcag aactttaaaa gtgctcatca   3900
ttggaaaacg ttcttcgggg cgaaaactct caaggatctt accgctgttg agatccagtt   3960
cgatgtaacc cactcgtgca cccaactgat cttcagcatc ttttactttc accagcgttt   4020
ctgggtgagc aaaaacagga aggcaaaatg ccgcaaaaaa gggaataagg gcgacacgga   4080
aatgttgaat actcatactc ttcctttttc aatattattg aagcatttat cagggttatt   4140
gtctcatgag cggatacata tttgaatgta tttagaaaaa taaacaaata ggggttccgc   4200
gcacatttcc ccgaaaagtg ccacctgacg cgccctgtag cggcgcatta agcgcggcgg   4260
gtgtggtggt tacgcgcagc gtgaccgcta cacttgccag cgccctagcg cccgctcctt   4320
tcgctttctt cccttccttt ctcgccacgt tcgccggctt tccccgtcaa gctctaaatc   4380
gggggctccc tttagggttc cgatttagtg ctttacggca cctcgacccc aaaaaacttg   4440
attagggtga tggttcacgt agtgggccat cgccctgata gacggttttt cgccctttga   4500
cgttggagtc cacgttcttt aatagtggac tcttgttcca aactgaaaca cactcaacc    4560
ctatctcggt ctattctttt gatttataag ggattttgcc gatttcggcc tattggttaa   4620
aaaatgagct gatttaacaa aaatttaacg cgaattttaa caaatatta acgcttacaa    4680
tttccattcg ccattcaggc tgcgcaactg ttgggaaggg cgatcggtgc gggcctcttc   4740
gctattacgc cagctggcga aaggggatg tgctgcaagg cgattaagtt gggtaacgcc    4800
agggttttcc cagtcacgac gttgtaaaac gacggccagt gaattgtaat acgactcact   4860
atagggcgaa ttgggtaccg gccccccct cgaggtcgat ggtgtcgata agcttgatat    4920
cgaattcatg tcacacaaac cgatcttcgc ctcaaggaaa cctaattcta catccgagag   4980
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaaat atggatagca taaatgatat   5400
ctgcattgcc taattcgaaa tcaacagcaa cgaaaaaaat ccttgtaca acataaaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aagtatata tttatttctt gttatataat cctttgttt attacatggg     5820
ctggatacat aaaggtattt tgatttaatt ttttgcttaa attcaatccc cctcgttca     5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacattttt gcttttacaa   6060
gtacaagtac atcgtacaac tatgtactac tgttgatgca tccacaacag tttgttttgt   6120
ttttttttgt ttttttttt tctaatgatt cattaccgct atgtatacct acttgtactt     6180
```

```
gtagtaagcc gggttattgg cgttcaatta atcatagact tatgaatctg cacggtgtgc    6240
gctgcgagtt acttttagct tatgcatgct acttgggtgt aatattggga tctgttcgga    6300
aatcaacgga tgctcaaccg atttcgacag taataatttg aatcgaatcg gagcctaaaa    6360
tgaacccgag tatatctcat aaaattctcg gtgagaggtc tgtgactgtc agtacaaggt    6420
gccttcatta tgccctcaac cttaccatac ctcactgaat gtagtgtacc tctaaaaatg    6480
aaatacagtg ccaaaagcca aggcactgag ctcgtctaac ggacttgata tacaaccaat    6540
taaaacaaat gaaagaaat acagttcttt gtatcatttg taacaattac cctgtacaaa     6600
ctaaggtatt gaaatcccac aatattccca aagtccaccc ctttccaaat tgtcatgcct    6660
acaactcata taccaagcac taacctacca aacaccacta aaacccccaca aaatatatct   6720
taccgaatat acagtaacaa gctaccacca cactcgttgg gtgcagtcgc cagcttaaag    6780
atatctatcc acatcagcca caactccctt cctttaataa accgactaca cccttggcta    6840
ttgaggttat gagtgaatat actgtagaca agacactttc aagaagactg tttccaaaac    6900
gtaccactgt cctccactac aaacacaccc aatctgcttc ttctagtcaa ggttgctaca    6960
ccggtaaatt ataaatcatc atttcattag cagggcaggg cccttttat agagtcttat     7020
acactagcgg accctgccgg tagaccaacc cgcaggcgcg tcagtttgct ccttccatca    7080
atgcgtcgta gaaacgactt actccttctt gagcagctcc ttgaccttgt tggcaacaag    7140
tctccgacct cggaggtgga ggaagagcct ccgatatcgg cggtagtgat accagcctcg    7200
acggactcct tgacggcagc ctcaacagcg tcaccggcgg gcttcatgtt aagagagaac    7260
ttgagcatca tggcggcaga cagaatggtg gcaatggggt tgaccttctg cttgccgaga    7320
tcggggggcag atccgtgaca gggctcgtac agaccgaacg cctcgttggt gtcgggcaga   7380
gaagccagag aggcggaggg cagcagaccc agagaaccgg ggatgacgga ggcctcgtcg    7440
gagatgatat cgccaaacat gttggtggtg atgatgatac cattcatctt ggagggctgc    7500
ttgatgagga tcatgcggc cgagtcgatc agctggtggt tgagctcgag ctgggggaat    7560
tcgtccttga ggactcgagt gacagtcttt cgccaaagtc gagaggaggc cagcacgttg    7620
gccttgtcaa gagaccacac gggaagaggg gggttgtgct gaagggccag gaaggcggcc    7680
attcgggcaa ttcgctcaac ctcaggaacg gagtaggtct cggtgtcgga agcgacgcca    7740
gatccgtcat cctcctttcg ctctccaaag tagatacctc cgacgagctc tcggacaatg    7800
atgaagtcgg tgccctcaac gtttcggatg ggggagagat cggcgagctt gggcgacagc    7860
agctggcagg gtcgcaggtt ggcgtacagg ttcaggtcct ttcgcagctt gaggagaccc    7920
tgctcgggtc gcacgtcggt tcgtccgtcg ggagtggtcc atacggtgtt ggcagcgcct    7980
ccgacagcac cgagcataat agagtcagcc tttcggcaga tgtcgagagt agcgtcggtg    8040
atgggctcgc cctccttctc aatggcagct cctccaatga gtcggtcctc aaacacaaac    8100
tcggtgccgg aggcctcagc aacagacttg agcaccttga cggcctcggc aatcacctcg    8160
gggccacaga agtcgccgcc gagaagaaca atcttcttgg agtcagtctt ggtcttctta    8220
gtttcgggtt ccattgtgga tgtgtgtggt tgtatgtgtg atgtggtgtg tggagtgaaa    8280
atctgtggcg gcaaacgct cttgtatata tacgcacttt tgcccgtgct atgtggaaga     8340
ctaaacctcc gaagattgtg actcaggtag tgcggtatcg gctagggacc caaaccttgt    8400
cgatgccgat agcgctatcg aacgtacccc agccggccgg gagtatgtcg gagggacat    8460
acgagatcgt caagggtttg tggccaactg gtaaataaat gatgtcgacg tttaaacgaa    8520
ttcgcccttt ccaatcgatt gattcgactg gaaacacaag atgaagatgg ctgatcggtt    8580
```

```
catctgcttg acttacattc tggatatata cgagtcgcag tgtgagttcc gactcagact    8640
ggggaggatg cgaccagatc gaaatccagg gcaggttcta caccttgcag agtggagctg    8700
tctcccattt ccaagtccag agtgtggacg ttcgggcttt tcgagaatgt cgagcagaaa    8760
cagggtcgag ttggcgcata agtaccctct ttcgatctgt ttaacctgga gttggggtgt    8820
tattttggat tatgataaaa aagaaagaat gaaaaaaaa gaaaaaaaa gaaaaaaag     8880 aaaaaaaag aaaaagaag acagtgacaa ttagcatcca accataagag cgacacaaga    8940
gactcgaact cagaacactt gtatctggcc acatgtgctt cgtctctcag tctctccatc    9000
gcttctaaat taccccaaca tgtgccaaag ttcaatgcta gacagcaata gggttccccc    9060
cacaatcttg ggcagatgag agtggggcgg aggagatgtc atggtcaatt gtggcgtcaa    9120
tggagcgttt aatgggccca aaagttgata gggtcgttca ttgacagatt aggattgtag    9180
cggtcaaaag accccccga aaagtccct cgacactctc tctaccatct ccccaaaatc     9240
gccttcatgt gataaactct agcgcggggc cgttactcta acgaacttag agacattcac    9300
atgcggaggt accgtagcta caagtaccag tagaggaagt ccaagtggat aaatcgtctt    9360
cccgaatacc gactttctc accaccaatt gc                                   9392

<210> SEQ ID NO 16
<211> LENGTH: 716
<212> TYPE: DNA
<213> ORGANISM: Yarrowia lipolytica

<400> SEQUENCE: 16
ctacaccttg cagagtggag ctgtctccca tttccaagtc cagagtgtgg acgttcgggc      60
ttttcgagaa tgtcgagcag aaacagggtc gagttggcgc ataagtaccc tctttcgatc    120
tgtttaacct ggagttgggg tgttattttg gattatgata aaaagaaag aatgaaaaaa     180 aaagaaaaaa aagaaaaaa aagaaaaaaa agaaaaaag aagacagtga caattagcat     240
ccaaccataa gagcgacaca agagactcga actcagaaca cttgtatctg gccacatgtg    300
cttcgtctct cagtctctcc atcgcttcta aattacccca acatgtgcca aagttcaatg    360
ctagacagca atagggttcc ccccacaatc ttgggcagat gagagtgggg cggaggagat    420
gtcatggtca attgtggcgt caatggagcg tttaatgggc ccaaaagttg atagggtcgt    480
tcattgacag attaggattg tagcggtcaa aagaaccccc cgaaaagtc cctcgacact    540 ctctctacca tctccccaaa atcgccttca tgtgataaac tctagcgcgg ggccgttact    600
ctaacgaact tagagacatt cacatgcgga ggtaccgtag ctacaagtac cagtagagga    660
agtccaagtg gataaatcgt cttcccgaat accgactttt ctcaccacca attgcc        716

<210> SEQ ID NO 17
<211> LENGTH: 9231
<212> TYPE: DNA
<213> ORGANISM: Artificial Sequence
<220> FEATURE:
<223> OTHER INFORMATION: Plasmid

<400> SEQUENCE: 17
catggcatgg atggtacgtc ctgtagaaac cccaacccgt gaaatcaaaa aactcgacgg      60
cctgtgggca ttcagtctgg atcgcgaaaa ctgtggaatt gatcagcgtt ggtgggaaag    120
cgcgttacaa gaaagccggg caattgctgt gccaggcagt tttaacgatc agttcgccga    180
tgcagatatt cgtaattatg cgggcaacgt ctggtatcag cgcgaagtct ttataccgaa    240
```

```
aggttgggca ggccagcgta tcgtgctgcg tttcgatgcg gtcactcatt acggcaaagt    300
gtgggtcaat aatcaggaag tgatggagca tcagggcggc tatacgccat ttgaagccga    360
tgtcacgccg tatgttattg ccgggaaaag tgtacgtatc accgtttgtg tgaacaacga    420
actgaactgg cagactatcc cgccgggaat ggtgattacc gacgaaaacg gcaagaaaaa    480
gcagtcttac ttccatgatt tctttaacta tgccgggatc catcgcagcg taatgctcta    540
caccacgccg aacacctggg tggacgatat caccgtggtg acgcatgtcg cgcaagactg    600
taaccacgcg tctgttgact ggcaggtggt ggccaatggt gatgtcagcg ttgaactgcg    660
tgatgcggat caacaggtgg ttgcaactgg acaaggcact agcgggactt tgcaagtggt    720
gaatccgcac ctctggcaac cgggtgaagg ttatctctat gaactgtgcg tcacagccaa    780
aagccagaca gagtgtgata tctacccgct tcgcgtcggc atccggtcag tggcagtgaa    840
gggcgaacag ttcctgatta accacaaacc gttctacttt actggctttg gtcgtcatga    900
agatgcggac ttacgtggca aaggattcga taacgtgctg atggtgcacg accacgcatt    960
aatggactgg attggggcca actcctaccg tacctcgcat tacccttacg ctgaagagat   1020
gctcgactgg gcagatgaac atggcatcgt ggtgattgat gaaactgctg ctgtcggctt   1080
taacctctct ttaggcattg gtttcgaagc gggcaacaag ccgaaagaac tgtacagcga   1140
agaggcagtc aacggggaaa ctcagcaagc gcacttacag gcgattaaag agctgatagc   1200
gcgtgacaaa aaccacccaa gcgtggtgat gtggagtatt ccaacgaac cggatacccg    1260 tccgcaagtg cacgggaata tttcgccact ggcggaagca acgcgtaaac tcgacccgac   1320
gcgtccgatc acctgcgtca atgtaatgtt ctgcgacgct cacaccgata ccatcagcga   1380
tctctttgat gtgctgtgcc tgaaccgtta ttacggatgg tatgtccaaa gcggcgattt   1440
ggaaacggca gagaaggtac tggaaaaaga acttctggcc tggcaggaga aactgcatca   1500
gccgattatc atcaccgaat acggcgtgga tacgttagcc gggctgcact caatgtacac   1560
cgacatgtgg agtgaagagt atcagtgtgc atggctggat atgtatcacc gcgtctttga   1620
tcgcgtcagc gccgtcgtcg gtgaacaggt atggaatttc gccgattttg cgacctcgca   1680
aggcatattg cgcgttggcg gtaacaagaa agggatcttc actcgcgacc gcaaaccgaa   1740
gtcggcggct tttctgctgc aaaaacgctg gactggcatg aacttcggtg aaaaaccgca   1800
gcagggaggc aaacaatgat taattaacta gagcggccgc caccgcggcc cgagattccg   1860
gcctcttcgg ccgccaagcg acccgggtgg acgtctagag gtacctagca attaacagat   1920
agtttgccgg tgataattct cttaacctcc cacactcctt tgacataacg atttatgtaa   1980
cgaaactgaa atttgaccag atattgtgtc cgcggtggag ctccagcttt tgttcccttt   2040
agtgagggtt aatttcgagc ttggcgtaat catggtcata gctgtttcct gtgtgaaatt   2100
gttatccgct cacaattcca cacaacatac gagccggaag cataaagtgt aaagcctggg   2160
gtgcctaatg agtgagctaa ctcacattaa ttgcgttgcg ctcactgccc gctttccagt   2220
cgggaaacct gtcgtgccag ctgcattaat gaatcggcca acgcgcgggg agaggcggtt   2280
tgcgtattgg gcgctcttcc gcttcctcgc tcactgactc gctgcgctcg gtcgttcggc   2340
tgcggcgagc ggtatcagct cactcaaagg cggtaatacg gttatccaca gaatcagggg   2400
ataacgcagg aaagaacatg tgagcaaaag gccagcaaaa ggccaggaac cgtaaaaagg   2460
ccgcgttgct ggcgtttttc cataggctcc gcccccctga cgagcatcac aaaaatcgac   2520
gctcaagtca gaggtggcga aacccgacag gactataaag ataccaggcg tttccccctg   2580
gaagctccct cgtgcgctct cctgttccga cctgccgct taccggatac ctgtccgcct   2640
```

```
ttctcccttc gggaagcgtg gcgctttctc atagctcacg ctgtaggtat ctcagttcgg    2700
tgtaggtcgt tcgctccaag ctgggctgtg tgcacgaacc ccccgttcag cccgaccgct    2760
gcgccttatc cggtaactat cgtcttgagt ccaacccggt aagacacgac ttatcgccac    2820
tggcagcagc cactggtaac aggattagca gagcgaggta tgtaggcggt gctacagagt    2880
tcttgaagtg gtggcctaac tacggctaca ctagaaggac agtatttggt atctgcgctc    2940
tgctgaagcc agttaccttc ggaaaaagag ttggtagctc ttgatccggc aaacaaacca    3000
ccgctggtag cggtggtttt tttgtttgca agcagcagat tacgcgcaga aaaaaggat    3060 ctcaagaaga tcctttgatc ttttctacgg ggtctgacgc tcagtggaac gaaaactcac    3120
gttaagggat tttggtcatg agattatcaa aaaggatctt cacctagatc cttttaaatt    3180
aaaaatgaag ttttaaatca atctaaagta tatatgagta aacttggtct gacagttacc    3240
aatgcttaat cagtgaggca cctatctcag cgatctgtct atttcgttca tccatagttg    3300
cctgactccc cgtcgtgtag ataactacga tacgggaggg cttaccatct ggccccagtg    3360
ctgcaatgat accgcgagac ccacgctcac cggctccaga tttatcagca ataaaccagc    3420
cagccggaag ggccgagcgc agaagtggtc ctgcaacttt atccgcctcc atccagtcta    3480
ttaattgttg ccgggaagct agagtaagta gttcgccagt taatagtttg cgcaacgttg    3540
ttgccattgc tacaggcatc gtggtgtcac gctcgtcgtt tggtatggct tcattcagct    3600
ccggttccca acgatcaagg cgagttacat gatcccccat gttgtgcaaa aaagcggtta    3660
gctccttcgg tcctccgatc gttgtcagaa gtaagttggc cgcagtgtta tcactcatgg    3720
ttatggcagc actgcataat tctcttactg tcatgccatc cgtaagatgc ttttctgtga    3780
ctggtgagta ctcaaccaag tcattctgag aatagtgtat gcggcgaccg agttgctctt    3840
gcccggcgtc aatacgggat aataccgcgc cacatagcag aactttaaaa gtgctcatca    3900
ttggaaaacg ttcttcgggg cgaaaactct caaggatctt accgctgttg agatccagtt    3960
cgatgtaacc cactcgtgca cccaactgat cttcagcatc ttttactttc accagcgttt    4020
ctgggtgagc aaaaacagga aggcaaaatg ccgcaaaaaa gggaataagg gcgacacgga    4080
aatgttgaat actcatactc ttcctttttc aatattattg aagcatttat cagggttatt    4140
gtctcatgag cggatacata tttgaatgta tttagaaaaa taaacaaata ggggttccgc    4200
gcacatttcc ccgaaaagtg ccacctgacg cgccctgtag cggcgcatta agcgcggcgg    4260
gtgtggtggt tacgcgcagc gtgaccgcta cacttgccag cgccctagcg cccgctcctt    4320
tcgctttctt cccttccttt ctcgccacgt tcgccggctt tccccgtcaa gctctaaatc    4380
gggggctccc tttagggttc cgatttagtg ctttacggca cctcgacccc aaaaaacttg    4440
attagggtga tggttcacgt agtgggccat cgccctgata cggttttt cgcccttga    4500 cgttggagtc cacgttcttt aatagtggac tcttgttcca aactggaaca cactcaacc    4560 ctatctcggt ctattctttt gatttataag ggattttgcc gatttcggcc tattggttaa    4620
aaaatgagct gatttaacaa aaatttaacg cgaatttta caaaatatta acgcttacaa    4680
tttccattcg ccattcaggc tgcgcaactg ttgggaaggg cgatcggtgc gggcctcttc    4740
gctattacgc cagctggcga aaggggggatg tgctgcaagg cgattaagtt gggtaacgcc    4800
agggttttcc cagtcacgac gttgtaaaac gacggccagt gaattgtaat acgactcact    4860
atagggcgaa ttgggtaccg ggccccccct cgaggtcgat ggtgtcgata agcttgatat    4920
cgaattcatg tcacacaaac cgatcttcgc ctcaaggaaa cctaattcta catccgagag    4980
```

```
actgccgaga tccagtctac actgattaat tttcgggcca ataatttaaa aaaatcgtgt   5040
tatataatat tatatgtatt atatatatac atcatgatga tactgacagt catgtcccat   5100
tgctaaatag acagactcca tctgccgcct ccaactgatg ttctcaatat ttaaggggtc   5160
atctcgcatt gtttaataat aaacagactc catctaccgc ctccaaatga tgttctcaaa   5220
atatattgta tgaacttatt tttattactt agtattatta gacaacttac ttgctttatg   5280
aaaaacactt cctatttagg aaacaattta taatggcagt tcgttcattt aacaatttat   5340
gtagaataaa tgttataaat gcgtatggga atcttaaat atggatagca taaatgatat    5400
ctgcattgcc taattcgaaa tcaacagcaa cgaaaaaaat cccttgtaca acataaatag   5460
tcatcgagaa atatcaacta tcaaagaaca gctattcaca cgttactatt gagattatta   5520
ttggacgaga atcacacact caactgtctt tctctcttct agaaatacag gtacaagtat   5580
gtactattct cattgttcat acttctagtc atttcatccc acatattcct tggatttctc   5640
tccaatgaat gacattctat cttgcaaatt caacaattat aataagatat accaaagtag   5700
cggtatagtg gcaatcaaaa agcttctctg gtgtgcttct cgtatttatt tttattctaa   5760
tgatccatta aaggtatata tttatttctt gttatataat ccttttgttt attacatggg   5820
ctggatacat aaaggtattt tgatttaatt ttttgcttaa attcaatccc ccctcgttca   5880
gtgtcaactg taatggtagg aaattaccat acttttgaag aagcaaaaaa aatgaaagaa   5940
aaaaaaaatc gtatttccag gttagacgtt ccgcagaatc tagaatgcgg tatgcggtac   6000
attgttcttc gaacgtaaaa gttgcgctcc ctgagatatt gtacatttt gcttttacaa    6060 gtacaagtac atcgtacaac tatgtactac tgttgatgca tccacaacag tttgttttgt   6120
ttttttttgt ttttttttt tctaatgatt cattaccgct atgtatacct acttgtactt     6180
gtagtaagcc gggttattgg cgttcaatta atcatagact tatgaatctg cacggtgtgc   6240
gctgcgagtt acttttagct tatgcatgct acttgggtgt aatattggga tctgttcgga   6300
aatcaacgga tgctcaaccg atttcgacag taataaatttg aatcgaatcg gagcctaaaa   6360
tgaacccgag tatatctcat aaaattctcg gtgagaggtc tgtgactgtc agtacaaggt   6420
gccttcatta tgccctcaac cttaccatac ctcactgaat gtagtgtacc tctaaaaatg   6480
aaatacagtg ccaaaagcca aggcactgag ctcgtctaac ggacttgata tacaaccaat   6540
taaaacaaat gaaagaaat acagttcttt gtatcatttg taacaattac cctgtacaaa    6600
ctaaggtatt gaaatcccac aatattccca aagtccaccc ctttccaaat tgtcatgcct   6660
acaactcata taccaagcac taacctacca aacaccacta aaaccccaca aaatatatct   6720
taccgaatat acagtaacaa gctaccacca cactcgttgg gtgcagtcgc cagcttaaag   6780
atatctatcc acatcagcca caactccctt cctttaataa accgactaca cccttggcta   6840
ttgaggttat gagtgaatat actgtagaca agacactttc aagaagactg tttccaaaac   6900
gtaccactgt cctccactac aaacacaccc aatctgcttc ttctagtcaa ggttgctaca   6960
ccggtaaatt ataaatcatc atttcattag cagggcaggg ccctttttat agagtcttat   7020
acactagcgg accctgccgg tagaccaacc cgcaggcgcg tcagtttgct ccttccatca   7080
atgcgtcgta gaaacgactt actccttctt gagcagctcc ttgaccttgt tggcaacaag   7140
tctccgacct cggaggtgga ggaagagcct ccgatatcgg cggtagtgat accagcctcg   7200
acggactcct tgacggcagc ctcaacagcg tcaccggcgg gcttcatgtt aagagagaac   7260
ttgagcatca tggcggcaga cagaatggtg gcaatggggt tgaccttctg cttgccgaga   7320 tcggggggcag atccgtgaca gggctcgtac agaccgaacg cctcgttggt gtcgggcaga   7380
```

-continued

```
gaagccagag aggcggaggg cagcagaccc agagaaccgg ggatgacgga ggcctcgtcg      7440
gagatgatat cgccaaacat gttggtggtg atgatgatac cattcatctt ggagggctgc      7500
ttgatgagga tcatggcggc cgagtcgatc agctggtggt tgagctcgag ctgggggaat      7560
tcgtccttga ggactcgagt gacagtcttt cgccaaagtc gagaggaggc cagcacgttg      7620
gccttgtcaa gagaccacac gggaagaggg gggttgtgct gaagggccag gaaggcggcc      7680
attcgggcaa ttcgctcaac ctcaggaacg gagtaggtct cggtgtcgga agcgacgcca      7740
gatccgtcat cctcctttcg ctctccaaag tagatacctc cgacgagctc tcggacaatg      7800
atgaagtcgg tgccctcaac gtttcggatg gggagagat cggcgagctt gggcgacagc       7860
agctggcagg gtcgcaggtt ggcgtacagg ttcaggtcct ttcgcagctt gaggagaccc      7920
tgctcgggtc gcacgtcggt tcgtccgtcg ggagtggtcc atacggtgtt ggcagcgcct      7980
ccgacagcac cgagcataat agagtcagcc tttcggcaga tgtcgagagt agcgtcggtg      8040
atgggctcgc cctccttctc aatggcagct cctccaatga gtcggtcctc aaacacaaac      8100
tcggtgccgg aggcctcagc aacagacttg agcaccttga cggcctcggc aatcacctcg      8160
gggccacaga gtcgccgcc gagaagaaca atcttcttgg agtcagtctt ggtcttctta       8220
gtttcgggtt ccattgtgga tgtgtgtggt tgtatgtgtg atgtggtgtg tggagtgaaa      8280
atctgtggct ggcaaacgct cttgtatata tacgcacttt tgcccgtgct atgtggaaga      8340
ctaaacctcc gaagattgtg actcaggtag tgcggtatcg gctagggacc caaaccttgt      8400
cgatgccgat agcgctatcg aacgtacccc agccggccgg gagtatgtcg gagggagcat     8460
acgagatcgt caagggtttg tggccaactg gtaaataaat gatgtcgacg tttaaactac      8520
accttgcaga gtggagctgt ctcccatttc caagtccaga gtgtggacgt tcgggctttt      8580
cgagaatgtc gagcagaaac agggtcgagt tggcgcataa gtaccctctt tcgatctgtt      8640
taacctggag ttggggtgtt attttggatt atgataaaaa agaaagaatg aaaaaaaaag      8700
aaaaaaaaag aaaaaaaaga aaaaaaaaga aaaagaaga cagtgacaat tagcatccaa       8760
ccataagagc gacacaagag actcgaactc agaacacttg tatctggcca catgtgcttc      8820
gtctctcagt ctctccatcg cttctaaatt accccaacat gtgccaaagt tcaatgctag      8880
acagcaatag ggttccccc caatcttgg gcagatgaga gtgggcgga ggagatgtca        8940 tggtcaattg tggcgtcaat ggagcgttta atgggcccaa aagttgatag ggtcgttcat      9000
tgacagatta ggattgtagc ggtcaaaaga accccccgaa aaagtccctc gacactctct      9060
ctaccatctc cccaaaatcg ccttcatgtg ataaactcta gcgcgggcc gttactctaa       9120 cgaacttaga gacattcaca tgcggaggta ccgtagctac aagtaccagt agaggaagtc      9180
caagtggata aatcgtcttc ccgaataccg acttttctca ccaccaattg c               9231
```

<210> SEQ ID NO 18
<211> LENGTH: 39
<212> TYPE: DNA
<213> ORGANISM: Artificial Sequence
<220> FEATURE:
<223> OTHER INFORMATION: Primer

<400> SEQUENCE: 18

```
caacatgtgc caaagtttaa acaatgctag acagcaata                              39
```

<210> SEQ ID NO 19
<211> LENGTH: 39
<212> TYPE: DNA

```
<213> ORGANISM: Artificial Sequence
<220> FEATURE:
<223> OTHER INFORMATION: Primer

<400> SEQUENCE: 19
tattgctgtc tagcattgtt taaactttgg cacatgttg                    39

<210> SEQ ID NO 20
<211> LENGTH: 9226
<212> TYPE: DNA
<213> ORGANISM: Artificial Sequence
<220> FEATURE:
<223> OTHER INFORMATION: Plasmid

<400> SEQUENCE: 20
```

| | | | | | |
|---|---|---|---|---|---|
| aaactacacc | ttgcagagtg | gagctgtctc | ccatttccaa | gtccagagtg | tggacgttcg | 60 |
| ggcttttcga | gaatgtcgag | cagaaacagg | gtcgagttgg | cgcataagta | ccctctttcg | 120 |
| atctgtttaa | cctggagttg | gggtgttatt | ttggattatg | ataaaaaaga | aagaatgaaa | 180 |
| aaaaagaaa | aaaaagaaa | aaaaagaaaa | aaaaagaaaa | aagaagacag | tgacaattag | 240 |
| catccaacca | taagagcgac | acaagagact | cgaactcaga | acacttgtat | ctggccacat | 300 |
| gtgcttcgtc | tctcagtctc | tccatcgctt | ctaaattacc | ccaacatgtg | ccaaagttta | 360 |
| aacaatgcta | gacagcaata | gggttccccc | cacaatcttg | ggcagatgag | agtggggcgg | 420 |
| aggagatgtc | atggtcaatt | gtggcgtcaa | tggagcgttt | aatgggccca | aaagttgata | 480 |
| gggtcgttca | ttgacagatt | aggattgtag | cggtcaaaag | aacccccga | aaaagtccct | 540 |
| cgacactctc | tctaccatct | ccccaaaatc | gccttcatgt | gataaactct | agcgcgggc | 600 |
| cgttactcta | acgaacttag | agacattcac | atgcggaggt | accgtagcta | caagtaccag | 660 |
| tagaggaagt | ccaagtggat | aaatcgtctt | cccgaatacc | gacttttctc | accaccaatt | 720 |
| gccatggtac | gtcctgtaga | aaccccaacc | cgtgaaatca | aaaaactcga | cggcctgtgg | 780 |
| gcattcagtc | tggatcgcga | aaactgtgga | attgatcagc | gttggtggga | aagcgcgtta | 840 |
| caagaaagcc | gggcaattgc | tgtgccaggc | agttttaacg | atcagttcgc | cgatgcagat | 900 |
| attcgtaatt | atgcgggcaa | cgtctggtat | cagcgcgaag | tctttatacc | gaaaggttgg | 960 |
| gcaggccagc | gtatcgtgct | gcgtttcgat | gcggtcactc | attacggcaa | agtgtgggtc | 1020 |
| aataatcagg | aagtgatgga | gcatcagggc | ggctatacgc | catttgaagc | cgatgtcacg | 1080 |
| ccgtatgtta | ttgccgggaa | aagtgtacgt | atcaccgttt | gtgtgaacaa | cgaactgaac | 1140 |
| tggcagacta | tcccgccggg | aatggtgatt | accgacgaaa | acggcaagaa | aaagcagtct | 1200 |
| tacttccatg | atttctttaa | ctatgccggg | atccatcgca | gcgtaatgct | ctacaccacg | 1260 |
| ccgaacacct | gggtggacga | tatcaccgtg | gtgacgcatg | tcgcgcaaga | ctgtaaccac | 1320 |
| gcgtctgttg | actggcaggt | ggtggccaat | ggtgatgtca | gcgttgaact | gcgtgatgcg | 1380 |
| gatcaacagg | tggttgcaac | tggacaaggc | actagcggga | cttttcaagt | ggtgaatccg | 1440 |
| cacctctggc | aaccgggtga | aggttatctc | tatgaactgt | gcgtcacagc | caaaagccag | 1500 |
| acagagtgtg | atatctaccc | gcttcgcgtc | ggcatccggt | cagtggcagt | gaagggcgaa | 1560 |
| cagttcctga | ttaaccacaa | accgttctac | tttactggct | ttggtcgtca | tgaagatgcg | 1620 |
| gacttacgtg | gcaaaggatt | cgataacgtg | ctgatggtgc | acgaccacgc | attaatggac | 1680 |
| tggattgggg | ccaactccta | ccgtacctcg | cattacccttt | acgctgaaga | gatgctcgac | 1740 |
| tgggcagatg | aacatggcat | cgtggtgatt | gatgaaactg | ctgctgtcgg | ctttaacctc | 1800 |
| tctttaggca | ttggtttcga | agcgggcaac | aagccgaaag | aactgtacag | cgaagaggca | 1860 |

```
gtcaacgggg aaactcagca agcgcactta caggcgatta aagagctgat agcgcgtgac   1920
aaaaaccacc caagcgtggt gatgtggagt attgccaacg aaccggatac ccgtccgcaa   1980
gtgcacggga atatttcgcc actggcggaa gcaacgcgta aactcgaccc gacgcgtccg   2040
atcacctgcg tcaatgtaat gttctgcgac gctcacaccg ataccatcag cgatctcttt   2100
gatgtgctgt gcctgaaccg ttattacgga tggtatgtcc aaagcggcga tttggaaacg   2160
gcagagaagg tactggaaaa agaacttctg gcctggcagg agaaactgca tcagccgatt   2220
atcatcaccg aatacggcgt ggatacgtta gccgggctgc actcaatgta caccgacatg   2280
tggagtgaag agtatcagtg tgcatggctg gatatgtatc accgcgtctt tgatcgcgtc   2340
agcgccgtcg tcggtgaaca ggtatggaat tcgccgattt tgcgacctc  gcaaggcata   2400 ttgcgcgttg gcggtaacaa gaaagggatc ttcactcgcg accgcaaacc gaagtcggcg   2460
gcttttctgc tgcaaaaacg ctggactggc atgaacttcg gtgaaaaacc gcagcaggga   2520
ggcaaacaat gattaattaa ctagagcggc cgccaccgcg gcccgagatt ccggcctctt   2580
cggccgccaa gcgacccggg tggacgtcta gaggtaccta gcaattaaca gatagtttgc   2640
cggtgataat tctcttaacc tcccacactc ctttgacata acgatttatg taacgaaact   2700
gaaatttgac cagatattgt gtccgcggtg gagctccagc ttttgttccc tttagtgagg   2760
gttaatttcg agcttggcgt aatcatggtc atagctgttt cctgtgtgaa attgttatcc   2820
gctcacaatt ccacacaaca tacgagccgg aagcataaag tgtaaagcct ggggtgccta   2880
atgagtgagc taactcacat taattgcgtt gcgctcactg cccgctttcc agtcgggaaa   2940
cctgtcgtgc cagctgcatt aatgaatcgg ccaacgcgcg gggagaggcg gtttgcgtat   3000
tgggcgctct tccgcttcct cgctcactga ctcgctgcgc tcggtcgttc ggctgcggcg   3060
agcggtatca gctcactcaa aggcggtaat acggttatcc acagaatcag gggataacgc   3120
aggaaagaac atgtgagcaa aaggccagca aaaggccagg aaccgtaaaa aggccgcgtt   3180
gctggcgttt ttccataggc tccgcccccc tgacgagcat cacaaaaatc gacgctcaag   3240
tcagaggtgg cgaaacccga caggactata aagataccag gcgtttcccc ctggaagctc   3300
cctcgtgcgc tctcctgttc cgaccctgcc gcttaccgga tacctgtccg cctttctccc   3360
ttcgggaagc gtggcgcttt ctcatagctc acgctgtagg tatctcagtt cggtgtaggt   3420
cgttcgctcc aagctgggct gtgtgcacga accccccgtt cagcccgacc gctgcgcctt   3480
atccggtaac tatcgtcttg agtccaaccc ggtaagacac gacttatcgc cactggcagc   3540
agccactggt aacaggatta gcagagcgag gtatgtaggc ggtgctacag agttcttgaa   3600
gtggtggcct aactacggct acactagaag gacagtattt ggtatctgcg ctctgctgaa   3660
gccagttacc ttcggaaaaa gagttggtag ctcttgatcc ggcaaacaaa ccaccgctgg   3720
tagcggtggt ttttttgttt gcaagcagca gattacgcgc agaaaaaaag gatctcaaga   3780
agatcctttg atcttttcta cggggtctga cgctcagtgg aacgaaaact cacgttaagg   3840
gattttggtc atgagattat caaaaaggat cttcacctag atccttttaa attaaaaatg   3900
aagttttaaa tcaatctaaa gtatatatga gtaaacttgg tctgacagtt accaatgctt   3960
aatcagtgag gcacctatct cagcgatctg tctatttcgt tcatccatag ttgcctgact   4020
ccccgtcgtg tagataacta cgatacggga gggcttacca tctggcccca gtgctgcaat   4080
gataccgcga gacccacgct caccggctcc agatttatca gcaataaacc agccagccgg   4140
aagggccgag cgcagaagtg gtcctgcaac tttatccgcc tccatccagt ctattaattg   4200
```

```
ttgccgggaa gctagagtaa gtagttcgcc agttaatagt ttgcgcaacg ttgttgccat   4260
tgctacaggc atcgtggtgt cacgctcgtc gtttggtatg gcttcattca gctccggttc   4320
ccaacgatca aggcgagtta catgatcccc catgttgtgc aaaaaagcgg ttagctcctt   4380
cggtcctccg atcgttgtca gaagtaagtt ggccgcagtg ttatcactca tggttatggc   4440
agcactgcat aattctctta ctgtcatgcc atccgtaaga tgcttttctg tgactggtga   4500
gtactcaacc aagtcattct gagaatagtg tatgcggcga ccgagttgct cttgcccggc   4560
gtcaatacgg gataataccg cgccacatag cagaacttta aaagtgctca tcattggaaa   4620
acgttcttcg gggcgaaaac tctcaaggat cttaccgctg ttgagatcca gttcgatgta   4680
acccactcgt gcacccaact gatcttcagc atctttact ttcaccagcg tttctgggtg   4740
agcaaaaaca ggaaggcaaa atgccgcaaa aaagggaata agggcgacac ggaaatgttg   4800
aatactcata ctcttccttt tcaatatta ttgaagcatt tatcagggtt attgtctcat   4860
gagcggatac atatttgaat gtatttagaa aaataaacaa ataggggttc gcgcacatt    4920
tccccgaaaa gtgccacctg acgcgccctg tagcggcgca ttaagcgcgg cgggtgtggt   4980
ggttacgcgc agcgtgaccg ctacacttgc cagcgcccta gcgcccgctc ctttcgcttt   5040
cttcccttcc tttctcgcca cgttcgccgg ctttccccgt caagctctaa atcggggggct  5100
cccctttaggg ttccgattta gtgctttacg gcacctcgac cccaaaaac ttgattaggg   5160
tgatggttca cgtagtgggc catcgccctg atagacggtt tttcgccctt tgacgttgga   5220
gtccacgttc tttaatagtg gactcttgtt ccaaactgga acaacactca accctatctc   5280
ggtctattct tttgatttat aagggatttt gccgatttcg gcctattggt taaaaaatga   5340
gctgatttaa caaaaattta acgcgaattt taacaaaata ttaacgctta caatttccat   5400
tcgccattca ggctgcgcaa ctgttgggaa gggcgatcgg tgcgggcctc ttcgctatta   5460
cgccagctgg cgaaagggggg atgtgctgca aggcgattaa gttgggtaac gccagggttt   5520
tcccagtcac gacgttgtaa aacgacggcc agtgaattgt aatacgactc actatagggc   5580
gaattgggta ccgggccccc cctcgaggtc gatggtgtcg ataagcttga tatcgaattc   5640
atgtcacaca aaccgatctt cgcctcaagg aaacctaatt ctacatccga gagactgccg   5700
agatccagtc tacactgatt aattttcggg ccaataattt aaaaaaatcg tgttatataa   5760
tattatatgt attatatata tacatcatga tgatactgac agtcatgtcc cattgctaaa   5820
tagacagact ccatctgccg cctccaactg atgttctcaa tatttaaggg gtcatctcgc   5880
attgtttaat aataaacaga ctccatctac cgcctccaaa tgatgttctc aaaatatatt   5940
gtatgaactt atttttatta cttagtatta ttagacaact tacttgcttt atgaaaaaca   6000
cttcctattt aggaaacaat ttataatggc agttcgttca tttaacaatt tatgtagaat   6060
aaatgttata aatgcgtatg ggaaatctta aatatggata gcataaatga tatctgcatt   6120
gcctaattcg aaatcaacag caacgaaaaa aatcccttgt acaacataaa tagtcatcga   6180
gaaatatcaa ctatcaaaga acagctattc acacgttact attgagatta ttattggacg   6240
agaatcacac actcaactgt ctttctctct tctagaaata caggtacaag tatgtactat   6300
tctcattgtt catacttcta gtcatttcat cccacatatt ccttggattt ctctccaatg   6360
aatgacattc tatcttgcaa attcaacaat tataataaga tataccaaag tagcggtata   6420
gtggcaatca aaaagcttct ctggtgtgct tctcgtattt attttattc taatgatcca   6480
ttaaaggtat atatttattt cttgttatat aatccttttg tttattacat gggctggata   6540
cataaaggta ttttgattta attttttgct taaattcaat ccccctcgt tcagtgtcaa    6600
```

```
ctgtaatggt aggaaattac catacttttg aagaagcaaa aaaaatgaaa gaaaaaaaaa    6660
atcgtatttc caggttagac gttccgcaga atctagaatg cggtatgcgg tacattgttc    6720
ttcgaacgta aaagttgcgc tccctgagat attgtacatt tttgctttta caagtacaag    6780
tacatcgtac aactatgtac tactgttgat gcatccacaa cagtttgttt tgttttttt    6840 tgttttttt ttttctaatg attcattacc gctatgtata cctacttgta cttgtagtaa    6900
gccgggttat tggcgttcaa ttaatcatag acttatgaat ctgcacggtg tgcgctgcga    6960
gttactttta gcttatgcat gctacttggg tgtaatattg ggatctgttc ggaaatcaac    7020
ggatgctcaa ccgatttcga cagtaataat ttgaatcgaa tcggagccta aaatgaaccc    7080
gagtatatct cataaaattc tcggtgagag gtctgtgact gtcagtacaa ggtgccttca    7140
ttatgccctc aaccttacca tacctcactg aatgtagtgt acctctaaaa atgaaataca    7200
gtgccaaaag ccaaggcact gagctcgtct aacggacttg atatacaacc aattaaaaca    7260
aatgaaaaga aatacagttc tttgtatcat ttgtaacaat taccctgtac aaactaaggt    7320
attgaaatcc cacaatattc ccaaagtcca cccctttcca aattgtcatg cctacaactc    7380
atataccaag cactaaccta ccaaacacca ctaaaacccc acaaaatata tcttaccgaa    7440
tatacagtaa caagctacca ccacactcgt tgggtgcagt cgccagctta aagatatcta    7500
tccacatcag ccacaactcc cttcctttaa taaaccgact acacccttgg ctattgaggt    7560
tatgagtgaa tatactgtag acaagacact ttcaagaaga ctgtttccaa aacgtaccac    7620
tgtcctccac tacaaacaca cccaatctgc ttcttctagt caaggttgct acaccggtaa    7680
attataaatc atcatttcat tagcagggca gggccctttt tatagagtct tatacactag    7740
cggaccctgc cggtagacca acccgcaggc gcgtcagttt gctccttcca tcaatgcgtc    7800
gtagaaacga cttactcctt cttgagcagc tccttgacct tgttggcaac aagtctccga    7860
cctcggaggt ggaggaagag cctccgatat cggcggtagt gataccagcc tcgacggact    7920
ccttgacggc agcctcaaca gcgtcaccgg cgggcttcat gttaagagag aacttgagca    7980
tcatggcggc agacagaatg gtggcaatgg ggttgacctt ctgcttgccg agatcggggg    8040
cagatccgtg acagggctcg tacagaccga acgcctcgtt ggtgtcgggc agagaagcca    8100
gagaggcgga gggcagcaga cccagagaac cggggatgac ggaggcctcg tcggagatga    8160
tatcgccaaa catgttggtg gtgatgatga taccattcat cttggagggc tgcttgatga    8220
ggatcatggc ggccgagtcg atcagctggt ggttgagctc gagctggggg aattcgtcct    8280
tgaggactcg agtgacagtc tttcgccaaa gtcgagagga ggccagcacg ttggccttgt    8340
caagagacca cacgggaaga ggggggttgt gctgaagggc caggaaggcg gccattcggg    8400
caattcgctc aacctcagga acggagtagg tctcggtgtc ggaagcgacg ccagatccgt    8460
catcctcctt tcgctctcca aagtagatac ctccgacgag ctctcggaca atgatgaagt    8520
cggtgccctc aacgtttcgg atggggagag atcggcgag cttgggcgac agcagctggc    8580
agggtcgcag gttggcgtac aggttcaggt cctttcgcag cttgaggaga ccctgctcgg    8640
gtcgcacgtc ggttcgtccg tcgggagtgg tccatacggt gttggcagcg cctccgacag    8700
caccgagcat aatagagtca gcctttcggc agatgtcgag agtagcgtcg gtgatgggct    8760
cgccctcctt ctcaatggca gctcctccaa tgagtcggtc ctcaaacaca aactcggtgc    8820
cggaggcctc agcaacagac ttgagcacct tgacggcctc ggcaatcacc tcggggccac    8880
agaagtcgcc gccgagaaga acaatcttct tggagtcagt cttggtcttc ttagtttcgg    8940
```

-continued

```
gttccattgt ggatgtgtgt ggttgtatgt gtgatgtggt gtgtggagtg aaaatctgtg    9000
gctggcaaac gctcttgtat atatacgcac ttttgcccgt gctatgtgga agactaaacc    9060
tccgaagatt gtgactcagg tagtgcggta tcggctaggg acccaaacct tgtcgatgcc    9120
gatagcgcta tcgaacgtac cccagccggc cgggagtatg tcggagggga catacgagat    9180
cgtcaagggt ttgtggccaa ctggtaaata aatgatgtcg acgttt                   9226
```

<210> SEQ ID NO 21
<211> LENGTH: 720
<212> TYPE: DNA
<213> ORGANISM: Yarrowia lipolytica

<400> SEQUENCE: 21

```
ctacaccttg cagagtggag ctgtctccca tttccaagtc cagagtgtgg acgttcgggc     60
ttttcgagaa tgtcgagcag aaacagggtc gagttggcgc ataagtaccc tctttcgatc    120
tgtttaacct ggagttgggg tgttattttg gattatgata aaaagaaag aatgaaaaaa     180 aaagaaaaaa aagaaaaaa aagaaaaaaa aagaaaaaag aagacagtga caattagcat    240
ccaaccataa gagcgacaca agagactcga actcagaaca cttgtatctg ccacatgtg    300 cttcgtctct cagtctctcc atcgcttcta aattacccca acatgtgcca agtttaaac    360 aatgctagac agcaataggg ttcccccac aatcttgggc agatgagagt ggggcggagg    420
agatgtcatg tcaattgtg gcgtcaatgg agcgtttaat gggcccaaaa gttgataggg    480
tcgttcattg acagattagg attgtagcgg tcaaagaac cccccgaaaa agtccctcga    540
cactctctct accatctccc caaaatcgcc ttcatgtgat aaactctagc gcggggccgt    600
tactctaacg aacttagaga cattcacatg cggaggtacc gtagctacaa gtaccagtag    660
aggaagtcca agtggataaa tcgtcttccc gaataccgac ttttctcacc accaattgcc    720
```

<210> SEQ ID NO 22
<211> LENGTH: 36
<212> TYPE: DNA
<213> ORGANISM: Artificial Sequence
<220> FEATURE:
<223> OTHER INFORMATION: Primer

<400> SEQUENCE: 22

```
cgtcaatgga gcgtttaaac tgggcccaaa agttga                               36
```

<210> SEQ ID NO 23
<211> LENGTH: 36
<212> TYPE: DNA
<213> ORGANISM: Artificial Sequence
<220> FEATURE:
<223> OTHER INFORMATION: Primer

<400> SEQUENCE: 23

```
tcaacttttg ggcccagttt aaacgctcca ttgacg                               36
```

<210> SEQ ID NO 24
<211> LENGTH: 9224
<212> TYPE: DNA
<213> ORGANISM: Artificial Sequence
<220> FEATURE:
<223> OTHER INFORMATION: Plasmid

<400> SEQUENCE: 24

```
aaactcacac ttgcagagtg gagctgtctc ccatttccaa gtccagagtg tggacgttcg     60
ggcttttcga gaatgtcgag cagaaacagg gtcgagttgg cgcataagta ccctctttcg    120
```

| | |
|---|---|
| atctgtttaa cctggagttg gggtgttatt ttggattatg ataaaaaga aagaatgaaa | 180 |
| aaaaagaaa aaaaagaaa aaaaagaaa aaaaagaaaa aagaagacag tgacaattag | 240 |
| catccaacca taagagcgac acaagagact cgaactcaga acacttgtat ctggccacat | 300 |
| gtgcttcgtc tctcagtctc tccatcgctt ctaaattacc ccaacatgtg ccaaagttca | 360 |
| atgctagaca gcaatagggt tcccccaca atcttgggca gatgagagtg gggcggagga | 420 |
| gatgtcatgg tcaattgtgg cgtcaatgga gcgtttaaac tgggcccaaa agttgatagg | 480 |
| gtcgttcatt gacagattag gattgtagcg gtcaaaagaa ccccccgaaa aagtccctcg | 540 |
| acactctctc taccatctcc ccaaaatcgc cttcatgtga taaactctag cgcggggccg | 600 |
| ttactctaac gaacttagag acattcacat gcggaggtac cgtagctaca agtaccagta | 660 |
| gaggaagtcc aagtggataa atcgtcttcc cgaataccga cttttctcac caccaattgc | 720 |
| catggtacgt cctgtagaaa ccccaacccg tgaaatcaaa aaactcgacg gcctgtgggc | 780 |
| attcagtctg gatcgcgaaa actgtggaat tgatcagcgt tggtgggaaa gcgcgttaca | 840 |
| agaaagccgg gcaattgctg tgccaggcag ttttaacgat cagttcgccg atgcagatat | 900 |
| tcgtaattat gcgggcaacg tctggtatca gcgcgaagtc tttataccga aaggttgggc | 960 |
| aggccagcgt atcgtgctgc gtttcgatgc ggtcactcat tacggcaaag tgtgggtcaa | 1020 |
| taatcaggaa gtgatggagc atcagggcgg ctatacgcca tttgaagccg atgtcacgcc | 1080 |
| gtatgttatt gccgggaaaa gtgtacgtat caccgtttgt gtgaacaacg aactgaactg | 1140 |
| gcagactatc ccgccgggaa tggtgattac cgacgaaaac ggcaagaaaa agcagtctta | 1200 |
| cttccatgat ttctttaact atgccgggat ccatcgcagc gtaatgctct acaccacgcc | 1260 |
| gaacacctgg gtggacgata tcaccgtggt gacgcatgtc gcgcaagact gtaaccacgc | 1320 |
| gtctgttgac tggcaggtgg tggccaatgg tgatgtcagc gttgaactgc gtgatgcgga | 1380 |
| tcaacaggtg gttgcaactg gacaaggcac tagcgggact ttgcaagtgg tgaatccgca | 1440 |
| cctctggcaa ccgggtgaag gttatctcta tgaactgtgc gtcacagcca aaagccagac | 1500 |
| agagtgtgat atctacccgc ttcgcgtcgg catccggtca gtggcagtga agggcgaaca | 1560 |
| gttcctgatt aaccacaaac cgttctactt tactggcttt ggtcgtcatg aagatgcgga | 1620 |
| cttacgtggc aaaggattcg ataacgtgct gatggtgcac gaccacgcat taatggactg | 1680 |
| gattggggcc aactcctacc gtacctcgca ttacccttac gctgaagaga tgctcgactg | 1740 |
| ggcagatgaa catggcatcg tggtgattga tgaaactgct gctgtcggct ttaacctctc | 1800 |
| tttaggcatt ggtttcgaag cgggcaacaa gccgaaagaa ctgtacagcg aagaggcagt | 1860 |
| caacggggaa actcagcaag cgcacttaca ggcgattaaa gagctgatag cgcgtgacaa | 1920 |
| aaaccaccca agcgtggtga tgtggagtat tgccaacgaa ccggataccc gtccgcaagt | 1980 |
| gcacgggaat atttcgccac tggcggaagc aacgcgtaaa ctcgacccga cgcgtccgat | 2040 |
| cacctgcgtc aatgtaatgt tctgcgacgc tcacaccgat accatcagcg atctctttga | 2100 |
| tgtgctgtgc ctgaaccgtt attacggatg gtatgtccaa agcggcgatt tggaaacggc | 2160 |
| agagaaggta ctggaaaaag aacttctggc ctggcaggag aaactgcatc agccgattat | 2220 |
| catcaccgaa tacggcgtgg atacgttagc cgggctgcac tcaatgtaca ccgacatgtg | 2280 |
| gagtgaagag tatcagtgtg catggctgga tatgtatcac cgcgtctttg atcgcgtcag | 2340 |
| cgccgtcgtc ggtgaacagg tatggaattt cgccgatttt gcgacctcgc aaggcatatt | 2400 |
| gcgcgttggc ggtaacaaga aagggatctt cactcgcgac cgcaaaccga gtcggcggc | 2460 |

```
ttttctgctg caaaaacgct ggactggcat gaacttcggt gaaaaaccgc agcagggagg    2520
caaacaatga ttaattaact agagcggccg ccaccgcggc ccgagattcc ggcctcttcg    2580
gccgccaagc gacccgggtg gacgtctaga ggtacctagc aattaacaga tagtttgccg    2640
gtgataattc tcttaacctc ccacactcct ttgacataac gatttatgta acgaaactga    2700
aatttgacca gatattgtgt ccgcggtgga gctccagctt ttgttccctt tagtgagggt    2760
taatttcgag cttggcgtaa tcatggtcat agctgtttcc tgtgtgaaat tgttatccgc    2820
tcacaattcc acacaacata cgagccggaa gcataaagtg taaagcctgg ggtgcctaat    2880
gagtgagcta actcacatta attgcgttgc gctcactgcc cgctttccag tcgggaaacc    2940
tgtcgtgcca gctgcattaa tgaatcggcc aacgcgcggg gagaggcggt ttgcgtattg    3000
ggcgctcttc cgcttcctcg ctcactgact cgctgcgctc ggtcgttcgg ctgcggcgag    3060
cggtatcagc tcactcaaag gcggtaatac ggttatccac agaatcaggg gataacgcag    3120
gaaagaacat gtgagcaaaa ggccagcaaa aggccaggaa ccgtaaaaag gccgcgttgc    3180
tggcgttttt ccataggctc cgcccccctg acgagcatca caaaaatcga cgctcaagtc    3240
agaggtggcg aaacccgaca ggactataaa gataccaggc gtttccccct ggaagctccc    3300
tcgtgcgctc tcctgttccg accctgccgc ttaccggata cctgtccgcc tttctccctt    3360
cgggaagcgt ggcgctttct catagctcac gctgtaggta tctcagttcg gtgtaggtcg    3420
ttcgctccaa gctgggctgt gtgcacgaac cccccgttca gcccgaccgc tgcgccttat    3480
ccggtaacta tcgtcttgag tccaacccgg taagacacga cttatcgcca ctggcagcag    3540
ccactggtaa caggattagc agagcgaggt atgtaggcgg tgctacagag ttcttgaagt    3600
ggtggcctaa ctacggctac actagaagga cagtatttgg tatctgcgct ctgctgaagc    3660
cagttacctt cggaaaaaga gttggtagct cttgatccgg caaacaaacc accgctggta    3720
gcggtggttt ttttgtttgc aagcagcaga ttacgcgcag aaaaaaagga tctcaagaag    3780
atcctttgat cttttctacg gggtctgacg ctcagtggaa cgaaaactca cgttaaggga    3840
ttttggtcat gagattatca aaaaggatct tcacctagat ccttttaaat taaaaatgaa    3900
gttttaaatc aatctaaagt atatatgagt aaacttggtc tgacagttac caatgcttaa    3960
tcagtgaggc acctatctca gcgatctgtc tatttcgttc atccatagtt gcctgactcc    4020
ccgtcgtgta gataactacg atacgggagg gcttaccatc tggccccagt gctgcaatga    4080
taccgcgaga cccacgctca ccggctccag atttatcagc aataaaccag ccagccggaa    4140
gggccgagcg cagaagtggt cctgcaactt tatccgcctc catccagtct attaattgtt    4200
gccgggaagc tagagtaagt agttcgccag ttaatagttt gcgcaacgtt gttgccattg    4260
ctacaggcat cgtggtgtca cgctcgtcgt ttggtatggc ttcattcagc tccggttccc    4320
aacgatcaag gcgagttaca tgatccccca tgttgtgcaa aaaagcggtt agctccttcg    4380
gtcctccgat cgttgtcaga agtaagttgg ccgcagtgtt atcactcatg gttatggcag    4440
cactgcataa ttctcttact gtcatgccat ccgtaagatg cttttctgtg actggtgagt    4500
actcaaccaa gtcattctga gaatagtgta tgcggcgacc gagttgctct tgcccggcgt    4560
caatacggga taataccgcg ccacatagca gaactttaaa agtgctcatc attggaaaac    4620
gttcttcggg gcgaaaactc tcaaggatct taccgctgtt gagatccagt tcgatgtaac    4680
ccactcgtgc acccaactga tcttcagcat cttttacttt caccagcgtt tctgggtgag    4740
caaaaacagg aaggcaaaat gccgcaaaaa agggaataag ggcgacacgg aaatgttgaa    4800
tactcatact cttccttttt caatattatt gaagcattta tcagggttat tgtctcatga    4860
```

```
gcggatacat atttgaatgt atttagaaaa ataaacaaat aggggttccg cgcacatttc    4920
cccgaaaagt gccacctgac gcgccctgta gcggcgcatt aagcgcggcg ggtgtggtgg    4980
ttacgcgcag cgtgaccgct acacttgcca gcgccctagc gcccgctcct ttcgctttct    5040
tcccttcctt tctcgccacg ttcgccggct ttccccgtca gctctaaat cggggggctcc    5100 ctttagggtt ccgatttagt gctttacggc acctcgaccc caaaaaactt gattagggtg    5160
atggttcacg tagtgggcca tcgccctgat agacggtttt tcgccctttg acgttggagt    5220
ccacgttctt taatagtgga ctcttgttcc aaactggaac aacactcaac cctatctcgg    5280
tctattcttt tgatttataa gggattttgc cgatttcggc ctattggtta aaaaatgagc    5340
tgatttaaca aaaatttaac gcgaatttta acaaaatatt aacgcttaca atttccattc    5400
gccattcagg ctgcgcaact gttgggaagg cgatcggtg cgggcctctt cgctattacg    5460
ccagctggcg aaggggggat gtgctgcaag gcgattaagt tgggtaacgc cagggttttc    5520
ccagtcacga cgttgtaaaa cgacggccag tgaattgtaa tacgactcac tatagggcga    5580
attgggtacc gggccccccc tcgaggtcga tggtgtcgat aagcttgata tcgaattcat    5640
gtcacacaaa ccgatcttcg cctcaaggaa acctaattct acatccgaga gactgccgag    5700
atccagtcta cactgattaa ttttcgggcc aataatttaa aaaaatcgtg ttatataata    5760
ttatatgtat tatatatata catcatgatg atactgacag tcatgtccca ttgctaaata    5820
gacagactcc atctgccgcc tccaactgat gttctcaata tttaaggggt catctcgcat    5880
tgtttaataa taaacagact ccatctaccg cctccaaatg atgttctcaa atatattgt    5940 atgaacttat ttttattact tagtattatt agacaactta cttgctttat gaaaaacact    6000
tcctatttag gaaacaattt ataatggcag ttcgttcatt taacaattta tgtagaataa    6060
atgttataaa tgcgtatggg aaatcttaaa tatggatagc ataaatgata tctgcattgc    6120
ctaattcgaa atcaacagca acgaaaaaaa tcccttgtac aacataaata gtcatcgaga    6180
aatatcaact atcaaagaac agctattcac acgttactat tgagattatt attggacgag    6240
aatcacacac tcaactgtct ttctctcttc tagaaataca ggtacaagta tgtactattc    6300
tcattgttca tacttctagt catttcatcc cacatattcc ttggatttct ctccaatgaa    6360
tgacattcta tcttgcaaat tcaacaatta taataagata taccaaagta gcggtatagt    6420
ggcaatcaaa aagcttctct ggtgtgcttc tcgtatttat ttttattcta atgatccatt    6480
aaaggtatat atttatttct tgttatataa tccttttgtt tattacatgg gctggataca    6540
taaaggtatt ttgatttaat tttttgctta aattcaatcc cccctcgttc agtgtcaact    6600
gtaatggtag gaaattacca tactttgaa gaagcaaaaa aaatgaaaga aaaaaaaat    6660 cgtatttcca ggttagacgt tccgcagaat ctagaatgcg gtatgcggta cattgttctt    6720
cgaacgtaaa agttgcgctc cctgagatat tgtacatttt tgcttttaca agtacaagta    6780
catcgtacaa ctatgtacta ctgttgatgc atccacaaca gtttgttttg ttttttttg    6840 ttttttttt ttctaatgat tcattaccgc tatgtatacc tacttgtact tgtagtaagc    6900
cgggttattg gcgttcaatt aatcatagac ttatgaatct gcacggtgtg cgctgcgagt    6960
tacttttagc ttatgcatgc tacttgggtg taatattggg atctgttcgg aaatcaacgg    7020
atgctcaacc gatttcgaca gtaataattt gaatcgaatc ggagcctaaa atgaacccga    7080
gtatatctca taaattctc ggtgagaggt ctgtgactgt cagtacaagg tgccttcatt    7140
atgccctcaa ccttaccata cctcactgaa tgtagtgtac ctctaaaaat gaaatacagt    7200
```

```
gccaaaagcc aaggcactga gctcgtctaa cggacttgat atacaaccaa ttaaaacaaa    7260
tgaaaagaaa tacagttctt tgtatcattt gtaacaatta ccctgtacaa actaaggtat    7320
tgaaatccca caatattccc aaagtccacc cctttccaaa ttgtcatgcc tacaactcat    7380
ataccaagca ctaacctacc aaacaccact aaaaccccac aaaatatatc ttaccgaata    7440
tacagtaaca agctaccacc acactcgttg ggtgcagtcg ccagcttaaa gatatctatc    7500
cacatcagcc acaactccct tcctttaata aaccgactac acccttggct attgaggtta    7560
tgagtgaata tactgtagac aagacacttt caagaagact gtttccaaaa cgtaccactg    7620
tcctccacta caaacacacc caatctgctt cttctagtca aggttgctac accggtaaat    7680
tataaatcat catttcatta gcagggcagg gcccttttta tagagtctta tacactagcg    7740
gaccctgccg gtagaccaac ccgcaggcgc gtcagtttgc tccttccatc aatgcgtcgt    7800
agaaacgact tactccttct tgagcagctc cttgaccttg ttggcaacaa gtctccgacc    7860
tcggaggtgg aggaagagcc tccgatatcg gcggtagtga taccagcctc gacggactcc    7920
ttgacggcag cctcaacagc gtcaccggcg ggcttcatgt taagagagaa cttgagcatc    7980
atggcggcag acagaatggt ggcaatgggg ttgaccttct gcttgccgag atcggggggca    8040 gatccgtgac agggctcgta cagaccgaac gcctcgttgg tgtcgggcag agaagccaga    8100
gaggcggagg gcagcagacc cagagaaccg gggatgacgg aggcctcgtc ggagatgata    8160
tcgccaaaca tgttggtggt gatgatgata ccattcatct tggagggctg cttgatgagg    8220
atcatggcgg ccgagtcgat cagctggtgg ttgagctcga gctgggggaa ttcgtccttg    8280
aggactcgag tgacagtctt tcgccaaagt cgagaggagg ccagcacgtt ggccttgtca    8340
agagaccaca cgggaagagg ggggttgtgc tgaagggcca ggaaggcggc cattcgggca    8400
attcgctcaa cctcaggaac ggagtaggtc tcggtgtcgg aagcgacgcc agatccgtca    8460
tcctcctttc gctctccaaa gtagatacct ccgacgagct ctcggacaat gatgaagtcg    8520
gtgccctcaa cgtttcggat gggggagaga tcggcgagct tgggcgacag cagctggcag    8580
ggtcgcaggt tggcgtacag gttcaggtcc tttcgcagct tgaggagacc ctgctcgggt    8640
cgcacgtcgg ttcgtccgtc gggagtggtc catacggtgt tggcagcgcc tccgacagca    8700
ccgagcataa tagagtcagc ctttcggcag atgtcgagag tagcgtcggt gatgggctcg    8760
ccctccttct caatggcagc tcctccaatg agtcggtcct caaacacaaa ctcggtgccg    8820
gaggcctcag caacagactt gagcaccttg acggcctcgg caatcacctc ggggccacag    8880
aagtcgccgc cgagaagaac aatcttcttg gagtcagtct tggtcttctt agtttcgggt    8940
tccattgtgg atgtgtgtgg ttgtatgtgt gatgtggtgt gtggagtgaa aatctgtggc    9000
tggcaaacgc tcttgtatat atacgcactt ttgcccgtgc tatgtggaag actaaacctc    9060
cgaagattgt gactcaggta gtgcggtatc ggctagggac ccaaaccttg tcgatgccga    9120
tagcgctatc gaacgtaccc cagccggccg ggagtatgtc ggaggggaca tacgagatcg    9180
tcaagggttt gtggccaact ggtaaataaa tgatgtcgac gttt                    9224

<210> SEQ ID NO 25
<211> LENGTH: 718
<212> TYPE: DNA
<213> ORGANISM: Yarrowia lipolytica

<400> SEQUENCE: 25
ctacaccttg cagagtggag ctgtctccca tttccaagtc cagagtgtgg acgttcgggc      60
ttttcgagaa tgtcgagcag aaacagggtc gagttggcgc ataagtaccc tctttcgatc     120
```

```
tgtttaacct ggagttgggg tgttattttg gattatgata aaaagaaaag aatgaaaaaa      180
aaagaaaaaa aaagaaaaaa aagaaaaaaa aagaaaaaag aagacagtga caattagcat      240
ccaaccataa gagcgacaca agagactcga actcagaaca cttgtatctg gccacatgtg      300
cttcgtctct cagtctctcc atcgcttcta aattacccca acatgtgcca aagttcaatg      360
ctagacagca atagggttcc ccccacaatc ttgggcagat gagagtgggg cggaggagat      420
gtcatggtca attgtggcgt caatggagcg tttaaactgg gcccaaaagt tgatagggtc      480
gttcattgac agattaggat tgtagcggtc aaaagaaccc cccgaaaaag tccctcgaca      540
ctctctctac catctcccca aaatcgcctt catgtgataa actctagcgc ggggccgtta      600
ctctaacgaa cttagagaca ttcacatgcg gaggtaccgt agctacaagt accagtagag      660
gaagtccaag tggataaatc gtcttcccga ataccgactt ttctcaccac caattgcc        718
```

<210> SEQ ID NO 26
<211> LENGTH: 8867
<212> TYPE: DNA
<213> ORGANISM: Artificial Sequence
<220> FEATURE:
<223> OTHER INFORMATION: Plasmid
<400> SEQUENCE: 26

```
aaacaatgct agacagcaat agggttcccc ccacaatctt gggcagatga gagtggggcg       60
gaggagatgt catggtcaat tgtggcgtca atggagcgtt taatgggccc aaaagttgat      120
agggtcgttc attgacagat taggattgta gcggtcaaaa gaaccccccg aaaaagtccc      180
tcgacactct ctctaccatc tccccaaaat cgccttcatg tgataaactc tagcgcgggg      240
ccgttactct aacgaactta gagacattca catgcggagg taccgtagct acaagtacca      300
gtagaggaag tccaagtgga taaatcgtct tcccgaatac cgacttttct caccaccaat      360
tgccatggta cgtcctgtag aaaccccaac ccgtgaaatc aaaaaactcg acggcctgtg      420
ggcattcagt ctggatcgcg aaaactgtgg aattgatcag cgttggtggg aaagcgcgtt      480
acaagaaagc cgggcaattg ctgtgccagg cagttttaac gatcagttcg ccgatgcaga      540
tattcgtaat tatgcgggca acgtctggta tcagcgcgaa gtctttatac cgaaaggttg      600
ggcaggccag cgtatcgtgc tgcgtttcga tgcggtcact cattacggca aagtgtgggt      660
caataatcag gaagtgatgg agcatcaggg cggctatacg ccatttgaag ccgatgtcac      720
gccgtatgtt attgccggga aaagtgtacg tatcaccgtt tgtgtgaaca acgaactgaa      780
ctggcagact atcccgccgg gaatggtgat taccgacgaa aacggcaaga aaaagcagtc      840
ttacttccat gatttcttta actatgccgg gatccatcgc agcgtaatgc tctacaccac      900
gccgaacacc tgggtggacg atatcaccgt ggtgacgcat gtcgcgcaag actgtaacca      960
cgcgtctgtt gactggcagg tggtggccaa tggtgatgtc agcgttgaac tgcgtgatgc     1020
ggatcaacag gtggttgcaa ctggacaagg cactagcggg actttgcaag tggtgaatcc     1080
gcacctctgg caaccgggtg aaggttatct ctatgaactg tgcgtcacag ccaaaagcca     1140
gacagagtgt gatatctacc cgcttcgcgt cggcatccgg tcagtggcag tgaagggcga     1200
acagttcctg attaaccaca aaccgttcta ctttactggc tttggtcgtc atgaagatgc     1260
ggacttacgt ggcaaaggat tcgataacgt gctgatggtg cacgaccacg cattaatgga     1320
ctggattggg gccaactcct accgtacctc gcattaccct tacgctgaag agatgctcga     1380
ctgggcagat gaacatggca tcgtggtgat tgatgaaact gctgctgtcg gctttaacct     1440
```

```
ctctttaggc attggtttcg aagcgggcaa caagccgaaa gaactgtaca gcgaagaggc    1500
agtcaacggg gaaactcagc aagcgcactt acaggcgatt aaagagctga tagcgcgtga    1560
caaaaaccac ccaagcgtgg tgatgtggag tattgccaac gaaccggata cccgtccgca    1620
agtgcacggg aatatttcgc cactggcgga agcaacgcgt aaactcgacc cgacgcgtcc    1680
gatcacctgc gtcaatgtaa tgttctgcga cgctcacacc gataccatca gcgatctctt    1740
tgatgtgctg tgcctgaacc gttattacgg atggtatgtc caaagcggcg atttggaaac    1800
ggcagagaag gtactggaaa agaacttct ggcctggcag gagaaactgc atcagccgat    1860
tatcatcacc gaatacggcg tggatacgtt agccgggctg cactcaatgt acaccgacat    1920
gtggagtgaa gagtatcagt gtgcatggct ggatatgtat caccgcgtct tgatcgcgt    1980 cagcgccgtc gtcggtgaac aggtatgaa tttcgccgat tttgcgacct cgcaaggcat    2040
attgcgcgtt ggcggtaaca agaaagggat cttcactcgc gaccgcaaac cgaagtcggc    2100
ggcttttctg ctgcaaaaac gctggactgg catgaacttc ggtgaaaaac cgcagcaggg    2160
aggcaaacaa tgattaatta actagagcgg ccgccaccgc ggcccgagat tccggcctct    2220
tcggccgcca agcgaccgg gtggacgtct agaggtacct agcaattaac agatagtttg    2280
ccggtgataa ttctcttaac ctcccacact cctttgacat aacgatttat gtaacgaaac    2340
tgaaatttga ccagatattg tgtccgcggt ggagctccag cttttgttcc ctttagtgag    2400
ggttaatttc gagcttggcg taatcatggt catagctgtt cctgtgtga aattgttatc    2460 cgctcacaat tccacacaac atacgagccg gaagcataaa gtgtaaagcc tggggtgcct    2520
aatgagtgag ctaactcaca ttaattgcgt tgcgctcact gcccgctttc cagtcgggaa    2580
acctgtcgtg ccagctgcat taatgaatcg gccaacgcgc ggggagaggc ggtttgcgta    2640
ttgggcgctc ttccgcttcc tcgctcactg actcgctgcg ctcggtcgtt cggctgcggc    2700
gagcggtatc agctcactca aaggcggtaa tacggttatc cacagaatca ggggataacg    2760
caggaaagaa catgtgagca aaaggccagc aaaaggccag gaaccgtaaa aaggccgcgt    2820
tgctggcgtt tttccatagg ctccgccccc ctgacgagca tcacaaaaat cgacgctcaa    2880
gtcagaggtg gcgaaacccg acaggactat aaagatacca ggcgtttccc cctggaagct    2940
ccctcgtgcg ctctcctgtt ccgaccctgc cgcttaccgg atacctgtcc gcctttctcc    3000
cttcgggaag cgtggcgctt tctcatagct cacgctgtag gtatctcagt tcggtgtagg    3060
tcgttcgctc caagctgggc tgtgtgcacg aaccccccgt tcagcccgac cgctgcgcct    3120
tatccggtaa ctatcgtctt gagtccaacc cggtaagaca cgacttatcg ccactggcag    3180
cagccactgg taacaggatt agcagagcga ggtatgtagg cggtgctaca gagttcttga    3240
agtggtggcc taactacggc tacactagaa ggacagtatt tggtatctgc gctctgctga    3300
agccagttac cttcggaaaa agagttggta gctcttgatc cggcaaacaa accaccgctg    3360
gtagcggtgg tttttttgtt tgcaagcagc agattacgcg cagaaaaaaa ggatctcaag    3420
aagatccttt gatcttttct acgggtctg acgctcagtg gaacgaaaac tcacgttaag    3480
ggattttggt catgagatta tcaaaaagga tcttcaccta gatccttta aattaaaaat    3540 gaagttttaa atcaatctaa agtatatatg agtaaacttg gtctgacagt taccaatgct    3600
taatcagtga ggcacctatc tcagcgatct gtctatttcg ttcatccata gttgcctgac    3660
tccccgtcgt gtagataact acgatacggg agggcttacc atctggcccc agtgctgcaa    3720
tgataccgcg agacccacgc tcaccggctc cagatttatc agcaataaac cagccagccg    3780
gaagggccga gcgcagaagt ggtcctgcaa ctttatccgc ctccatccag tctattaatt    3840
```

```
gttgccggga agctagagta agtagttcgc cagttaatag tttgcgcaac gttgttgcca   3900
ttgctacagg catcgtggtg tcacgctcgt cgtttggtat ggcttcattc agctccggtt   3960
cccaacgatc aaggcgagtt acatgatccc ccatgttgtg caaaaaagcg gttagctcct   4020
tcggtcctcc gatcgttgtc agaagtaagt tggccgcagt gttatcactc atggttatgg   4080
cagcactgca taattctctt actgtcatgc catccgtaag atgcttttct gtgactggtg   4140
agtactcaac caagtcattc tgagaatagt gtatgcggcg accgagttgc tcttgcccgg   4200
cgtcaatacg ggataatacc gcgccacata gcagaacttt aaaagtgctc atcattggaa   4260
aacgttcttc ggggcgaaaa ctctcaagga tcttaccgct gttgagatcc agttcgatgt   4320
aacccactcg tgcacccaac tgatcttcag catcttttac tttcaccagc gtttctgggt   4380
gagcaaaaac aggaaggcaa aatgccgcaa aaagggaat aagggcgaca cggaaatgtt   4440
gaatactcat actcttcctt tttcaatatt attgaagcat ttatcagggt tattgtctca   4500
tgagcggata catatttgaa tgtatttaga aaaataaaca aatagggggtt ccgcgcacat   4560
ttccccgaaa agtgccacct gacgcgccct gtagcggcgc attaagcgcg cgggtgtgg   4620
tggttacgcg cagcgtgacc gctacacttg ccagcgccct agcgcccgct cctttcgctt   4680
tcttcccttc ctttctcgcc acgttcgccg gctttccccg tcaagctcta atcgggggc   4740
tccctttagg gttccgattt agtgctttac ggcacctcga ccccaaaaaa cttgattagg   4800
gtgatggttc acgtagtggg ccatcgccct gatagacggt ttttcgccct tgacgttgg   4860
agtccacgtt ctttaatagt ggactcttgt tccaaactgg aacaacactc aaccctatct   4920
cggtctattc ttttgattta agggatttt tgccgatttc ggcctattgg ttaaaaaatg   4980
agctgattta acaaaaattt aacgcgaatt ttaacaaaat attaacgctt acaatttcca   5040
ttcgccattc aggctgcgca actgttggga agggcgatcg gtgcgggcct cttcgctatt   5100
acgccagctg gcgaaagggg gatgtgctgc aaggcgatta agttgggtaa cgccagggtt   5160
ttcccagtca cgacgttgta aaacgacggc cagtgaattg taatacgact cactataggg   5220
cgaattgggt accgggcccc ccctcgaggt cgatggtgtc gataagcttg atatcgaatt   5280
catgtcacac aaaccgatct tcgcctcaag gaaacctaat tctacatccg agagactgcc   5340
gagatccagt ctacactgat taattttcgg gccaataatt taaaaaaatc gtgttatata   5400
atattatatg tattatatat atacatcatg atgatactga cagtcatgtc ccattgctaa   5460
atagacagac tccatctgcc gcctccaact gatgttctca atatttaagg ggtcatctcg   5520
cattgtttaa taataaacag actccatcta ccgcctccaa atgatgttct caaaatatat   5580
tgtatgaact tatttttatt acttagtatt attagacaac ttacttgctt tatgaaaaac   5640
acttcctatt taggaaacaa tttataatgg cagttcgttc atttaacaat ttatgtagaa   5700
taaatgttat aaatgcgtat gggaaatctt aaatatggat agcataaatg atatctgcat   5760
tgcctaattc gaaatcaaca gcaacgaaaa aaatcccttg tacaacataa atagtcatcg   5820
agaaatatca actatcaaag aacagctatt cacacgttac tattgagatt attattggac   5880
gagaatcaca cactcaactg tctttctctc ttctagaaat acaggtacaa gtatgtacta   5940
ttctcattgt tcatacttct agtcatttca tcccacatat tccttggatt tctctccaat   6000
gaatgacatt ctatcttgca aattcaacaa ttataataag atataccaaa gtagcggtat   6060
agtggcaatc aaaaagcttc tctggtgtgc ttctcgtatt tatttttatt ctaatgatcc   6120
attaaaggta tatatttatt tcttgttata taatcctttt gttattaca tgggctggat   6180
```

```
acataaaggt attttgattt aattttttgc ttaaattcaa tcccccctcg ttcagtgtca    6240
actgtaatgg taggaaatta ccatactttt gaagaagcaa aaaaaatgaa agaaaaaaaa    6300
aatcgtattt ccaggttaga cgttccgcag aatctagaat gcggtatgcg gtacattgtt    6360
cttcgaacgt aaaagttgcg ctccctgaga tattgtacat ttttgctttt acaagtacaa    6420
gtacatcgta caactatgta ctactgttga tgcatccaca acagtttgtt ttgttttttt    6480
ttgtttttttt tttttctaat gattcattac cgctatgtat acctacttgt acttgtagta    6540
agccgggtta ttggcgttca attaatcata gacttatgaa tctgcacggt gtgcgctgcg    6600
agttactttt agcttatgca tgctacttgg gtgtaatatt gggatctgtt cggaaatcaa    6660
cggatgctca accgatttcg acagtaataa tttgaatcga atcggagcct aaaatgaacc    6720
cgagtatatc tcataaaatt ctcggtgaga ggtctgtgac tgtcagtaca aggtgccttc    6780
attatgccct caaccttacc atacctcact gaatgtagtg tacctctaaa aatgaaatac    6840
agtgccaaaa gccaaggcac tgagctcgtc taacggactt gatatacaac caattaaaac    6900
aaaatgaaaag aaatacagtt cttgtatca tttgtaacaa ttaccctgta caaactaagg    6960
tattgaaatc ccacaatatt cccaaagtcc accccttcc aaattgtcat gcctacaact    7020
catataccaa gcactaacct accaaacacc actaaaaccc cacaaaatat atcttaccga    7080
atatacagta acaagctacc accacactcg ttgggtgcag tcgccagctt aaagatatct    7140
atccacatca gccacaactc ccttccttta ataaaccgac tacaccctg gctattgagg    7200
ttatgagtga atatactgta gacaagacac tttcaagaag actgtttcca aaacgtacca    7260
ctgtcctcca ctacaaacac acccaatctg cttcttctag tcaaggttgc tacaccggta    7320
aattataaat catcatttca ttagcagggc agggcccttt ttatagagtc ttatacacta    7380
gcggaccctg ccggtagacc aacccgcagg cgcgtcagtt tgctccttcc atcaatgcgt    7440
cgtagaaacg acttactcct tcttgagcag ctccttgacc ttgttggcaa caagtctccg    7500
acctcggagg tggaggaaga gcctccgata tcggcgtag tgataccagc ctcgacggac    7560
tccttgacgg cagcctcaac agcgtcaccg gcgggcttca tgttaagaga gaacttgagc    7620
atcatggcgg cagacagaat ggtggcaatg gggttgacct tctgcttgcc gagatcgggg    7680
gcagatccgt gacagggctc gtacagaccg aacgcctcgt tggtgtcggg cagagaagcc    7740
agagaggcg agggcagcag acccagagaa ccggggatga cggaggcctc gtcggagatg    7800
atatcgccaa acatgttggt ggtgatgatg ataccattca tcttggaggg ctgcttgatg    7860
aggatcatgg cggccgagtc gatcagctgg tggttgagct cgagctgggg gaattcgtcc    7920
ttgaggactc gagtgacagt cttcgccaa agtcgagagg aggccagcac gttggccttg    7980
tcaagagacc acacgggaag aggggggttg tgctgaaggg ccaggaaggc ggccattcgg    8040
gcaattcgct caacctcagg aacggagtag gtctcggtgt cggaagcgac gccagatccg    8100
tcatcctcct ttcgctctcc aaagtagata cctccgacga gctctcggac aatgatgaag    8160
tcggtgccct caacgtttcg gatggggag agatcggcga gctgggcga cagcagctgg    8220
cagggtcgca ggttggcgta caggttcagg tcctttcgca gcttgaggag accctgctcg    8280
ggtcgcacgt cggttcgtcc gtcgggagtg gtccatacgg tgttggcagc gcctccgaca    8340
gcaccgagca taatagagtc agccttttcg gcagatgtcga gagtagcgtc ggtgatgggc    8400
tcgccctcct tctcaatggc agctcctcca atgagtcggt cctcaaacac aaactcggtg    8460
ccggaggcct cagcaacaga cttgagcacc ttgacggcct cggcaatcac ctcggggcca    8520
cagaagtcgc cgccgagaag aacaatcttc ttggagtcag tcttggtctt cttagtttcg    8580
```

```
ggttccattg tggatgtgtg tggttgtatg tgtgatgtgg tgtgtggagt gaaaatctgt    8640
ggctggcaaa cgctcttgta tatatacgca cttttgcccg tgctatgtgg aagactaaac    8700
ctccgaagat tgtgactcag gtagtgcggt atcggctagg gacccaaacc ttgtcgatgc    8760
cgatagcgct atcgaacgta ccccagccgg ccgggagtat gtcggagggg acatacgaga    8820
tcgtcaaggg tttgtggcca actggtaaat aaatgatgtc gacgttt                  8867

<210> SEQ ID NO 27
<211> LENGTH: 361
<212> TYPE: DNA
<213> ORGANISM: Yarrowia lipolytica

<400> SEQUENCE: 27
caatgctaga cagcaatagg gttcccccca caatcttggg cagatgagag tggggcggag      60
gagatgtcat ggtcaattgt ggcgtcaatg gagcgtttaa tgggcccaaa agttgatagg     120
gtcgttcatt gacagattag gattgtagcg gtcaaaagaa ccccccgaaa aagtccctcg     180
acactctctc taccatctcc ccaaaatcgc cttcatgtga taaactctag cgcggggccg     240
ttactctaac gaacttagag acattcacat gcggaggtac cgtagctaca agtaccagta     300
gaggaagtcc aagtggataa atcgtcttcc cgaataccga cttttctcac caccaattgc     360
c                                                                     361

<210> SEQ ID NO 28
<211> LENGTH: 8768
<212> TYPE: DNA
<213> ORGANISM: Artificial Sequence
<220> FEATURE:
<223> OTHER INFORMATION: Plasmid

<400> SEQUENCE: 28
aaactgggcc caaaagttga tagggtcgtt cattgacaga ttaggattgt agcggtcaaa      60 agaaccccccc gaaaaagtcc ctcgacactc tctctaccat ctccccaaaa tcgccttcat    120
gtgataaact ctagcgcggg gccgttactc taacgaactt agagacattc acatgcggag     180
gtaccgtagc tacaagtacc agtagaggaa gtccaagtgg ataaatcgtc ttcccgaata     240 ccgactttc tcaccaccaa ttgccatggt acgtcctgta gaaaccccaa cccgtgaaat      300
caaaaaactc gacggcctgt gggcattcag tctggatcgc gaaaactgtg gaattgatca     360
gcgttggtgg gaaagcgcgt tacaagaaag ccgggcaatt gctgtgccag gcagttttaa     420
cgatcagttc gccgatgcag atattcgtaa ttatgcgggc aacgtctggt atcagcgcga     480
agtctttata ccgaaaggtt gggcaggcca gcgtatcgtg ctgcgtttcg atgcggtcac     540
tcattacggc aaagtgtggg tcaataatca ggaagtgatg gagcatcagg cggctatac      600 gccatttgaa gccgatgtca cgccgtatgt tattgccggg aaaagtgtac gtatcaccgt     660
ttgtgtgaac aacgaactga actggcagac tatcccgccg ggaatggtga ttaccgacga     720
aaacggcaag aaaaagcagt cttacttcca tgatttcttt aactatgccg ggatccatcg     780
cagcgtaatg ctctacacca cgccgaacac ctgggtggac gatatcaccg tggtgacgca     840
tgtcgcgcaa gactgtaacc acgcgtcgtt gactggcag gtggtggcca atggtgatgt      900
cagcgttgaa ctgcgtgatg cggatcaaca ggtggttgca actggacaag gcactagcgg     960
gactttgcaa gtggtgaatc cgcacctctg caaccgggt gaaggttatc tctatgaact     1020
gtgcgtcaca gccaaaagcc agacagagtg tgatatctac ccgcttcgcg tcggcatccg    1080
```

```
gtcagtggca gtgaagggcg aacagttcct gattaaccac aaaccgttct actttactgg    1140
ctttggtcgt catgaagatg cggacttacg tggcaaagga ttcgataacg tgctgatggt    1200
gcacgaccac gcattaatgg actggattgg ggccaactcc taccgtacct cgcattaccc    1260
ttacgctgaa gagatgctcg actgggcaga tgaacatggc atcgtggtga ttgatgaaac    1320
tgctgctgtc ggctttaacc tctctttagg cattggtttc gaagcgggca acaagccgaa    1380
agaactgtac agcgaagagg cagtcaacgg ggaaactcag caagcgcact acaggcgat     1440 taaagagctg atagcgcgtg acaaaaacca cccaagcgtg gtgatgtgga gtattgccaa    1500
cgaaccggat accgtccgc aagtgcacgg gaatatttcg ccactggcgg aagcaacgcg     1560
taaactcgac ccgacgcgtc cgatcacctg cgtcaatgta atgttctgcg acgctcacac    1620
cgataccatc agcgatctct ttgatgtgct gtgcctgaac cgttattacg gatggtatgt    1680
ccaaagcggc gatttggaaa cggcagagaa ggtactggaa aaagaacttc tggcctggca    1740
ggagaaactg catcagccga ttatcatcac cgaatacggc gtggatacgt agccgggct    1800 gcactcaatg tacaccgaca tgtggagtga agagtatcag tgtgcatggc tggatatgta    1860
tcaccgcgtc tttgatcgcg tcagcgccgt cgtcggtgaa caggtatgga atttcgccga    1920
ttttgcgacc tcgcaaggca tattgcgcgt tggcggtaac aagaaaggga tcttcactcg    1980
cgaccgcaaa ccgaagtcgg cggcttttct gctgcaaaaa cgctggactg catgaacttt    2040
cggtgaaaaa ccgcagcagg gaggcaaaca atgattaatt aactagagcg gccgccaccg    2100
cggcccgaga ttccggcctc ttcggccgcc aagcgacccg gtggacgtc tagaggtacc     2160 tagcaattaa cagatagttt gccggtgata attctcttaa cctcccacac tcctttgaca    2220
taacgattta tgtaacgaaa ctgaaatttg accagatatt gtgtccgcgg tggagctcca    2280
gcttttgttc cctttagtga gggttaattt cgagcttggc gtaatcatgg tcatagctgt    2340
ttcctgtgtg aaattgttat ccgctcacaa ttccacacaa catacgagcc ggaagcataa    2400
agtgtaaagc ctggggtgcc taatgagtga gctaactcac attaattgcg ttgcgctcac    2460
tgcccgcttt ccagtcggga aacctgtcgt gccagctgca ttaatgaatc ggccaacgcg    2520
cggggagagg cggtttgcgt attgggcgct cttccgcttc ctcgctcact gactcgctgc    2580
gctcggtcgt tcggctgcgg cgagcggtat cagctcactc aaaggcggta atacggttat    2640
ccacagaatc aggggataac gcaggaaaga acatgtgagc aaaaggccag caaaaggcca    2700
ggaaccgtaa aaaggccgcg ttgctggcgt ttttccatag gctccgcccc cctgacgagc    2760
atcacaaaaa tcgacgctca agtcagaggt ggcgaaaccc gacaggacta taaagatacc    2820
aggcgtttcc ccctggaagc tccctcgtgc gctctcctgt tccgaccctg ccgcttaccg    2880
gatacctgtc cgcctttctc ccttcgggaa gcgtggcgct ttctcatagc tcacgctgta    2940
ggtatctcag ttcggtgtag tcgttcgct ccaagctggg ctgtgtgcac gaacccccg      3000 ttcagcccga ccgctgcgcc ttatccggta actatcgtct tgagtccaac ccggtaagac    3060
acgacttatc gccactggca gcagccactg gtaacaggat tagcagagcg aggtatgtag    3120
gcggtgctac agagttcttg aagtggtggc ctaactacgg ctacactaga aggacagtat    3180
ttggtatctg cgctctgctg aagccagtta ccttcggaaa aagagttggt agctcttgat    3240
ccggcaaaca aaccaccgct ggtagcggtg gtttttttgt ttgcaagcag cagattacgc    3300
gcagaaaaaa aggatctcaa gaagatcctt tgatcttttc tacggggtct gacgctcagt    3360
ggaacgaaaa ctcacgttaa gggattttgg tcatgagatt atcaaaaagg atcttcacct    3420
agatcctttt aaattaaaaa tgaagtttta aatcaatcta agtatatat gagtaaactt     3480
```

-continued

```
ggtctgacag ttaccaatgc ttaatcagtg aggcacctat ctcagcgatc tgtctatttc    3540
gttcatccat agttgcctga ctccccgtcg tgtagataac tacgatacgg agggcttac    3600
catctggccc cagtgctgca atgataccgc gagacccacg ctcaccggct ccagatttat    3660
cagcaataaa ccagccagcc ggaagggccg agcgcagaag tggtcctgca actttatccg    3720
cctccatcca gtctattaat tgttgccggg aagctagagt aagtagttcg ccagttaata    3780
gtttgcgcaa cgttgttgcc attgctacag gcatcgtggt gtcacgctcg tcgtttggta    3840
tggcttcatt cagctccggt tcccaacgat caaggcgagt tacatgatcc cccatgttgt    3900
gcaaaaaagc ggttagctcc ttcggtcctc cgatcgttgt cagaagtaag ttggccgcag    3960
tgttatcact catggttatg gcagcactgc ataattctct tactgtcatg ccatccgtaa    4020
gatgcttttc tgtgactggt gagtactcaa ccaagtcatt ctgagaatag tgtatgcggc    4080
gaccgagttg ctcttgcccg gcgtcaatac gggataatac cgcgccacat agcagaactt    4140
taaaagtgct catcattgga aaacgttctt cggggcgaaa actctcaagg atcttaccgc    4200
tgttgagatc cagttcgatg taacccactc gtgcacccaa ctgatcttca gcatctttta    4260
ctttcaccag cgtttctggg tgagcaaaaa caggaaggca aaatgccgca aaaaagggaa    4320
taagggcgac acggaaatgt tgaatactca tactcttcct ttttcaatat tattgaagca    4380
tttatcaggg ttattgtctc atgagcggat acatatttga atgtatttag aaaaataaac    4440
aaataggggt tccgcgcaca tttccccgaa aagtgccacc tgacgcgccc tgtagcggcg    4500
cattaagcgc ggcgggtgtg gtggttacgc gcagcgtgac cgctacactt gccagcgccc    4560
tagcgcccgc tcctttcgct ttcttccctt cctttctcgc cacgttcgcc ggctttcccc    4620
gtcaagctct aaatcggggg ctccctttag ggttccgatt tagtgcttta cggcacctcg    4680
accccaaaaa acttgattag ggtgatggtt cacgtagtgg gccatcgccc tgatagacgg    4740
tttttcgccc tttgacgttg gagtccacgt tctttaatag tggactcttg ttccaaactg    4800
gaacaacact caaccctatc tcggtctatt cttttgattt ataagggatt tgccgattt    4860
cggcctattg gttaaaaaat gagctgattt aacaaaaatt taacgcgaat tttaacaaaa    4920
tattaacgct tacaatttcc attcgccatt caggctgcgc aactgttggg aagggcgatc    4980
ggtgcgggcc tcttcgctat tacgccagct ggcgaaaggg ggatgtgctg caaggcgatt    5040
aagttgggta acgccagggt tttcccagtc acgacgttgt aaaacgacgg ccagtgaatt    5100
gtaatacgac tcactatagg gcgaattggg taccgggccc cccctcgagg tcgatggtgt    5160
cgataagctt gatatcgaat tcatgtcaca caaaccgatc ttcgcctcaa ggaaacctaa    5220
ttctacatcc gagagactgc cgagatccag tctacactga ttaattttcg ggccaataat    5280
ttaaaaaaat cgtgttatat aatattatat gtattatata tatacatcat gatgatactg    5340
acagtcatgt cccattgcta aatagacaga ctccatctgc cgcctccaac tgatgttctc    5400
aatatttaag gggtcatctc gcattgttta ataataaaca gactccatct accgcctcca    5460
aatgatgttc tcaaaatata ttgtatgaac ttattttat tacttagtat tattagacaa    5520
cttacttgct ttatgaaaaa cacttcctat ttaggaaaca atttataatg gcagttcgtt    5580
catttaacaa tttatgtaga ataaatgtta taaatgcgta tgggaaatct taaatatgga    5640
tagcataaat gatatctgca ttgcctaatt cgaaatcaac agcaacgaaa aaaatccctt    5700
gtacaacata aatagtcatc gagaaatatc aactatcaaa gaacagctat tcacacgtta    5760
ctattgagat tattattgga cgagaatcac acactcaact gtctttctct cttctagaaa    5820
```

```
tacaggtaca agtatgtact attctcattg ttcatacttc tagtcatttc atcccacata    5880
ttccttggat ttctctccaa tgaatgacat tctatcttgc aaattcaaca attataataa    5940
gatataccaa agtagcggta tagtggcaat caaaaagctt ctctggtgtg cttctcgtat    6000
ttattttttat tctaatgatc cattaaaggt atatatttat ttcttgttat ataatccttt    6060
tgtttattac atgggctgga tacataaagg tattttgatt taattttttg cttaaattca    6120
atccccctc gttcagtgtc aactgtaatg gtaggaaatt accatacttt tgaagaagca    6180
aaaaaatga aagaaaaaaa aaatcgtatt tccaggttag acgttccgca gaatctagaa    6240
tgcggtatgc ggtacattgt tcttcgaacg taaaagttgc gctccctgag atattgtaca    6300
tttttgcttt tacaagtaca agtacatcgt acaactatgt actactgttg atgcatccac    6360
aacagtttgt tttgttttt tttgttttt tttttctaa tgattcatta ccgctatgta    6420
tacctacttg tacttgtagt aagccgggtt attggcgttc aattaatcat agacttatga    6480
atctgcacgg tgtgcgctgc gagttacttt tagcttatgc atgctacttg ggtgtaatat    6540
tgggatctgt tcggaaatca acggatgctc aaccgatttc gacagtaata atttgaatcg    6600
aatcggagcc taaaatgaac ccgagtatat ctcataaaat tctcggtgag aggtctgtga    6660
ctgtcagtac aaggtgcctt cattatgccc tcaaccttac catacctcac tgaatgtagt    6720
gtacctctaa aaatgaaata cagtgccaaa agccaaggca ctgagctcgt ctaacggact    6780
tgatatacaa ccaattaaaa caaatgaaaa gaaatacagt tctttgtatc atttgtaaca    6840
attaccctgt acaaactaag gtattgaaat cccacaatat tcccaaagtc caccccttc    6900
caaattgtca tgcctacaac tcatatacca agcactaacc taccaaacac cactaaaacc    6960
ccacaaaata tatcttaccg aatatacagt aacaagctac caccacactc gttgggtgca    7020
gtcgccagct taaagatatc tatccacatc agccacaact cccttccttt aataaaccga    7080
ctacacccctt ggctattgag gttatgagtg aatatactgt agacaagaca ctttcaagaa    7140
gactgtttcc aaaacgtacc actgtcctcc actacaaaca cacccaatct gcttcttcta    7200
gtcaaggttg ctacaccggt aaattataaa tcatcatttc attagcaggg cagggccctt    7260
tttatagagt cttatacact agcggaccct gccggtagac caacccgcag gcgcgtcagt    7320
ttgctccttc catcaatgcg tcgtagaaac gacttactcc ttcttgagca gctccttgac    7380
cttgttggca acaagtctcc gacctcgag gtggaggaag agcctccgat atcgcggta    7440
gtgataccag cctcgacgga ctccttgacg gcagcctcaa cagcgtcacc ggcgggcttc    7500
atgttaagag agaacttgag catcatggcg gcagacagaa tggtggcaat ggggttgacc    7560
ttctgcttgc cgagatcggg ggcagatccg tgacagggct cgtacagacc gaacgcctcg    7620
ttggtgtcgg gcagagaagc cagagaggcg gagggcagca gacccagaga accggggatg    7680
acggaggcct cgtcggagat gatatcgcca aacatgttgg tggtgatgat gataccattc    7740
atcttggagg gctgcttgat gaggatcatg gcggccagt cgatcagctg gtggttgagc    7800
tcgagctggg ggaattcgtc cttgaggact cgagtgacag tctttcgcca aagtcgagag    7860
gaggccagca cgttggcctt gtcaagagac cacacgggaa gaggggggtt gtgctgaagg    7920
gccaggaagg cggccattcg ggcaattcgc tcaacctcag gaacggagta ggtctcggtg    7980
tcggaagcga cgccagatcc gtcatcctcc tttcgctctc caaagtagat acctccgacg    8040
agctctcgga caatgatgaa gtcggtgccc tcaacgtttc ggatggggga gagatcggcg    8100
agcttgggcg acagcagctg gcagggtcgc aggttggcgt acaggttcag gtcctttcgc    8160
agcttgagga gaccctgctc gggtcgcacg tcggttcgtc cgtcgggagt ggtccatacg    8220
```

```
gtgttggcag cgcctccgac agcaccgagc ataatagagt cagcctttcg gcagatgtcg      8280
agagtagcgt cggtgatggg ctcgccctcc ttctcaatgg cagctcctcc aatgagtcgg      8340
tcctcaaaca caaactcggt gccggaggcc tcagcaacag acttgagcac cttgacggcc      8400
tcggcaatca cctcggggcc acagaagtcg ccgccgagaa gaacaatctt cttggagtca      8460
gtcttggtct tcttagtttc gggttccatt gtggatgtgt gtggttgtat gtgtgatgtg      8520
gtgtgtggag tgaaaatctg tggctggcaa acgctcttgt atatatacgc acttttgccc      8580
gtgctatgtg aagactaaa cctccgaaga ttgtgactca ggtagtgcgg tatcggctag        8640
ggacccaaac cttgtcgatg ccgatagcgc tatcgaacgt accccagccg gcgggagta        8700 tgtcggaggg gacatacgag atcgtcaagg gtttgtggcc aactggtaaa taatgatgt        8760 cgacgttt                                                                8768

<210> SEQ ID NO 29
<211> LENGTH: 261
<212> TYPE: DNA
<213> ORGANISM: Yarrowia lipolytica

<400> SEQUENCE: 29
tgggcccaaa agttgatagg gtcgttcatt gacagattag gattgtagcg gtcaaaagaa       60
ccccccgaaa aagtccctcg acactctctc taccatctcc ccaaaatcgc cttcatgtga      120
taaactctag cgcggggccg ttactctaac gaacttagag acattcacat gcggaggtac      180
cgtagctaca agtaccagta gaggaagtcc aagtggataa atcgtcttcc cgaataccga      240
cttttctcac caccaattgc c                                                261

<210> SEQ ID NO 30
<211> LENGTH: 207
<212> TYPE: DNA
<213> ORGANISM: Yarrowia lipolytica

<400> SEQUENCE: 30
caaaagttga tagggtcgtt cattgacaga ttaggattgt agcggtcaaa agaaccccccc      60 gaaaaagtcc ctcgacactc tctctaccat ctccccaaaa tcgccttcat gtgataaact      120
ctagcgcggg gccgttactc taacgaactt agagacattc acatgcggag gtaccgtagc      180
tacaagtacc agtagaggaa gtccaag                                          207

<210> SEQ ID NO 31
<211> LENGTH: 861
<212> TYPE: DNA
<213> ORGANISM: Yarrowia lipolytica

<400> SEQUENCE: 31
gattgattcg actggaaaca caagatgaag atggctgatc ggttcatctg cttgacttac       60
attctggata tatacgagtc gcagtgtgag ttccgactca gactggggag gatgcgacca      120
gatcgaaatc cagggcaggt ttaaactaca ccttgcagag tggagctgtc tcccatttcc      180
aagtccagag tgtggacgtt cgggcttttc gagaatgtcg agcagaaaca gggtcgagtt      240
ggcgcataag taccctcttt cgatctgttt aacctggagt tggggtgtta ttttggatta      300
tgataaaaaa gaaagaatga aaaaaaaaga aaaaaaaaga aaaaaaagaa                  360
aaaagaagac agtgacaatt agcatccaac cataagagcg acacaagaga ctcgaactca      420
gaacacttgt atctggccac atgtgcttcg tctctcagtc tctccatcgc ttctaaatta      480
```

-continued

```
ccccaacatg tgccaaagtt caatgctaga cagcaatagg gttcccccca caatcttggg        540
cagatgagag tggggcggag gagatgtcat ggtcaattgt ggcgtcaatg gagcgtttaa        600
tgggcccaaa agttgatagg gtcgttcatt gacagattag gattgtagcg gtcaaaagaa        660 cccccgaaa aagtccctcg acactctctc taccatctcc ccaaaatcgc cttcatgtga         720
taaactctag cgcggggccg ttactctaac gaacttagag acattcacat gcggaggtac        780
cgtagctaca agtaccagta gaggaagtcc aagtggataa atcgtcttcc cgaataccga       840
cttttctcac caccaattgc c                                                  861

<210> SEQ ID NO 32
<211> LENGTH: 255
<212> TYPE: DNA
<213> ORGANISM: Yarrowia lipolytica

<400> SEQUENCE: 32
caaaagttga tagggtcgtt cattgacaga ttaggattgt agcggtcaaa agaacccccc         60
gaaaaagtcc ctcgacactc tctctaccat ctccccaaaa tcgccttcat gtgataaact        120
ctagcgcggg gccgttactc taacgaactt agagacattc acatgcggag gtaccgtagc        180
tacaagtacc agtagaggaa gtccaagtgg ataaatcgtc ttcccgaata ccgactttc         240 tcaccaccaa ttgcc                                                         255

<210> SEQ ID NO 33
<211> LENGTH: 357
<212> TYPE: DNA
<213> ORGANISM: Yarrowia lipolytica

<400> SEQUENCE: 33
ctacaccttg cagagtggag ctgtctccca tttccaagtc cagagtgtgg acgttcgggc         60
ttttcgagaa tgtcgagcag aaacagggtc gagttggcgc ataagtaccc tctttcgatc       120
tgtttaacct ggagttgggg tgttattttg gattatgata aaaagaaag aatgaaaaaa         180 aaagaaaaaa aaagaaaaaa aagaaaaaaa aagaaaaaag aagacagtga caattagcat       240
ccaaccataa gagcgacaca agagactcga actcagaaca cttgtatctg gccacatgtg       300
cttcgtctct cagtctctcc atcgcttcta aattacccca acatgtgcca aagttca          357
```